(12) United States Patent
Smith

(10) Patent No.: US 7,597,122 B1
(45) Date of Patent: Oct. 6, 2009

(54) APPARATUS AND METHOD TO MONITOR THE USAGE OF A NETWORK SYSTEM OF PERSONAL HAND SANITIZING DISPENSERS

(76) Inventor: Judson L. Smith, 409 E. Walnut, Apt. 4, Greencastle, IN (US) 46135

(*) Notice: Subject to any disclaimer, the term of this patent is extended or adjusted under 35 U.S.C. 154(b) by 719 days.

(21) Appl. No.: 11/129,643

(22) Filed: May 13, 2005

Related U.S. Application Data

(63) Continuation-in-part of application No. 11/016,644, filed on Dec. 7, 2004, now abandoned, which is a continuation of application No. 09/915,606, filed on Jul. 26, 2001, now Pat. No. 6,883,563.

(51) Int. Cl.
*B65B 3/16* (2006.01)
(52) U.S. Cl. .................. 141/114; 141/21; 141/25; 222/105; 222/175
(58) Field of Classification Search .......... 141/2, 141/18, 21, 25, 67, 114; 224/148.1–148.7; 222/52, 63, 82, 95, 105, 175, 189, 207, 209, 222/211, 214, 321.7, 325; D9/448; 221/283
See application file for complete search history.

(56) References Cited

U.S. PATENT DOCUMENTS

| | | | |
|---|---|---|---|
| 3,257,077 A * | 6/1966 | Corning | ............. 239/47 |
| 3,726,436 A | 4/1973 | Despain et al. | |
| 3,815,843 A | 6/1974 | Fortune | |
| 3,828,978 A | 8/1974 | Dawson | |
| 3,869,773 A | 3/1975 | Gneiding | |
| 3,875,604 A | 4/1975 | Wurn et al. | |
| 3,878,973 A | 4/1975 | Riccio | |
| 3,932,909 A | 1/1976 | Johnson et al. | |
| 3,934,822 A | 1/1976 | Ross | |
| 3,993,190 A | 11/1976 | Schmidgall | |
| 4,018,363 A | 4/1977 | Cassia | |
| 4,019,655 A | 4/1977 | Moeller | |
| 4,043,041 A | 8/1977 | Hornick | |

(Continued)

FOREIGN PATENT DOCUMENTS

EP 0 103 675 A2 3/1984

(Continued)

OTHER PUBLICATIONS

HACCP Handwash Supervisor ©, CFEI Conception Fabrication Electronique Industrielle, Place de la Halle 89110 La Ferte Loupiere, France.

(Continued)

*Primary Examiner*—Timothy L Maust
(74) *Attorney, Agent, or Firm*—Woodard, Emhardt, Moriarty, McNett & Henry LLP

(57) ABSTRACT

A portable dispenser for a hand treatment agent includes a flexible bag containing the treatment agent. A valve assembly is sealed to the bag, and functions to receive a portion of the agent from the bag, and is manually operable to discharge the received portion from an outlet port, and automatically refill with another portion of the agent from the bag. A flexible hanger on the bag facilitates adhesive external attachment to wearing apparel of the dispenser user for easy access, and is foldable onto the bag for adhesive attachment to the bag and concealment of adhesive when the dispenser is temporarily out of use.

28 Claims, 39 Drawing Sheets

U.S. PATENT DOCUMENTS

| | | | |
|---|---|---|---|
| 4,043,054 A | 8/1977 | Crowder | |
| 4,079,867 A | 3/1978 | Tannehill | |
| 4,116,571 A | 9/1978 | Maxwell | |
| 4,121,736 A | 10/1978 | McGaw, Jr. | |
| 4,135,561 A | 1/1979 | Senelonge | |
| 4,143,853 A | 3/1979 | Abramson | |
| 4,164,306 A | 8/1979 | Perrin | |
| 4,212,758 A | 7/1980 | Shashkina et al. | |
| 4,219,367 A | 8/1980 | Cary, Jr. et al. | |
| 4,229,116 A | 10/1980 | Moore | |
| 4,238,056 A | 12/1980 | Tucker et al. | |
| 4,269,330 A | 5/1981 | Johnson | |
| 4,295,233 A | 10/1981 | Hinkel et al. | |
| 4,330,357 A | 5/1982 | Collins | |
| 4,335,837 A | 6/1982 | Bono | |
| 4,336,097 A | 6/1982 | Van Kampen et al. | |
| 4,391,309 A | 7/1983 | Steiner | |
| 4,397,050 A | 8/1983 | Davis et al. | |
| 4,398,310 A | 8/1983 | Lienhard | |
| 4,411,376 A | 10/1983 | Bennett et al. | |
| 4,429,812 A | 2/1984 | Steiner et al. | |
| 4,457,427 A | 7/1984 | Cafiero | |
| 4,470,523 A * | 9/1984 | Spector | 222/181.2 |
| 4,493,440 A | 1/1985 | von Buelow et al. | |
| 4,493,443 A | 1/1985 | Bailey | |
| 4,509,679 A | 4/1985 | Longini | |
| 4,527,764 A | 7/1985 | Krause | |
| 4,532,668 A | 8/1985 | Slonicki | |
| 4,548,607 A | 10/1985 | Harris | |
| 4,573,612 A | 3/1986 | Maddison et al. | |
| 4,606,085 A | 8/1986 | Davies | |
| 4,609,130 A | 9/1986 | Katva | |
| 4,637,934 A | 1/1987 | White | |
| 4,642,821 A | 2/1987 | Zanuso et al. | |
| 4,646,945 A | 3/1987 | Steiner et al. | |
| 4,662,195 A | 5/1987 | von Buelow et al. | |
| 4,668,231 A | 5/1987 | de Vries et al. | |
| 4,673,109 A | 6/1987 | Cassia | |
| 4,722,372 A | 2/1988 | Hoffman | |
| 4,723,690 A | 2/1988 | vom Hofe | |
| 4,752,020 A | 6/1988 | Grueter et al. | |
| 4,769,863 A | 9/1988 | Tegg et al. | |
| 4,776,494 A | 10/1988 | Holoubek | |
| 4,776,495 A | 10/1988 | Vignot | |
| 4,784,652 A | 11/1988 | Wikstrom | |
| 4,785,850 A | 11/1988 | Sanchez | |
| 4,792,064 A | 12/1988 | Loesel, Jr. et al. | |
| 4,793,517 A * | 12/1988 | Washut | 222/129 |
| 4,826,047 A | 5/1989 | Heflin | |
| 4,884,719 A | 12/1989 | Levine et al. | |
| 4,886,192 A | 12/1989 | Cassia | |
| 4,886,388 A | 12/1989 | Gulker et al. | |
| 4,896,144 A | 1/1990 | Bogstad | |
| 4,905,866 A | 3/1990 | Bartell et al. | |
| 4,905,873 A | 3/1990 | Loesel, Jr. et al. | |
| 4,928,857 A | 5/1990 | Ecker | |
| 4,930,667 A | 6/1990 | Holzner, Sr. | |
| 4,932,566 A | 6/1990 | Weinbaum | |
| 4,938,384 A | 7/1990 | Pilolla et al. | |
| 4,946,070 A | 8/1990 | Albert et al. | |
| 4,946,072 A * | 8/1990 | Albert et al. | 222/105 |
| 4,994,265 A | 2/1991 | White | |
| D315,196 S | 3/1991 | Tegg et al. | |
| 4,998,836 A | 3/1991 | Scripnick | |
| 5,018,646 A | 5/1991 | Billman et al. | |
| 5,029,732 A | 7/1991 | Wong | |
| 5,094,368 A | 3/1992 | Warehime | |
| 5,099,785 A | 3/1992 | Reed | |
| 5,105,992 A | 4/1992 | Fender et al. | |
| 5,125,577 A | 6/1992 | Frankel | |
| 5,143,262 A | 9/1992 | Edlund | |
| 5,148,948 A | 9/1992 | Granville et al. | |
| 5,169,252 A | 12/1992 | Chappell | |
| 5,183,182 A | 2/1993 | Comstock et al. | |
| 5,186,360 A | 2/1993 | Mease et al. | |
| 5,188,610 A | 2/1993 | Rains | |
| 5,197,895 A | 3/1993 | Stupecky | |
| 5,199,118 A | 4/1993 | Cole et al. | |
| 5,202,666 A | 4/1993 | Knippscheer | |
| 5,209,377 A | 5/1993 | Steiner et al. | |
| 5,215,216 A | 6/1993 | Van Marcke | |
| 5,217,035 A | 6/1993 | Van Marcke | |
| 5,226,462 A | 7/1993 | Carl | |
| 5,235,214 A | 8/1993 | Vuong et al. | |
| 5,240,147 A | 8/1993 | Frazier et al. | |
| 5,251,757 A | 10/1993 | Relyea et al. | |
| 5,255,822 A | 10/1993 | Mease et al. | |
| D341,741 S | 11/1993 | Allen et al. | |
| 5,265,628 A | 11/1993 | Sage et al. | |
| 5,265,761 A | 11/1993 | Brown | |
| 5,287,996 A | 2/1994 | Uhlig | |
| 5,290,245 A | 3/1994 | Dennis | |
| 5,305,915 A | 4/1994 | Kamysz et al. | |
| 5,307,953 A | 5/1994 | Regan | |
| 5,318,070 A | 6/1994 | Surabian | |
| 5,330,075 A | 7/1994 | Brown, Sr. | |
| 5,332,014 A | 7/1994 | Feig | |
| 5,332,096 A | 7/1994 | Battaglia | |
| 5,332,129 A | 7/1994 | Brattoli et al. | |
| 5,333,789 A | 8/1994 | Garneys | |
| 5,335,855 A | 8/1994 | Borod | |
| 5,344,047 A | 9/1994 | Chen | |
| 5,345,640 A | 9/1994 | Goss | |
| 5,350,087 A | 9/1994 | Frazier et al. | |
| 5,356,076 A | 10/1994 | Bishop | |
| 5,366,125 A | 11/1994 | Procido | |
| 5,373,970 A | 12/1994 | Ophardt | |
| 5,377,874 A | 1/1995 | Brown | |
| 5,381,932 A | 1/1995 | Humphrey | |
| 5,397,028 A | 3/1995 | Jesadanont | |
| 5,398,848 A | 3/1995 | Padamsee | |
| 5,405,269 A | 4/1995 | Stupecky | |
| 5,421,489 A | 6/1995 | Holzner, Sr. et al. | |
| D359,868 S | 7/1995 | Brandenburg et al. | |
| 5,431,283 A | 7/1995 | Weinstein et al. | |
| 5,431,309 A | 7/1995 | Ophardt | |
| 5,439,144 A | 8/1995 | Holzner | |
| 5,452,825 A | 9/1995 | Comstock et al. | |
| 5,460,295 A | 10/1995 | Law | |
| 5,464,125 A | 11/1995 | Daansen | |
| 5,466,080 A | 11/1995 | Lee | |
| 5,469,990 A | 11/1995 | Wodeslavsky | |
| 5,476,194 A | 12/1995 | Hippely | |
| 5,480,068 A | 1/1996 | Frazier et al. | |
| 5,492,247 A | 2/1996 | Shu | |
| 5,501,372 A | 3/1996 | Daansen | |
| 5,502,848 A | 4/1996 | Cowan | |
| 5,505,192 A | 4/1996 | Samiotes et al. | |
| 5,507,413 A | 4/1996 | Chen | |
| D371,514 S | 7/1996 | Daansen | |
| D371,966 S | 7/1996 | Daansen | |
| 5,535,886 A | 7/1996 | Huffer | |
| 5,542,236 A | 8/1996 | Miller | |
| 5,548,856 A | 8/1996 | Julian | |
| 5,556,005 A | 9/1996 | Banks | |
| 5,561,869 A | 10/1996 | Sarel | |
| 5,562,248 A | 10/1996 | Khalifka | |
| 5,573,041 A | 11/1996 | Skell et al. | |
| 5,590,816 A | 1/1997 | Bertram et al. | |
| D378,196 S | 2/1997 | Daansen | |
| 5,598,952 A | 2/1997 | Daansen | |
| 5,603,429 A | 2/1997 | Mulhauser et al. | |
| 5,611,465 A | 3/1997 | Lee et al. | |
| 5,625,659 A | 4/1997 | Sears | |

| | | |
|---|---|---|
| 5,632,418 A | 5/1997 | Brown |
| 5,633,048 A | 5/1997 | Bodin |
| 5,642,762 A | 7/1997 | Greenberg et al. |
| D383,673 S | 9/1997 | Daansen |
| D383,674 S | 9/1997 | Daansen |
| D383,675 S | 9/1997 | Daansen |
| D384,284 S | 9/1997 | Daansen |
| 5,664,697 A | 9/1997 | Lambelet, Jr. et al. |
| 5,670,945 A | 9/1997 | Applonie |
| 5,683,012 A | 11/1997 | Villaveces |
| 5,685,211 A | 11/1997 | Lax |
| 5,706,986 A | 1/1998 | Brandenburg et al. |
| 5,709,317 A | 1/1998 | Bertram et al. |
| 5,740,929 A | 4/1998 | Frankel |
| 5,771,925 A | 6/1998 | Lewandowski |
| 5,791,525 A | 8/1998 | Fan |
| 5,793,653 A | 8/1998 | Segal |
| 5,801,735 A | 9/1998 | Lorenze, Jr. et al. |
| 5,810,201 A | 9/1998 | Besse et al. |
| 5,812,059 A | 9/1998 | Shaw et al. |
| 5,816,404 A | 10/1998 | Seidler |
| 5,819,986 A | 10/1998 | Last et al. |
| 5,829,636 A | 11/1998 | Vuong et al. |
| 5,842,608 A | 12/1998 | Buchler |
| 5,862,546 A | 1/1999 | Kim |
| 5,863,497 A | 1/1999 | Dirksing |
| 5,878,914 A | 3/1999 | Johnson |
| 5,927,548 A | 7/1999 | Villaveces |
| 5,945,910 A | 8/1999 | Gorra |
| 5,960,991 A | 10/1999 | Ophardt |
| 5,980,144 A | 11/1999 | DeBourg et al. |
| 5,988,429 A | 11/1999 | Coe |
| 5,988,440 A | 11/1999 | Saunders et al. |
| 5,992,698 A | 11/1999 | Copeland et al. |
| 6,000,429 A | 12/1999 | Van Marcke |
| 6,000,626 A | 12/1999 | Futo et al. |
| 6,006,388 A | 12/1999 | Young |
| 6,012,613 A | 1/2000 | Chen |
| 6,022,102 A | 2/2000 | Ikkatai |
| 6,035,477 A | 3/2000 | Robert |
| 6,036,058 A | 3/2000 | Chou |
| 6,036,393 A | 3/2000 | Youtcheff et al. |
| 6,038,331 A | 3/2000 | Johnson |
| 6,050,450 A | 4/2000 | Gardos |
| 6,053,604 A | 4/2000 | Sato et al. |
| 6,062,420 A | 5/2000 | Krouwel et al. |
| 6,070,958 A | 6/2000 | Kanome |
| 6,098,835 A | 8/2000 | DeJonge |
| 6,155,424 A | 12/2000 | Dubach |
| 6,228,375 B1 | 5/2001 | Kocher |
| 6,236,317 B1 | 5/2001 | Cohen et al. |
| 6,273,307 B1 | 8/2001 | Gross et al. |
| 6,283,334 B1 | 9/2001 | Mahaffey et al. |
| 6,392,546 B1 | 5/2002 | Smith |
| 6,398,106 B1 | 6/2002 | Ulvr et al. |
| 6,404,837 B1 | 6/2002 | Thompson et al. |
| 6,415,983 B1 | 7/2002 | Ulvr et al. |
| 6,426,701 B1 | 7/2002 | Levy et al. |
| D512,648 S * | 12/2005 | Smith et al. .................. D9/702 |
| 7,025,231 B2 * | 4/2006 | Rutherford et al. ....... 222/181.3 |
| 2002/0138649 A1 | 9/2002 | Cartmell et al. |

FOREIGN PATENT DOCUMENTS

| | | |
|---|---|---|
| WO | WO 99/43855 A1 | 9/1999 |
| WO | WO 02/27486 A1 | 4/2002 |
| WO | WO 02/75565 A1 | 9/2002 |

OTHER PUBLICATIONS

HyGenius Handwashing Verification—Compliance Control, Compliance Control © 1999.

The Clean Hands Company, Clean Hands Hand Washing Monitor, 10830 Galt Industrial Drive, St. Louis, MO 63132, © 1998 ShoeDesigns Multimedia.

Mobile Hand Washing Unit, H+ P labortechnik.

Wallgate, Recessed Molded Hand Washer-Dryer, Chem-Plus Inc.

* cited by examiner

APPARATUS AND METHOD TO MONITOR THE USAGE OF A NETWORK SYSTEM OF PERSONAL HAND SANITIZING DISPENSERS

CROSS-REFERENCE TO RELATED APPLICATIONS

This application is a continuation-in-part of U.S. patent application Ser. No. 11/016,644 filed Dec. 17, 2004, now abandoned, which was a continuation application of Ser. No. 09/915,606 filed Jul. 26, 2001 and issued Apr. 26, 2005, as U.S. Pat. No. 6,883,563. Priority is claimed based on these two prior applications.

FIELD OF THE INVENTION

This invention generally relates to personal, portable hand cleaning agent delivery dispensers used collectively in concert as a network system by various yet distinct healthcare personnel, and patient groups within a hospital facility, and more particularly a hand cleaning system that incorporates hand cleaning unit dose agent dispensers, and control stations that can issue, retrieve, refill, replace said agent or agent dispensers and even more particularly, the means to record the usage activity within a given time frame of said agent dispensers by tracking and recording by a user's unique identifier, and or by the agent dispenser's unique identifier, and or by the agent dispenser's agent cartridge's unique identifier and or by the unique agent refilling event of an agent dispenser and to report how many hand cleaning procedures occurred during a given time frame that said dispenser was in usage by a user.

BACKGROUND OF THE INVENTION

It is a well documented and widely recognized fact that healthcare personnel and patients of a healthcare facility can help prevent hospital acquired infections (nosocomial infections) by sanitizing their hands on a more consistent and frequent basis.

Our mothers were right when they would say, "WASH YOUR HANDS!". More than 150 years ago, a Hungarian physician, Dr. Iemaz Semmelweis, discovered that "childbed fever", the infection that routinely killed women who had just given birth, was being spread by his colleagues' bacteria-laden hands.

In 1842, Dr. Daniel Layman presented a report to the Indiana State Medical Society which informed them of his uncommon practice of routinely washing hands before and after patient contacts, which he found greatly reduced infections and illnesses in patients—the doctors were astonished.

Yet, even today, according to research reported in The Annals of Internal Medicine, it was found that the lowest rates of hand washing compliance in a hospital were among the busy healthcare personnel in high-risk intensive care units.

According to the Centers for Disease Control and Prevention (CDC), 5 percent of the people admitted to hospitals, about 1.8 million patients, will acquire an infection there. Twenty thousand of them will die as a direct result, and hospital-acquired infection will contribute to the deaths of 70,000 more people, far more than the nearly 40,000 Americans who die of breast cancer each year.

The CDC estimates that the annual cost to treat nosocomial infection to be $4.5 billion. The problem is getting worse. Though hospital patient stays are shorter and less frequent than they were 20 years ago, today's patients are generally sicker and more vulnerable. As a result, in the last two decades the rate of hospital-acquired infection has risen 36 percent.

The reasons given on why healthcare workers do not wash their hands when required are lack of time, inaccessible sinks, rough paper towels and hands being chapped from excessive washing.

New and improved waterless alcohol based hand sanitizers have provided more convenience to a healthcare worker to clean their hands more frequently.

Products such as GOJO Industries, Inc., Akron, Ohio; Purell® brand and Ecolab, Inc., St. Paul, Minn., Cida-Rinse® Gel brand represent some of these types of waterless alcohol based hand sanitizers.

Patients within a healthcare facility often acquire an infection (nosocomial infection) by coming in contact with people and/or item surfaces that contain harmful transient bacteria and viruses. Many possible cross-contamination elements exist within the patients' environment. In most healthcare facilities more than one (1) patient occupies a "patient room". In such situations, patients share many items within a patient room such as: phone, TV remote, bathroom, bed divider, wheel chair, walker, water pitcher, food menu card, hand cleaning soap dispenser, etc. Additionally, patients also have numerous hand contacts with visitors such as relatives and friends and with nurses, doctors, technicians, etc., all of which represent potential sources for contraction of transient types of harmful bacteria and viruses.

Patients will sometimes inadvertently and unknowingly make hand contact with their own bandages, dressings, IV sites, etc. with contaminated hands. Patients in a healthcare facility often have an illness that has compromised their immune system making them more susceptible to transient forms of bacteria and viruses.

Patients of a healthcare facility have few resources to properly keep their hands clean. A patient can wash their hands in a room sink or bathroom sink. This of course requires the patient to move from a location or position like a bed or wheel chair to do so. Many patients are not capable of such movement. In many cases a healthcare worker will sometimes carry to a non-mobile patient a portable wash tray for personal hand cleaning. This procedure can burden the healthcare worker who has many important responsibilities to perform for many patients.

As described in the foregoing, there are many areas within a hospital environment that require consistent hand cleaning by healthcare personnel and patients. Administrative healthcare personnel frequently establish hand-cleaning guidelines for these different hospital areas, which require that healthcare workers and patients follow certain hand cleaning protocols. Compliance performance of the protocols is essentially monitored and measured through observation techniques, which sometimes results in costly non-representative and/or inaccurate data. The different hospital departments and the level of patient healthcare provided by each department vary greatly. Departments such as intensive care and critical care require more patient contacts by healthcare workers than the patients in the general recovery and rehabilitation departments. The different levels of patient care require different levels and standards to achieve hand-cleaning compliance. Regardless of the differences in hand cleaning protocols and the compliance standards, hospital administrators need a system that can provide uniformity in the hand cleaning activity throughout the hospital facility and a means to measure the performance of the healthcare personnel and patients that perform hand-cleaning operations. My invention and the novelties it incorporates provides a network system of hand cleaning dispensers operated with uniform procedures that can be used by healthcare workers and patients regardless of the department or level of care provided, and a compliance monitoring/measurement system that produces the hand cleaning event data the hospital administrators require to manage the programs to reduce nosocomial infections.

U.S. Pat. No. 5,683,012, and U.S. Pat. No. 5,927,548 issued to James Vellaveces on Nov. 4, 1997 and Jul. 27, 1999, respectively, disclose a novel, body-worn dispenser for alcohol-glycerin disinfectant gel that doctors and nurses can use to disinfect their hands before and after patient contacts. Said device as describe in U.S. Pat. Nos. 5,683,012 and 5,927,548 could be easily used by patients to encourage routine hand disinfection and also prevent the likelihood of microbial cross-contamination by its single person use, but again U.S. Pat. Nos. 5,683,012 and 5,927,548 do not disclose any means to monitor, track or record the usage dose applications of the disinfecting gel dispenser nor do U.S. Pat. Nos. 5,683,012 and 5,927,548 disclose any means for its piston pump which can be variably actuated depending on the amount of pressure applied by the user's hand, to dispense exact dose applications of the disinfecting gel but only to describe its fluid output as a "small amount" from a bag type replaceable cartridge.

U.S. Pat. No. 5,476,194 issued to Keith Hippely on Dec. 19, 1995 and U.S. Pat. No. 5,819,986 issued to Laurens Last on Oct. 12, 1998 both describe personal, portable, and refillable fluid dispensers. U.S. Pat. No. 5,476,194 discloses an attachment means for a dispenser device to be worn on the body of the user. U.S. Pat. No. 5,819,986 describes a piston action pump to deliver an amount of fluid in the same manner as previously disclosed by the Vellaveces Patent. Neither U.S. Pat. No. 5,819,986 nor U.S. Pat. No. 5,476,194 disclose any method or apparatus to provide uniform unit dose applications of the fluid dispensed or methods to monitor, track, record and report usage information of a fluid dispenser.

U.S. Pat. No. 5,945,910 issued to William Gorra on Aug. 3, 1999 describes a method and apparatus for monitoring and reporting hand washing, U.S. Pat. No. 5,670,945 issued to Alan Applonie on Sep. 23, 1999 also describes a self-monitoring hand sanitizing station. U.S. Pat. No. 5,202,666 discloses a method and apparatus for enhancing hygiene. The preceding three (3) patents identified, refer in general to a non-portable wash station that many people access to wash their hands. Each patent describes separate novel methods and apparatus to monitor, record and report various hand washing activity that occurs at a given wash station.

There is a substantial prior art that discloses refillable types of soap dispensers such as U.S. Pat. No. 5,492,247 that describes a fluid reservoir that is replaceable from a rigidly mounted dispenser utilized by many users. U.S. Pat. No. 4,722,372 further describes a dispenser for multiple user access with a disposable fluid reservoir.

U.S. Pat. No. 5,226,462 discloses a unique method and apparatus to accurately introduce measured amounts of liquid into receptacles. Additionally, U.S. Pat. No. 4,135,561 describes a similar method and apparatus for filling vials in an automated system.

There is also substantial prior art relating to the refilling of ink cartridges of printing apparatus. U.S. Pat. No. 6,022,102 describes a novel method to automatically refill a printer's ink cartridge when empty. Although there is a considerable amount of patents issued for automatically refilling apparatus and methods, I am not aware of any prior art which directly relates to refilling a hand-held, hand-operated, personal and portable fluid dispenser that upon its refilling process the amount of fluid used to refill said dispenser is recorded as to determine how much fluid was used over a certain time frame by a specific dispenser and by a specific user.

I am not aware of any prior art which discloses a method or apparatus that, in a system, monitors, tracks, records and reports the individual usage of a personal cleaning agent dispenser.

SUMMARY OF THE INVENTION

One embodiment of the present invention is a hand-held, hand-operated, portable, personal hand cleaning agent dispenser that comprises an operator press pad activator, a precise unit dose agent discharge valving and nozzle means, an agent reservoir that can be single or multiple compartment, and wherein the dispenser can be refilled or replaced when empty. Another aspect of the present invention is a control station apparatus having means to record into computer memory processor by a unique identifier, the issuance of agent dispensers, agent reservoirs, and refillable agent dispensers to a user by that user's unique identifier.

Another aspect of the present invention is a control station apparatus that measures and records into computer memory, with unique identifier data the quantity (by weight or volume) of said agent that is used by or before the refilling operation of a refillable agent dispenser.

Another aspect of the present invention is the way that the dispenser can be attached to a user's clothing at a position that encourages its use without interference to the user's normal activity. As can be understood from the foregoing, the present invention is able to provide a network system of hand cleaning agent dispensers to a variety of users and which can provide different levels of information that has the capability to report:

1) User by that user's unique identifier;
2) Agent dispenser by that dispensers unique identifier;
3) Agent dispenser's reservoir cartridge by that cartridge unique identifier;
4) Quantity of agent used by user using an agent dispenser or agent dispenser with agent cartridge during a certain time frame.

DETAILED DESCRIPTION OF THE DRAWINGS

Figure 1:
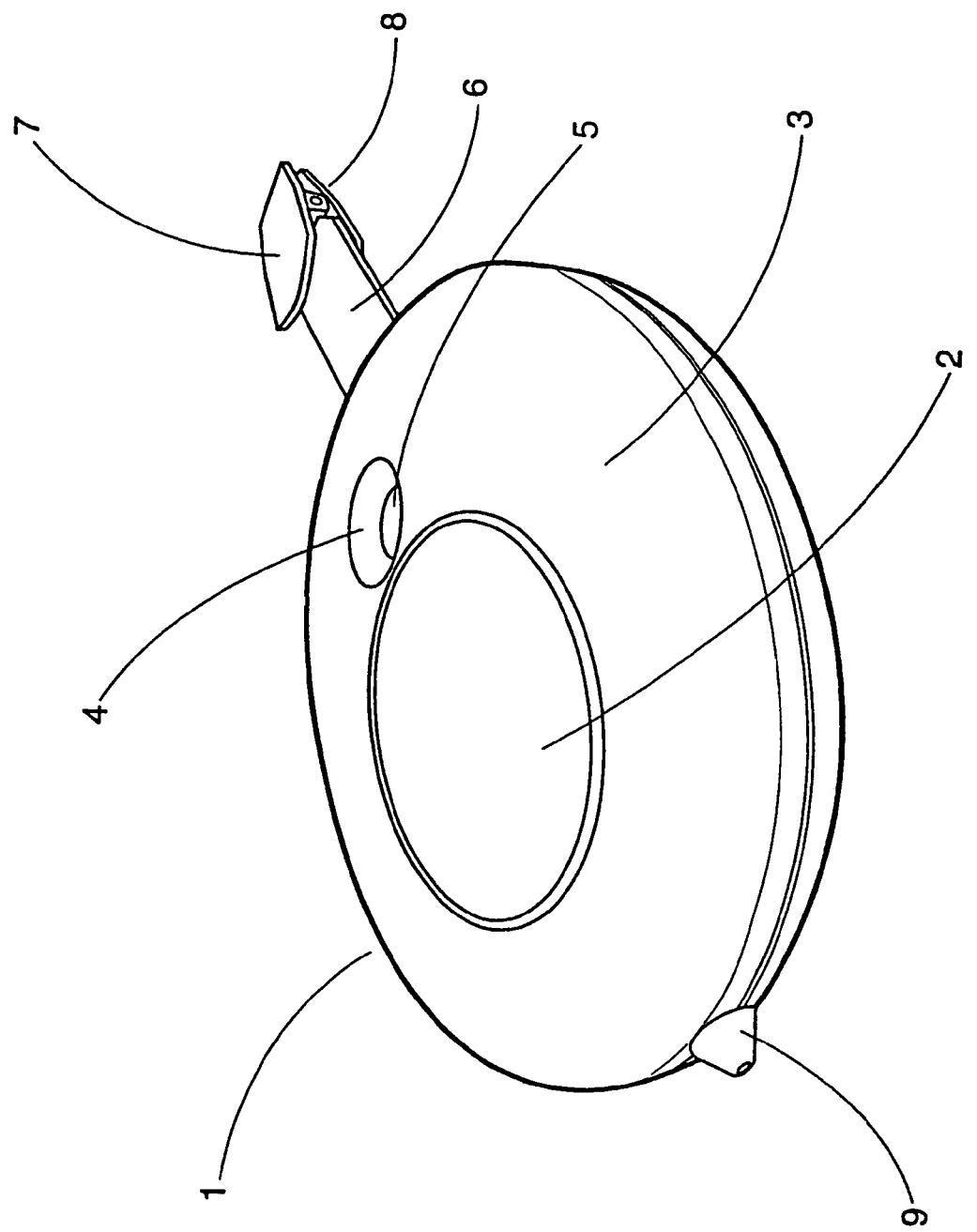
FIG. 1 is a perspective view drawing of one embodiment of the present invention's dispenser apparatus.

Referring to FIG. 1, the illustrated fluid dispenser 1 is a handheld, hand-operated portable and personal type of dispenser. It comprises a top half section 3 and a bottom half section 4A (FIG. 2A). The top half section 3 contains, as part of its one (1) piece construction, a thin flexible material section press pad 2. The top half section contains a slope entry 4 into hole 5 for mating with transport rod 75 to be described below. The bottom half-section of the dispenser 1 has a mirror image like slope entry 4 into hole 5.

A fluid ejection nozzle 9 is at the front end, and a clothing-type, spring-loaded clip 7 is connected to the rear end of the tail extension 6 and has a pivot or hinge at 8. The dispenser's nozzle 9 is used for ejecting fluid from dispenser 1 and for receiving fluid into the dispenser when filling.

The internal section (FIG. 4) of the dispenser 1 comprises a fluid unit dose piston pump 11 with actuator piston rod 18 that is held in its most upward position by the attachment of said piston rod 18 to the underside of press pad 2, which may be an elastomeric polymer having a memory to return to its most upward position. When a user presses pad 2, its connection to piston rod 18 compresses downward on piston 11 (FIG. 3), causing fluid within piston chamber to exit piston chamber port 21 and to enter fluid manifold port 27 (FIG. 5) and travel through fluid conduit 29 and into and through check valve 25 and out exit port 23 into and out of dispenser nozzle 9 (FIG. 1).

Upon the user's release of press pad 2, the press pad 2 will return to its most upward position, aided by a spring, if desired, causing the piston rod 18 to return the piston to its most upward position, causing a vacuum assist to draw fluid from fluid storage cavity 13 (FIG. 4) to exit said cavity at openings 14 to enter entry ports 19 and 20 equally. The fluid from ports 19 and 20 travels through conduit lines 31 and 32 equally to meet at fluid conduit line 30 and to enter check valve 26 and out to port 21 of the piston chamber 11.

An example of the type of check valves used for dispenser to dispense fluid would be check valve cartridges manufactured by SMART PRODUCTS INC. 1710 Ringwood, Ave., San Jose, Calif. 95131. The check valves that would be utilized by the dispenser to eject fluid and to refill piston chamber (25 & 26) would typically be a Smart Products 110PPB-3. The check valve used for the dispenser refilling (valve 24) would typically be a Smart Products 110PPB-10#. When a dispenser 1 is being refilled with fluid at the control station 34, as will be described, fluid enters dispenser nozzle 9 (FIG. 1) and into fluid port 22 (FIG. 5) and onto and through check valve 24 into fluid conduit line 28 and into T-Branch 31 and 32 onto fluid cavity 13 by ports 14 (FIG. 4) from lines 20 and 19 and equally into fluid conduit line 30 into check valve 26 and into piston chamber 11. The piston housing 11 is secured in dispenser's bottom half section 15 by retaining frame 16. The nozzle 9, the valve body assembly 12 are secured to the dispenser's bottom half section 15 by retaining frame 17.

Figure 1A:
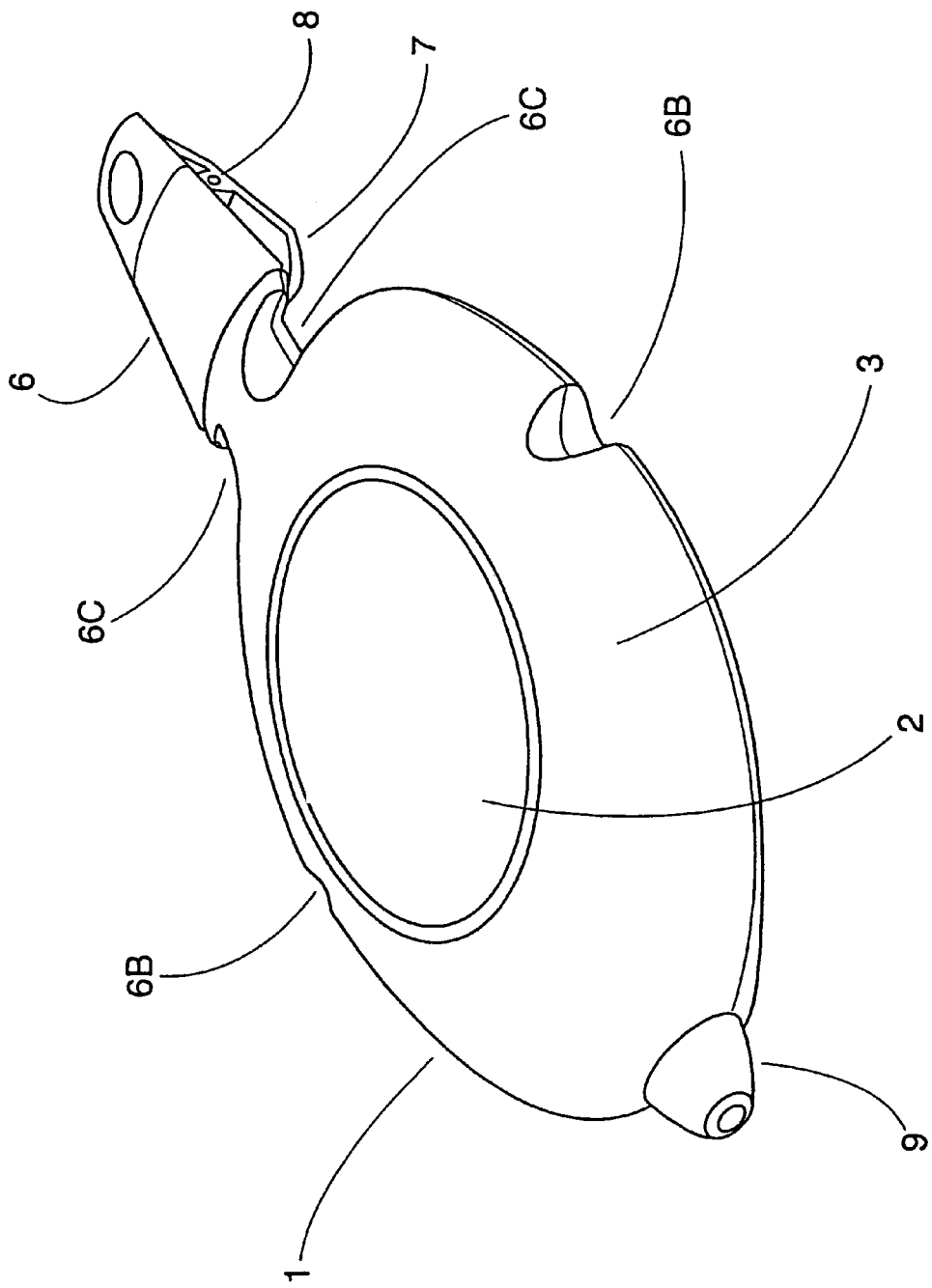
FIG. 1A is a top view perspective drawing of a dispenser embodiment having transport guide slots.

FIG. 1A represents an alternate embodiment of a dispenser with slightly different features for an alternate approach for its return and transport within a control station. In this particular embodiment, the dispenser has side guide relief notches 6B and tail relief guide notches 6C that provide alignment for uniform transport, by gravity, of said dispensers within a control station (FIG. 14) that has means to accept and uniformly transport said type of dispensers. In this embodiment, the tail extension is part of the housing bottom shell.

Figure 1B:
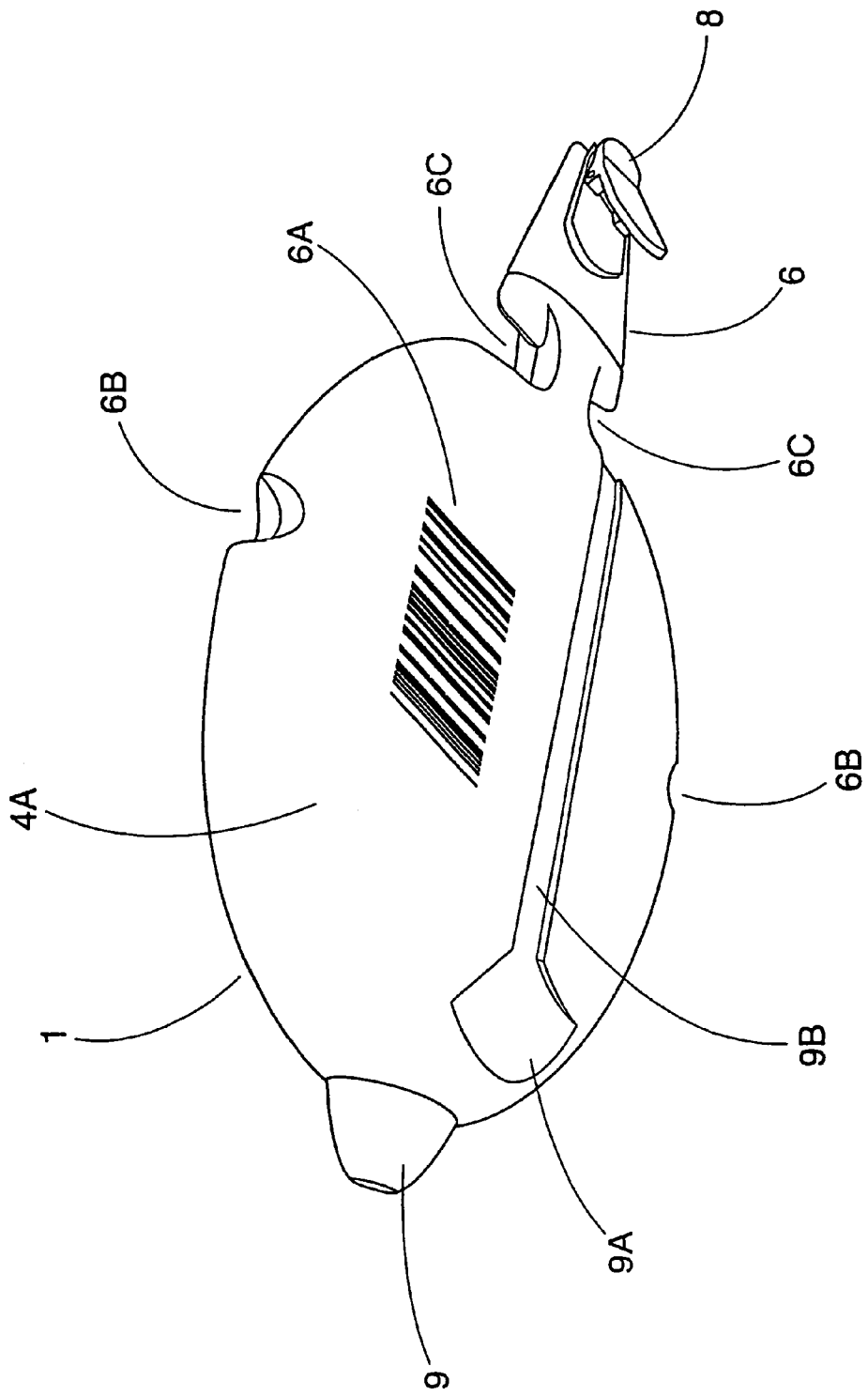
FIG. 1B is a bottom view perspective drawing of the dispenser embodiment having transport guide slots.

FIG. 1B shows the bottom of the notched dispenser of FIG. 1A, showing a tapered frontal relief entry type of area 9A that connects to a thru-relief alignment channel 9B which mates and guides said dispenser upon entry into a control station (FIG. 14) that has mating alignment means to accept said dispensers on top of said alignment means.

Figure 2:
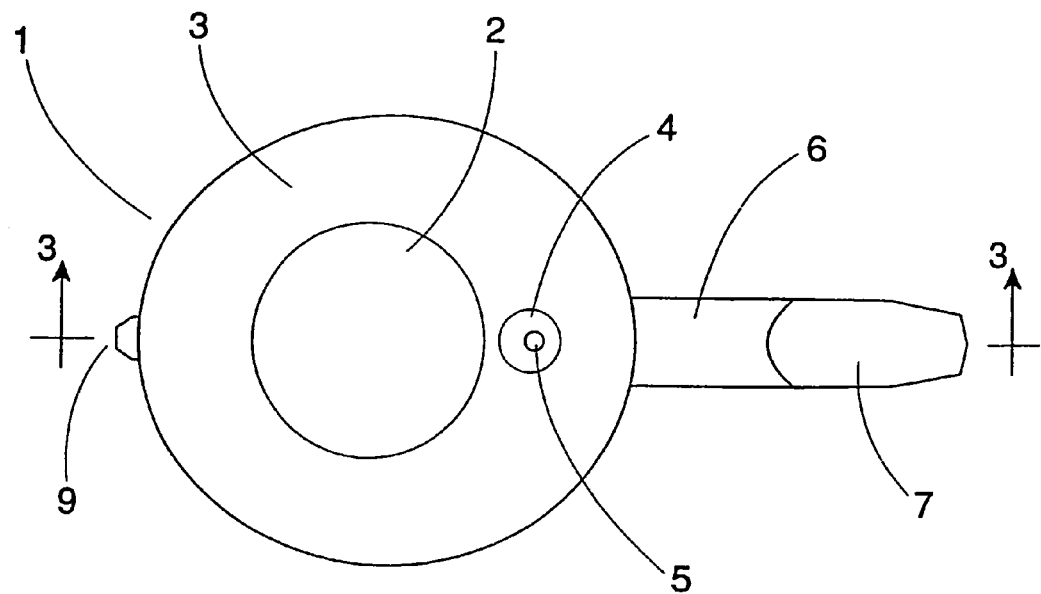
FIG. 2 is a top view drawing of the dispenser apparatus of FIG. 1.
Figure 2A:
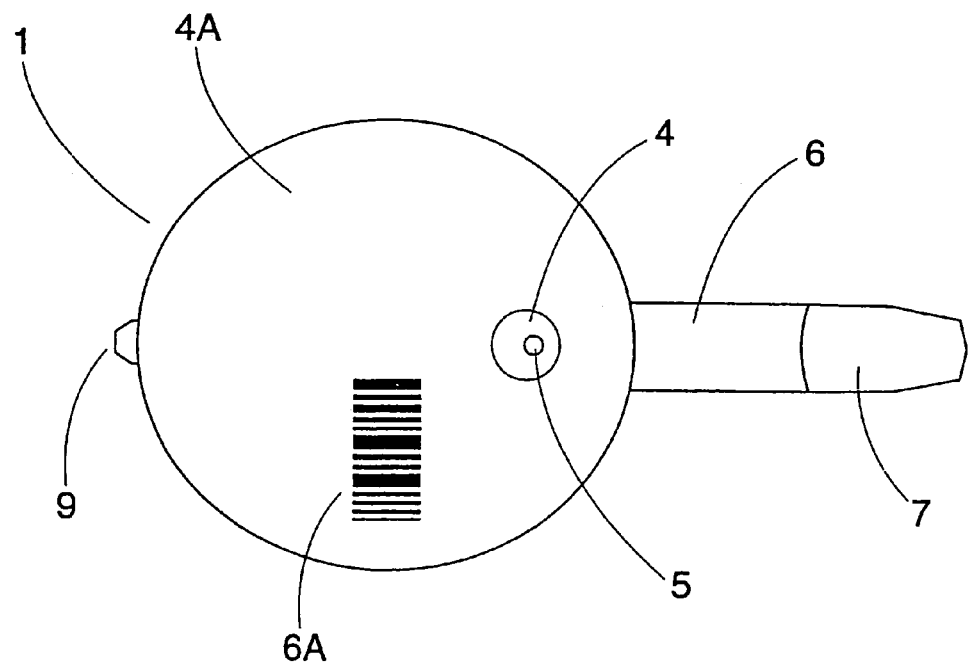
FIG. 2A is a bottom view drawing of the dispenser apparatus of FIG. 1.

Referring to FIG. 2, a top plan view of the FIG. 1 embodiment, it shows numbered elements 1-9 shown in FIG. 1. FIG. 2A shows the bottom of the FIG. 1 embodiment and shows a unique identifier in a bar code form 6A on the dispenser's bottom surface 4A. Other types and locations of identifier may be used. Magnetic, graduated color and/or shaded markings, optical/infrared reflectors, and mechanical tags are forms of some other types of systems. The identifier is unique in that it identifies a particular dispenser and distinguishes it from all others used at a health care, food service, technical clean room or other facility where hand cleaning is important.

Figure 3:
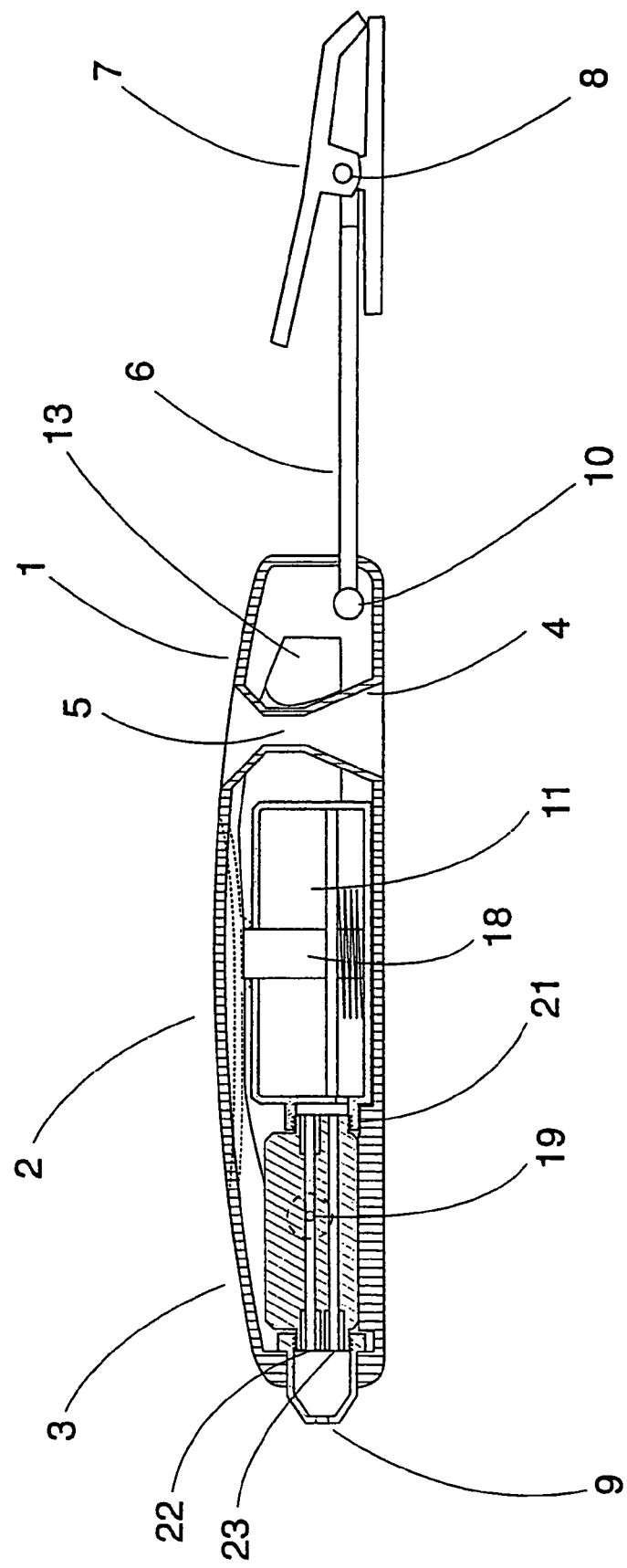
FIG. 3 is a cross sectional view taken at line 3-3 in FIG. 2 and viewed in the direction of the arrows.

FIG. 3 shows tail extension 6 of the FIG. 1 embodiment pivotally mounted to the dispenser by a universal hinge ball or other mounting at 10, facilitating use and direction of the nozzle without removal of the dispenser from the user's clothing. But, as indicated by the FIGS. 1A and 1B embodiment, this feature may not be needed, depending on where it is clipped to the user's clothing.

Figure 4:
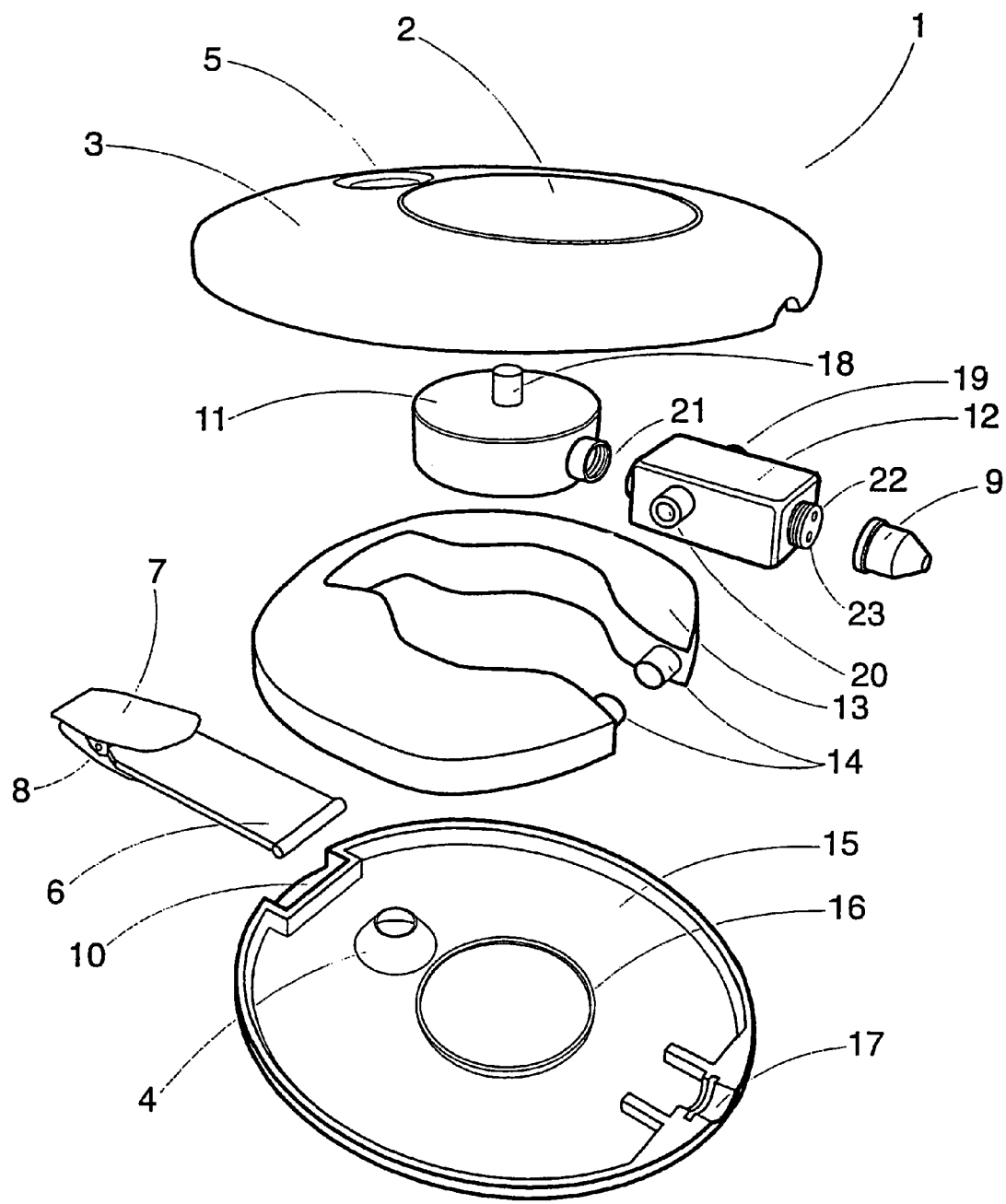
FIG. 4 is an exploded perspective view drawing of the dispenser apparatus of FIG. 1.

FIG. 4 shows dispenser 1, flexible fluid cavity 13 and wherein it is connected to fluid valve body assembly 12 by its mating coupler's 14 engagement to said fluid cavity 13 by left hand connector 20 and right hand connector 19. The fluid valve body assembly 12 is positioned into dispenser 1 at location 17. The valve body assembly 12 is connected to piston type pump 11 at location 21. The pump 11 further has an actuator 18 that is acted upon by dispenser's press pad 2. Piston pump 11 is positioned for attachment in dispenser 1 bottom section 15, at 16. Dispenser nozzle 9 for valve body assembly 12 is received on dispenser bottom section 15 at location 17. The valve body assembly 12 incorporates two forward mounted check valves 24 and 25 (FIG. 5).

Figure 5:
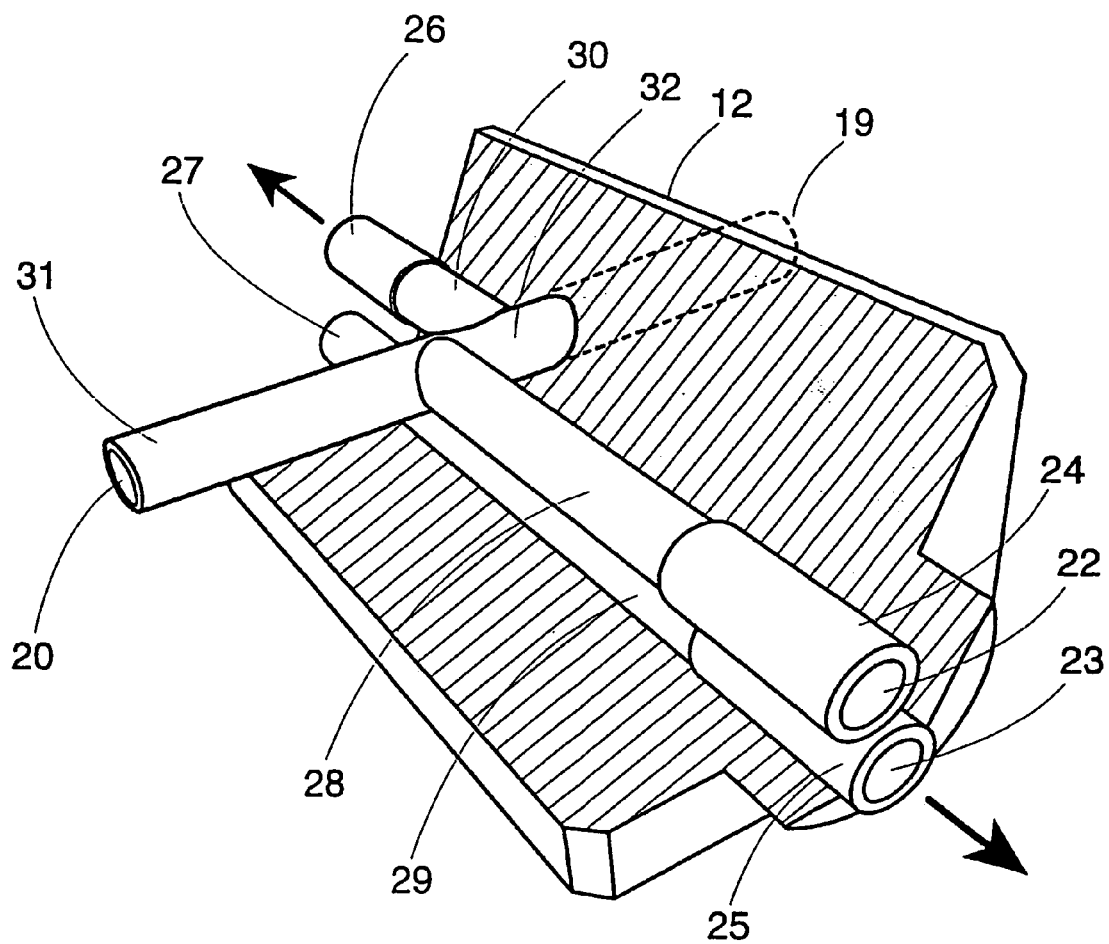
FIG. 5 is a perspective fragmentary view drawing of the dispenser apparatus fluid valve assembly.

FIG. 5 provides detail of valve body 12 by showing location of in-flow check valve 26 to piston pump 11 from its supply lines 31 and 32 which are connected to connectors 20 and 19 which are coupled to flexible fluid cavity 13 at mating points 14. Furthermore T-Branch lines 31 and 32 are connected to main incoming line 28 connected to main in-flow check valve 24 through entrance port 22 (FIG. 4). Outflow of fluid from piston pump 11 travels through port 27 into line 29 and through outflow check valve 25 through port 23 and out of the dispenser through nozzle 9.

Figure 6:
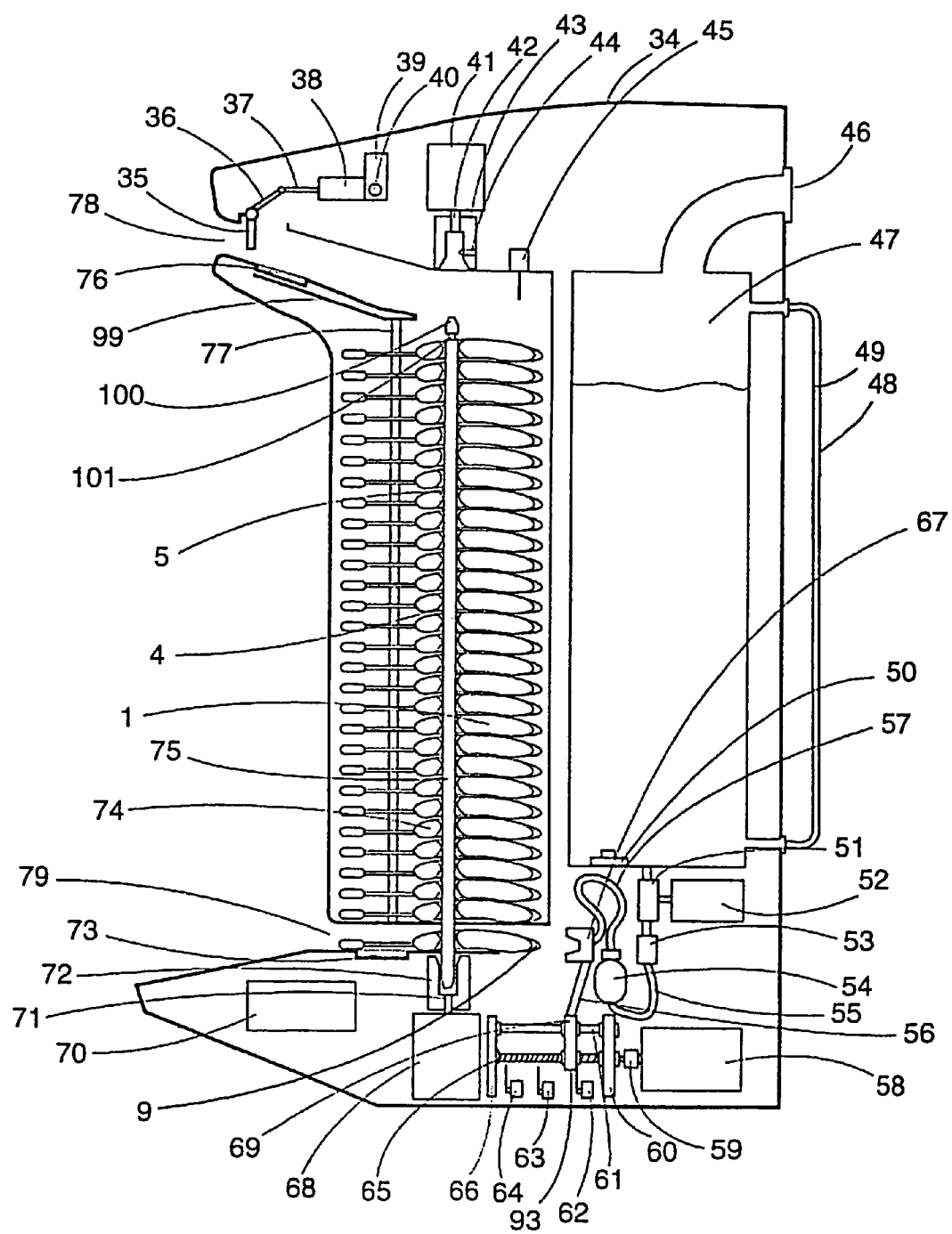
FIG. 6 is a vertical sectional view drawing of the control station apparatus.

FIG. 6 represents the control station apparatus 34 of the preferred embodiment of the present invention and comprises a dispenser check-in station near the top, and a dispenser check-out station near the bottom. At the illustrated check-in station, there is a returned dispenser entry slot 78 that has a restrictor gate 35 that is operated by a linear actuator 38. The actuator is connected to a fixed support bracket 39 which incorporates a pivot pin 40 which allows for the linear activator 38 to pivot upwardly and downwardly as the actuator rod 37 extends or retracts.

Operating arm 36 is fixed to gate 35 and is pivotally mounted to the station. It operates to open or close restrictor gate 35, being connected to the linear actuator's 38 push rod 37 by a pivot rod-end bearing. Returned dispensers are recorded by electronic reader 76 located in downward ramp 99 which is connected to dispenser travel guide 77. An example of the type of electronic reader used would be a ScanQuest IS4100 series made by Metrologic Instruments, Inc. of Blackwood, N.J.

The control station has a fluid reservoir 47 which has a fill spout 46 and a liquid level sight gauge 48 and empty indicator switch 50. Liquid level line of fluid in the reservoir and, of course, in the sight gauge, is represented by 49.

A dispenser transport rod 75 is vertically slidable in the control station between upper and lower stationary receptacles 43 and 72. The rod has a taper 100 located on the top and bottom for easy entrance alternately to top transport rod receptacle 43 and bottom transport rod receptacle 72. The top transport rod receptacle 43 comprises a spring-like assist to extend a pin or button or other engagement means 44 to mate with transport rod 75 detent 101. The top transport rod receptacle 43 has a linear actuator 41 that operates, through shaft 42, for disengagement of transport rod 75 from receptacle 43. The bottom transport rod receptacle 72 has a like linear actuator 68 that operates through shaft 71 to disengage transport rod 75. Referring to FIG. 3, the sloped or flared entry 4 and transport hole passageway 5 of the dispenser is typical of all dispensers shown in FIG. 6. It is received on the transport rod 75 when a dispenser has been admitted by gate 35 and traveled down ramp 99 by gravity to the top of the stack 74 of dispensers.

Figure 7:
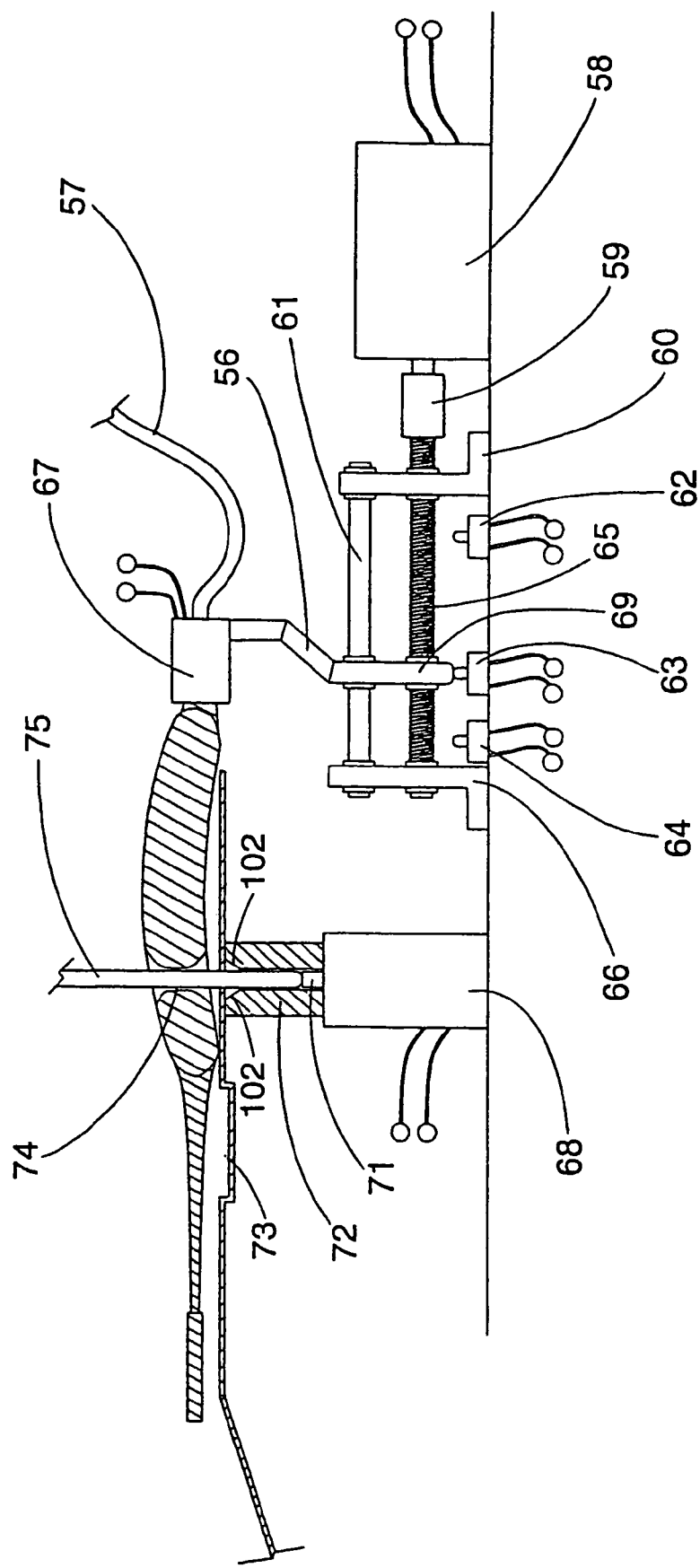
FIG. 7 is a side view drawing, partly in section, of the dispenser refilling apparatus of the control station apparatus of one embodiment of the present invention.

Referring to FIG. 7 along with FIG. 6, the illustrated fluid fill injection apparatus comprises pump 51, motor 52, fluid flow electronic reader 53, fluid conduit line 55, fluid pressure electronic reader 54, and fluid conduit line 57 to the dispenser filling fluid injection head 67. The model DFS-2W Flowmeter manufactured by Gator Process Specialties, Inc. located at P.O. Box 591, Bluebell, Pa., 19422 represents a type of fluid flow electronic reader usable herein. A Tem-Tech SE 3200 made by Net-Motion, Inc., located in Fremont, Calif. represents a type of fluid pressure electronic reader usable herein. Head 67 is mounted to a carriage arm 56 of transport carriage 69 which travels on a guide shaft 61 and is moved forwardly and rearwardly by drive shaft screw 65 which is powered by gear motor 58 through coupling 59 and mounted in the control station with typical bushing mounts shown at 60 and 66. The transport carriage 69 has three (3) function stop locations represented by electronic sensor switches 62, 63, 64. An example of the type of sensor useful would be a GL-6 miniature proximity sensor manufactured by SUNX Sensors, U.S.A. located at 1207 Maple, West Des Moines, Iowa., 50265. The position of the transport carriage 69 as shown in FIG. 6 represents the idle position 93. The nozzle of the lowermost dispenser in the stack is shown at 9. The electronic reader, which records a dispenser exiting the control station 34, is represented by 73 at dispenser retrieval slot 79 of the check-out station of the control station. An example of the type of electronic reader used would be a ScanQuest IS4100 series made by Metrologic Instruments, Inc., located in Blackwood, N.J. A processor with associated logic and memory and coupled to various signal inputs and outputs in the control station is represented by 70. Integrated circuit "chips", programmed or programmable to perform the various functions described herein, are preferred. But hard-wired, analog circuitry, or a conventional digital computer with programming, may be used. Various devices readily available off-the-shelf, or easily assembled with discrete off-the-shelf components by a technician can be used. Output to a conventional computer outside of the control station may be provided as an addition or an alternate to the on-board processing apparatus 70. Similarly, memory record display and printout on station 34 or on a separate device may be used.

The check-in station 34 has one or more obstruction detector switches 45 (The type of switch used to detect obstruction could be a GL-6 as previously described and made by SUNX Sensors). The switch or switches may be located as desired to sense any condition which would interfere with correct orientation of a returned dispenser, as the dispenser's rear (nozzle bearing) portion of the dispenser is a reference for the position of the dispenser housing opposite the transport rod 75 and the fluid refilling operating system.

FIG. 7 shows a side view of the fluid fill injection system apparatus in the dispenser refilling mode. The carriage 69 has been moved to location stop position 63 by the drive screw. The dispenser shown in the refilling mode is held in position by transport rod 75 when fluid fill head 67, supplied by fluid fill line 57, is driven to position engaging the dispenser nozzle 9 as shown. The bottom end of transport rod 75 is received in receptacle 72, with linear actuator 68 activating shaft 71 retracted so it is able to prevent the dispenser from being pushed out of place by the fill head.

Figure 8:
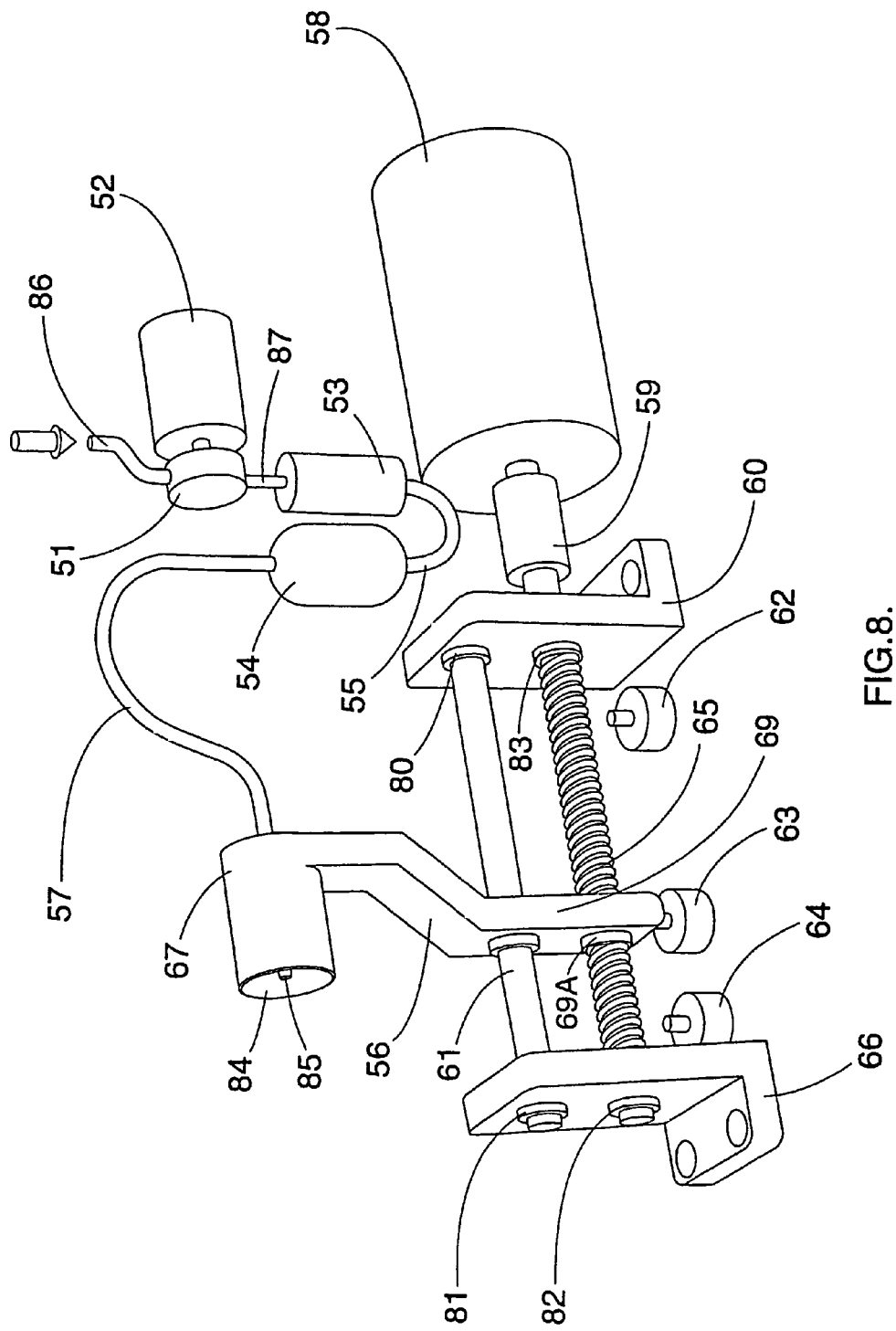
FIG. 8 is a perspective view drawing of the dispenser's fluid refilling apparatus.

FIG. 8 shows in perspective, the fluid pump 51, intake fluid line 86 from reservoir 47, pump motor 52, intake flow direction arrow, connector tube 87, fluid flow electronic reader 53, fluid conduit line 55 to fluid pressure electronic reader 54 and flexible fluid supply line 57 to fluid injection head 67. Carriage 69 is slidably supported by a guide bushing slidable on guide shaft 61 which is mounted at points 80 and 81 on carriage frame parts 60 and 66. Drive shaft 65 is rotatably mounted in bushing elements 82 and 83 and mating gear 69A fixed in carriage 69. Screw drive motor 58 is coupled by coupling 59 to drive shaft 65 which, during operation of motor 58, causes the carriage and thereby the fluid injection port carriage arm 56 to traverse to electronic stop positions 62, 63, and 64.

Figure 9:
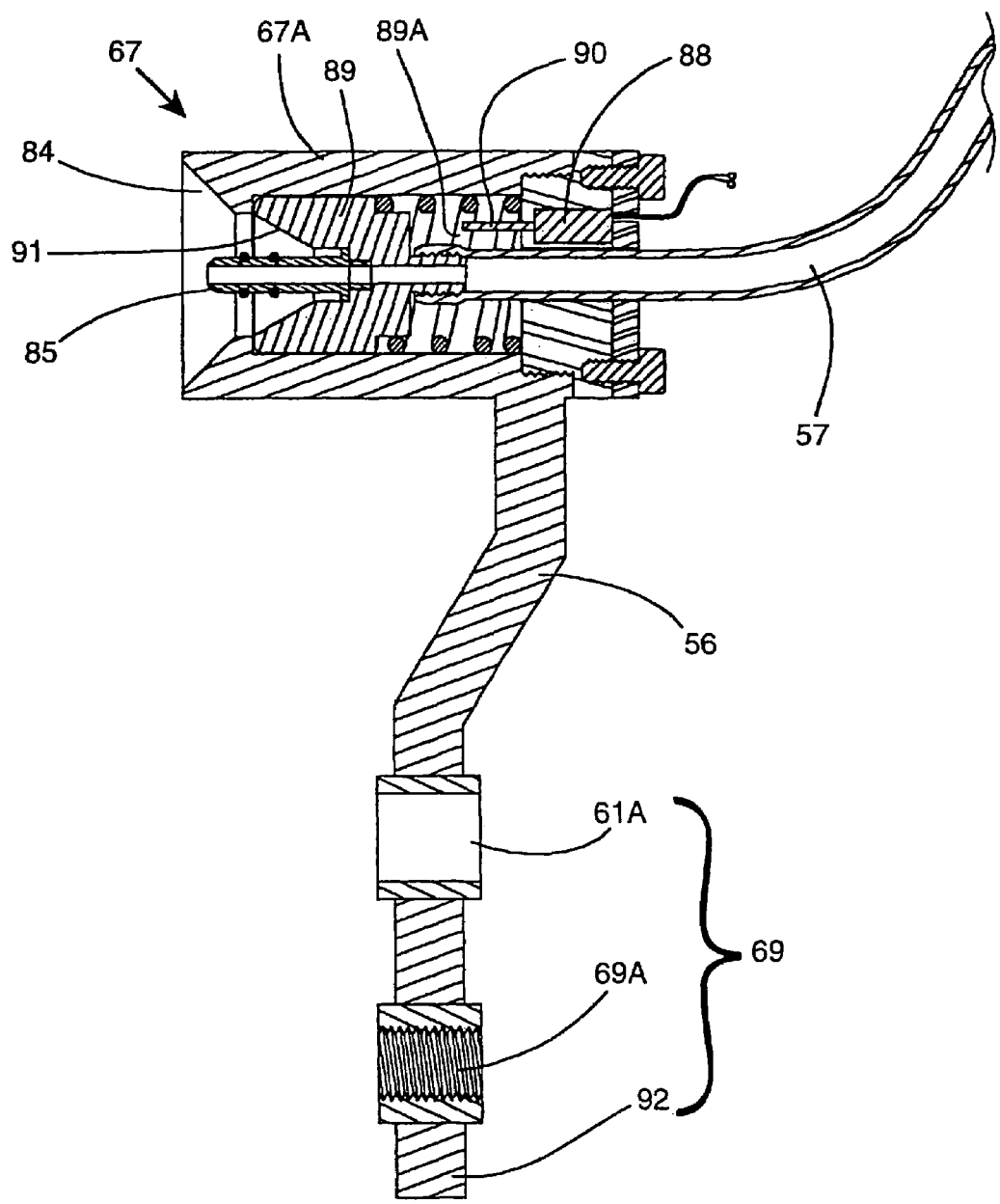
FIG. 9 is a cross-sectional drawing of the fluid refilling injection port apparatus.
Figure 10:
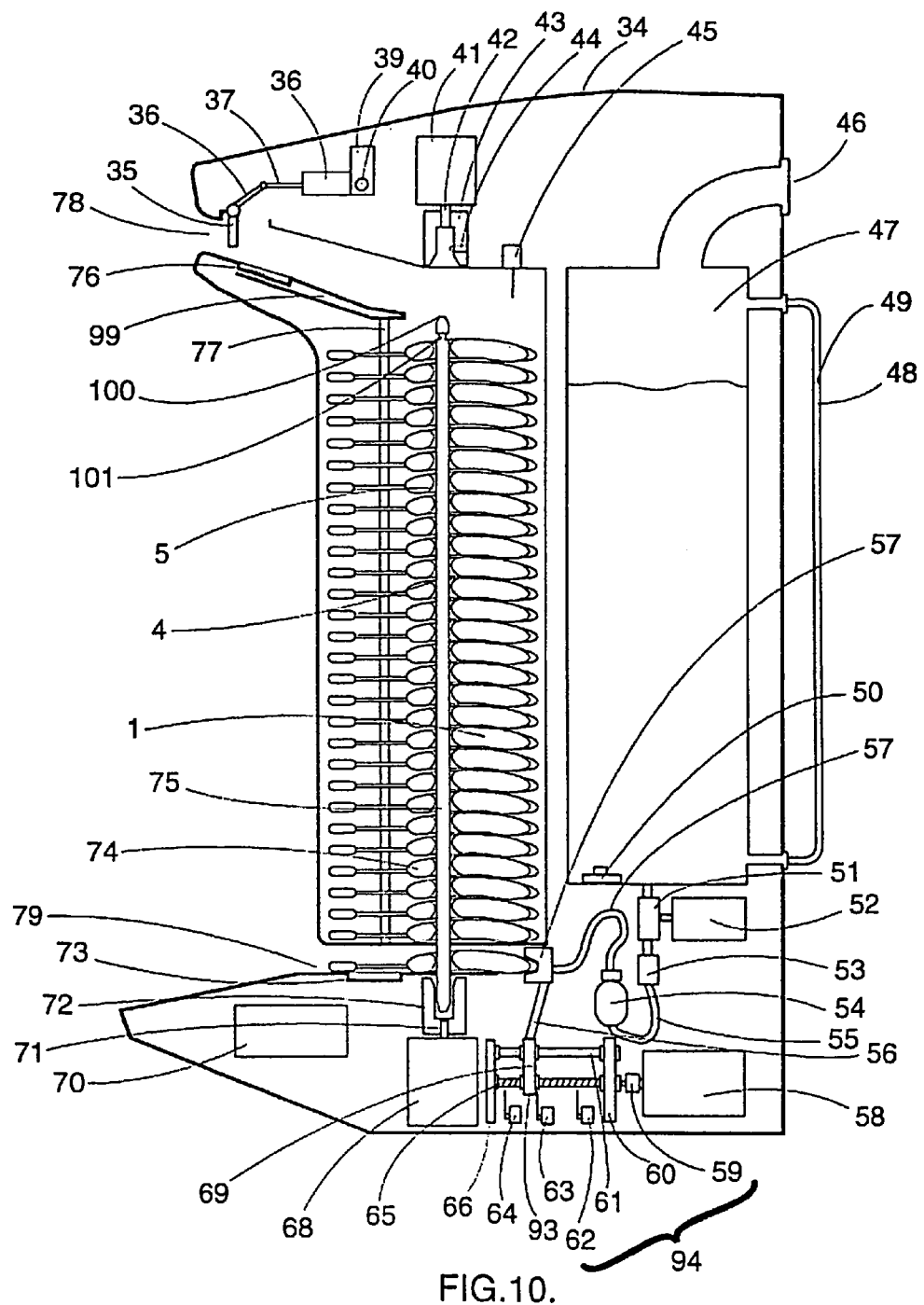
FIG. 10 is a vertical sectional view drawing of the control station apparatus, showing the fluid refilling injection port location at times of fluid refilling.

FIG. 9 represents a vertical sectional view of the fluid injection head assembly 67, comprising the flexible fluid line 57, fluid port housing 67A containing compression spring 89A and movable piston 89 which secures fluid pin 85. The fluid refilling pin's location within the dispenser's nozzle port prevents an occurrence of any fluid residual remaining on the dispenser's nozzle after the fluid refilling process. Piston 89 is shown in a rest position in housing 67A and is movable rearwardly against the spring load to a point where it will contact sensor arm 90 of sensor 88. Conical entry 84 of housing 67A transitions into conical entry 91 of piston 89. Pin 85 has a pair of O-rings for sealing inside dispenser nozzle 9 when coupled as in FIGS. 7 and 10 for filling. FIGS. 7 and 10 show the carriage portion 92 which activates the electronic sensor stops 62, 63 and 64.

Figure 11:
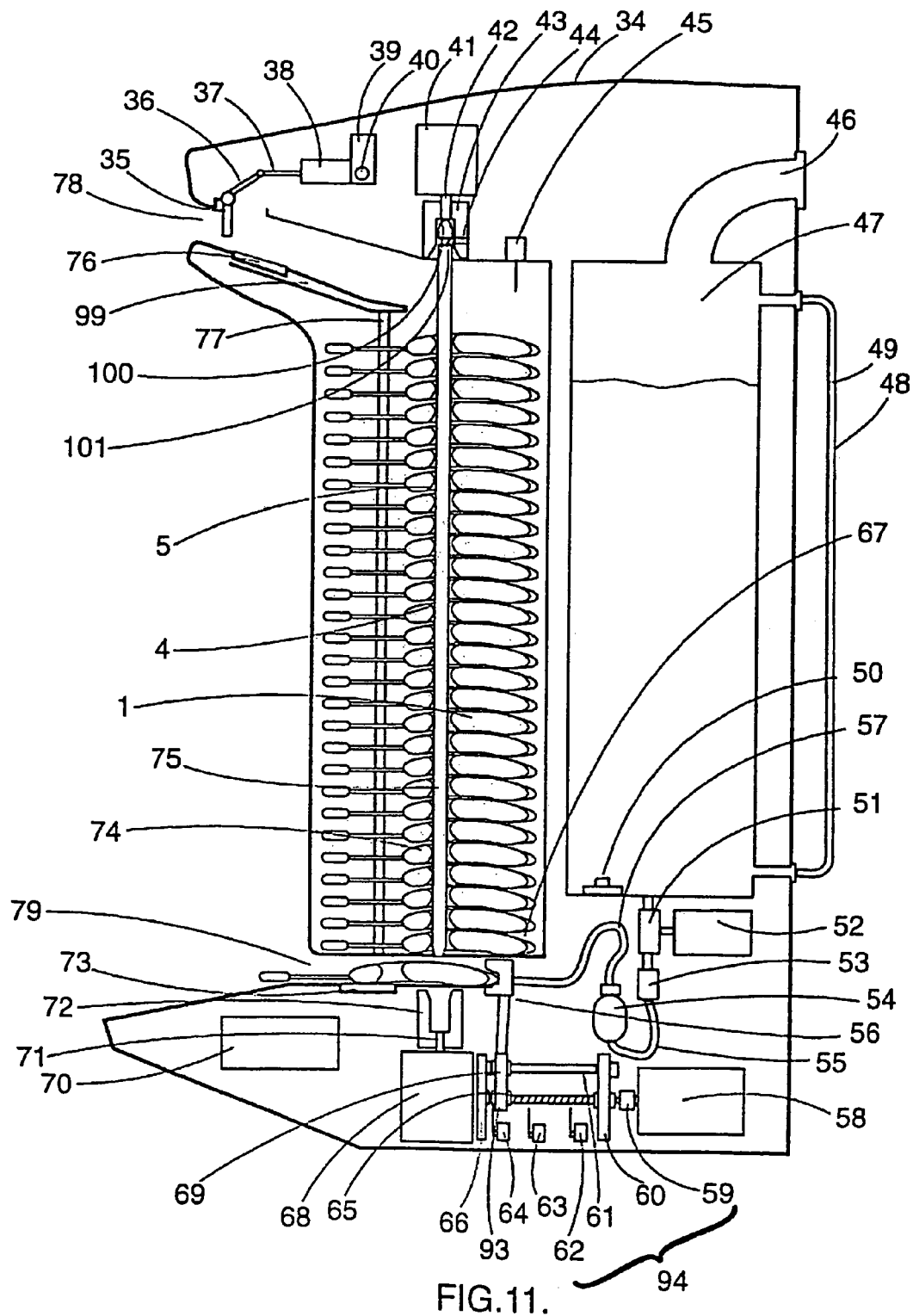
FIG. 11 is a vertical sectional view drawing of the control station apparatus, showing the fluid refilling injection port location at times of dispenser ejection from control station.

FIG. 11 shows the location of injection fluid head 67 in the position 95. As will be described, this follows extension of shaft 71 of linear activator 68 which has driven rod 75 upward out of receptacle 72 and into position in receptacle 43 where latched by detent pin 44 to disengage rod 75 from the lowermost, now filled, dispenser. That starts drive motor 58 and, when the activator arm portion 92 of carriage 69 has reached position activating electronic sensor 64, motor 58 is thereby turned off and the injection fluid head 67 has been driven to the left stop, ejecting the filled dispenser for retrieval by a user.

Figure 12:
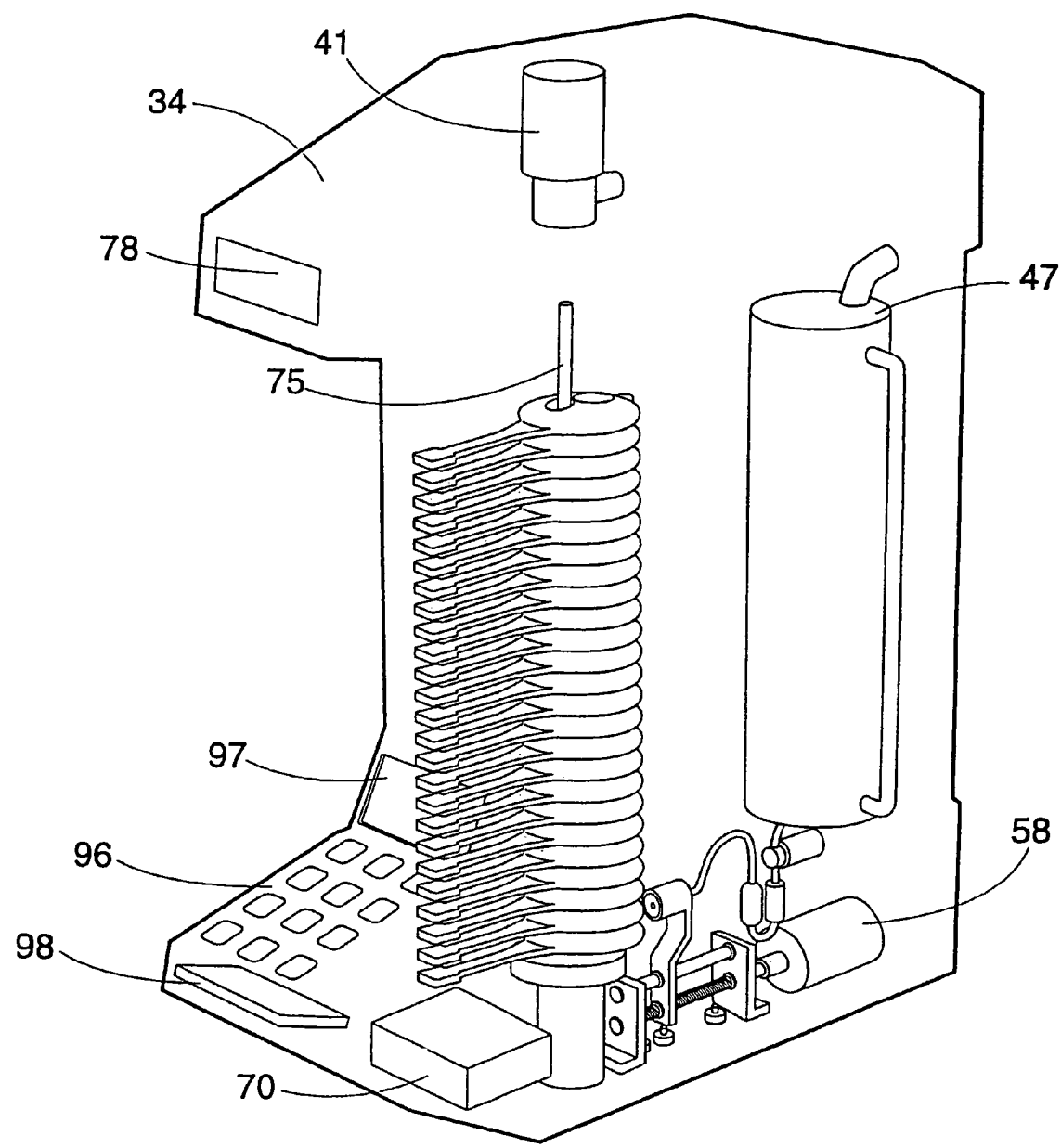
FIG. 12 is a perspective fragmentary view drawing of the control station apparatus of the present invention.

FIG. 12 shows in perspective view, the control station 34, the visual display 97, keypad entry 96 and electronic card reader 98 for recognizing the worker identifier when checking-out a dispenser. Of course, the keypad enables the worker to key-in their identifier, unique to that worker and none other, if they do not have their identifier card handy to use in a card swipe slot for reader 98, for example.

Figure 13:
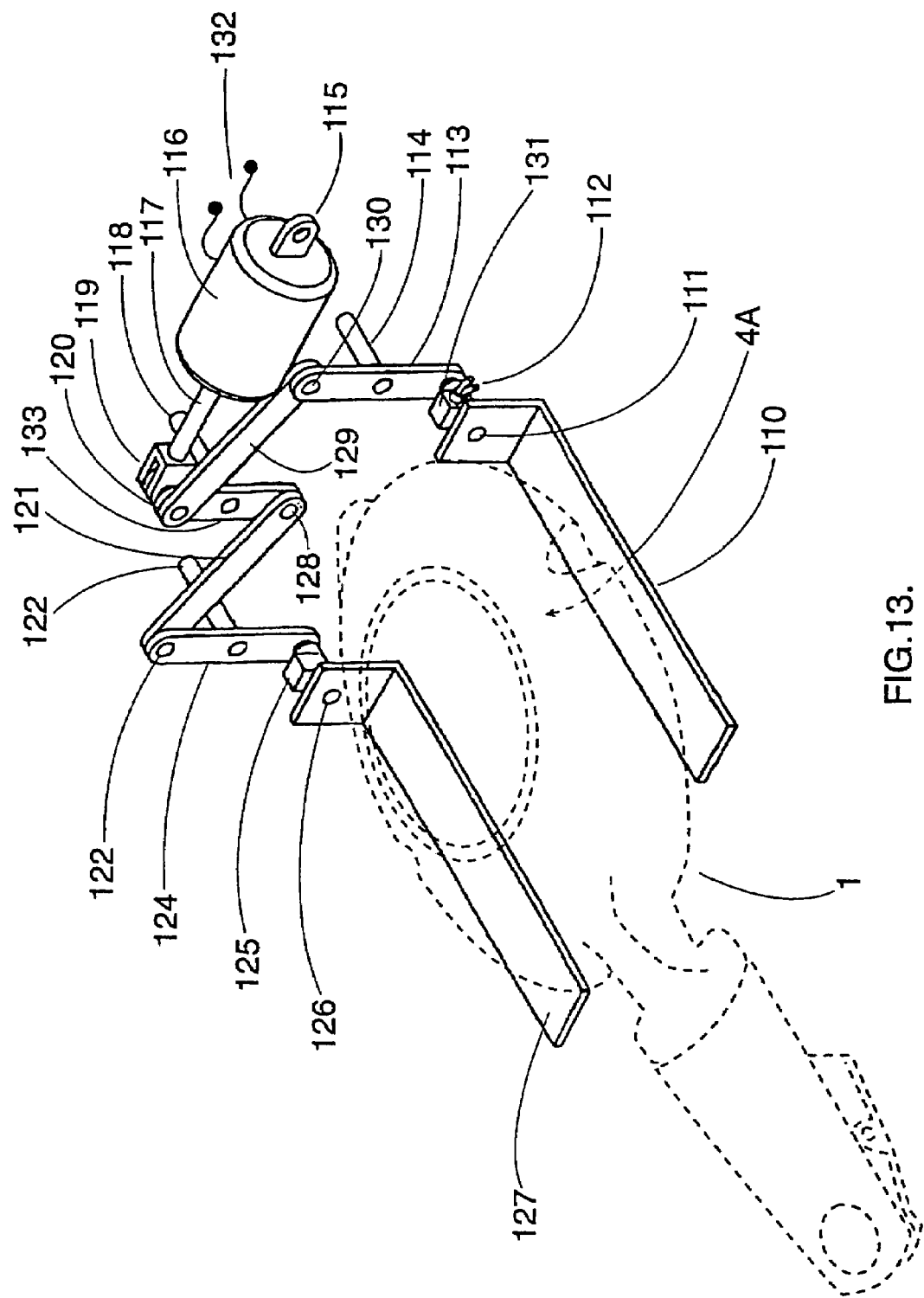
FIG. 13 is a top view perspective drawing of a dispenser weighing and recording apparatus.

FIG. 13 represents an embodiment of the present invention which has means to weigh a dispenser upon its return to a control station (FIG. 14) and then record the weight, for the processor 70 to calculate the amount of hand washing agent by weight dispensed by said dispenser during the time it was issued for use and its return after use to the control station. As a dispenser enters the return slot 78 of the control station, it travels by gravity down the inlet ramp 99, which may have a contour similar to that of the bottom of the dispenser for guidance, into a landing position on weighing apparatus (FIG. 13) by placement of its bottom section 4A (FIG. 2A) on weighing arms 110, 127. Once a dispenser is positioned for weighing on arms 110, 127 said arms rotate in a downwardly rotation which activates through pivots 111 & 126 rotary sensors 131, 125 (An example of the type of rotary position sensor used would be like model R30D made by Schaevitz Sensors located in Hampton, Va. 23666) which transmits through line 112 a signal to the computer processing memory 70 (FIG. 14) and which said signal is differentiated as to the amount of rotation said rotary sensor 131 rotates, thereby recording a unique weight measurement of a dispenser associated with that dispenser's unique identifier. Once a dispenser's weight has been recorded in the processor 70, the processor sends a signal through line 132 to the weighing apparatus linear actuator 116 which extends outwardly with piston arm 117 against pivot mount 119 which connects to lever arm 133 by pivot pin 120. Linear actuator 116 is pivotally mounted at 115. Lever arm 133 pivots about stationary pivot pin 118.

When lever arm 133 is pivoted outwardly (counterclockwise in FIG. 13), it causes right transfer linkage 129 to move inwardly (to the left) causing left transfer linkage 121 to move inwardly (to the right) by its pivot connection 128 to lever arm 133. When the right transfer linkage 129 is moved inwardly (to the left) and the left transfer linkage 121 is moved simultaneously inwardly (to the right), then the left vertical linkage arm 124 by its pivot connection 123 and the right vertical linkage arm 113 by its pivot connection 130 pivot outwardly about stationary pivots 114 and 122 respectfully causing the weighing arms 110 and 127 to rotate outwardly allowing the dispenser to drop into position for its travel downward within the control station.

A less than preferred means of measuring and recording a dispenser's previous fluid usage, would be for a dispenser's fluid reservoir to have two ports wherein one port provides entry of fluid to refill and the other (second) port acts as an exit port operable only upon the fluid refilling process of the dispenser.

An amount of fluid equal to a dispenser's reservoir capacity is inputted by the refill pump through one port into the dispenser's reservoir, whereupon any fluid existing within the returned after-use dispenser's reservoir exits the second reservoir port and is measured by its flow through an electronic flow reader. The fluid being measured travels back to the fluid holding tank within the control station.

Another means of measurement of the fluid content of a dispenser could include a means to optically read the fluid level content of a transparent and visible dispenser reservoir upon its return to the control station. Also possible is a dispenser which incorporates a mechanical indexing means wherein said indexing means is operable by its connection to a dispenser's actuator press pad and indexes to reveal a unique index position which correlates to the fluid volume that has been ejected from the dispenser and which is then mechanically read upon the dispenser's return to the control station.

Figure 14:
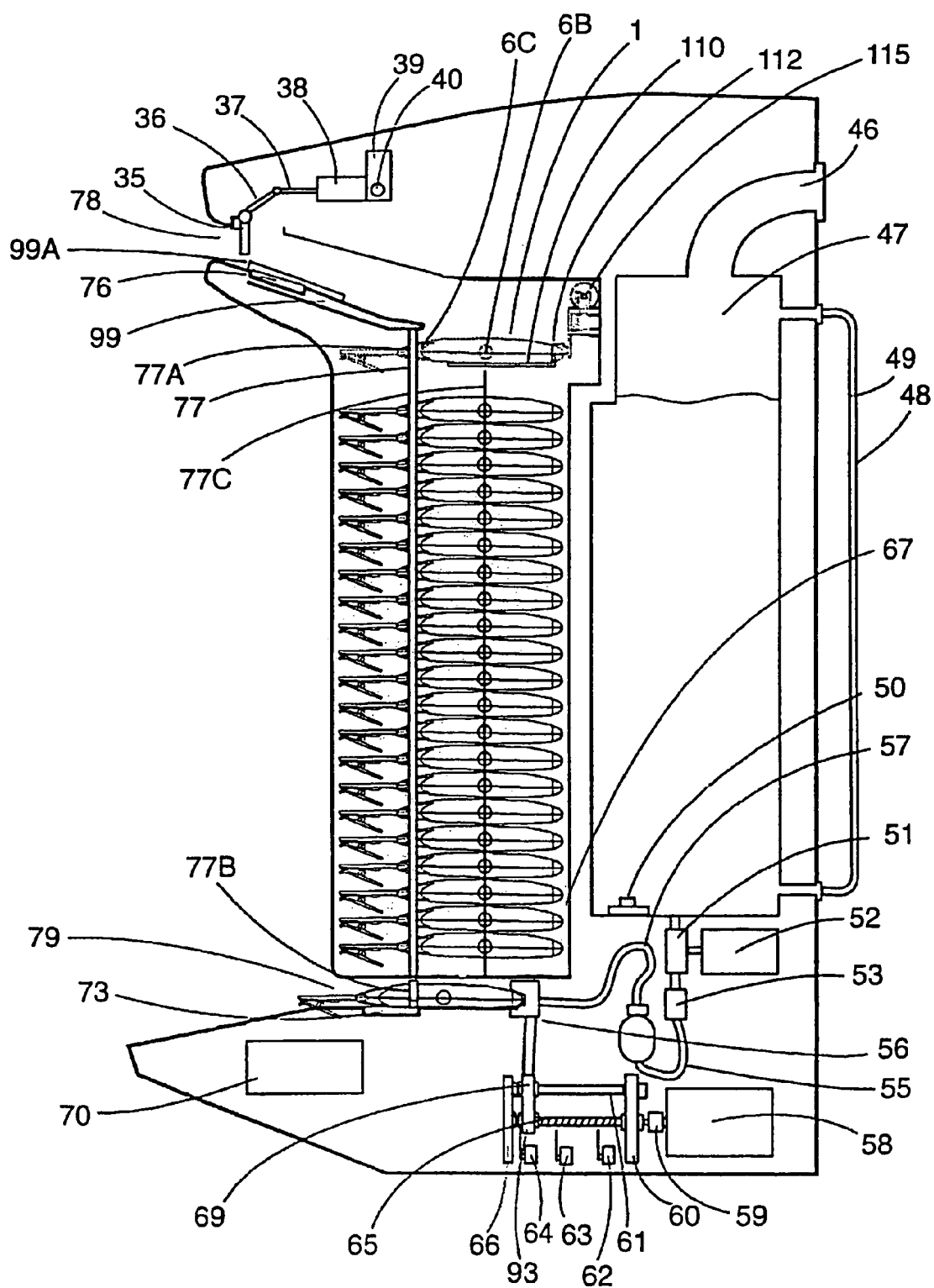
FIG. 14 is a vertical side section view drawing of a control station having a dispenser weighing and recording apparatus.

FIG. 14 represents the control station apparatus which processes a dispenser as viewed in FIG. 1A and FIG. 1B and which has previously been described. The dispenser side relief notches 6B mate with the control station side guides 77C upon the dispenser's entry into return slot 78 of the control station. These guides 77C are parallel. A guide extension for each of these guides 77C and which is not shown in FIG. 14, extends immediately below the bottom of the stationary guides 77C and is mounted atop a swivel arm which can be rotated about a vertical axis parallel to the guide 77C. This lower portion of the guide 77C is in position immediately directly below and in line with the stationary portions of these guides to hold the dispenser at the bottom of the stack while it is being filled by the pump. When filling has been completed, as detected by the pressure switch, the side guide extensions 77C are swung horizontally out of the way on their mounting arm pivot axis to prevent them from further holding the filled dispenser.

Thereupon, the dispenser can be ejected in the same manner as discussed briefly above and in more detail below, with reference to the figures previous to 13 and 14, when the transport guide rod 75 was raised for the release of the filled dispenser of the construction described regarding the first embodiment of FIG. 1. The dispenser's tail section guide notches 6C mate with the control station's tail guides 77 until said dispensers are received at the control station's dispenser refilling operation shown as 77B. Additionally, the check-in station as shown in FIG. 14 includes an extending guide rib 99A on ramp 99 that receives the FIG. 1B dispenser groove entry 9A upon a dispenser's entry into the control station's return slot 78 (FIG. 14) and assists the dispenser's accurate entry by its rib 99A continued guiding engagement with the dispenser's guide groove 9B as the dispenser travels down the ramp by gravity.

Operation, FIGS. 1-14

A person using the system and desiring to withdraw a dispenser, inputs authorization data incorporating their own identifier unique to that person and shared with no other person. The authorization input can be done at the keypad entry 96 (FIG. 12) or electronic card swipe for reader 98. Upon recognition of the user, the computer provides acceptance notification on visual display 97. The user entry data along with date and time data is recorded into processor 70.

Upon the user's successful data entry, the processor 70 (FIG. 11) signals the solenoid linear actuator 41 of rod top receptacle 43 to extend shaft 42, which pushes downwardly on retained transport rod 75, releasing its engagement from the spring-loaded pin 44 at transport rod 75 detent 101. Release of the transport rod 75 allows for it to travel downwardly by gravity in clearance holes 5 in the stack 74 of dispensers. This opens the space atop dispenser stack 74 to enable a returned dispenser to slide off the lower end of ramp 99 onto the top of the stack. Upon the arrival of lower end of transport rod 75 into engagement into the transport rod's bottom receptacle 72, it has now secured the bottom dispenser of stack 74 for a fluid filling operation. Thereupon a signal is transmitted to actuator 38 to open restrictor gate 35 to admit any dispenser being returned to the check-in station at that time. Also, a signal is transmitted to gear motor 58, which is activated to rotate drive shaft 65 which moves carriage 69 and thereby fluid injection head 67 until engagement of fluid injection head 67 is made with dispenser nozzle 9 (FIGS. 7 and 10).

Perhaps the agent dispenser that is capable of being refilled remains the most important measurable compliance of the invention's means to provide a hand cleaning network system within a hospital. The refillable operation of an agent dispenser records exactly a user's hand cleaning activity. The healthcare workers that would utilize a refillable agent dispenser would be those healthcare workers having contacts with patients who are within the intensive care or critical care units of a hospital. These patients sometimes have compromised immune systems and are more susceptible to nosocomial infections.

When fluid injection head 67 begins making contact with the dispenser nozzle 9 the conical entry 84 (FIG. 9) of the fluid injection head housing 67A correlates the dispenser nozzle 9 to accurately mate with conical entry 91 of piston 89, whereby fluid filling pin 85 securely enters and seals in dispenser nozzle 9. Upon the engagement of dispenser nozzle 9 to piston 89, the piston is pushed and travels rearwardly against a spring bias 89A until sensor arm 90 is compressed, causing an electrical signal to be transmitted by sensor 88 to gear motor 58 to deactivate the motor 58 (FIG. 6). When gear motor 58 deactivates, a signal is then transmitted to motor 52 (FIG. 6) to activate it, which operates fluid pump 51 to draw fluid from fluid reservoir 47 through line 86 (FIG. 8) to and through fluid flow electronic reader 53 and on by fluid line 55 to fluid pressure electronic reader 54 and then in final connection through flexible fluid line 57 to fluid injection head housing 67A.

Fluid from reservoir 47 will be pumped by pump 51 into dispenser fluid cavity 13 (FIG. 4) until a back flow pressure is sensed by fluid pressure electronic reader 54 at a predetermined value, such as approximately 15 PSI, for example. At that time a recording into the computer memory 70 is made of said pressure reading by fluid pressure electronic reader 54 along with the recording of the amount of fluid which has flowed through the fluid flow electronic reader 53. This procedure has now recorded the amount of fluid used to refill an individual dispenser.

When the fluid pump 51 is deactivated by the pressure reader 54, the gear motor 58 activates in reverse briefly until spring 89A returns piston 89 (FIG. 9) to its forward position, deactivating electrical sensor arm 90 and thereby sensor 88, which deactivates gear motor 58. Dispenser nozzle 9 is still in contact with the injection head 67, but without hydraulic pressure tending to abruptly separate them.

Also, when the fluid pump 51 is deactivated, a signal is transmitted to the transport rod's bottom receptacle 72 solenoid linear actuator 68 to activate and extend shaft 71 upward, pushing dispenser transport rod 75 up and out of its engagement with the filled dispenser until its (75) tapered upper end 100 enters into the transport rod top receptacle 43 and into engagement by spring-loaded detent pin 44 which enters and holds transport rod 75 in relief detent 101. Solenoid shaft 71 then retracts.

When transport rod 75 has been engaged to transport rod top receptacle 43, a signal is transmitted to linear actuator 38 which is pivotally mounted by 39 and 40 to activate and extend through linkage 36 and 37 to close, in the down position, pivoting gate 35. Concurrently, a signal is also transmitted to the gear motor 58 which powers driveshaft 65 to move carriage 69 and its fluid injection head 67, which is in contact with the dispenser 1 at nozzle 9 location, and moves said dispenser forwardly (FIG. 11) and into retrieval slot 79 for user retrieval. When carriage arm 92 (FIG. 9) triggers electrical sensor 64 (FIG. 6), said sensor 64 transmits a signal to gear motor 58 to activate it to power the driveshaft 65 to reverse the direction of carriage 69 until it (69) travels to where carriage arm 92 activates electrical stop sensor 62, representing the idle position shown as 93 (FIG. 6) of the carriage 69.

When the dispenser 1 is retrieved from retrieval slot 79 (FIG. 6), an electrical reader 73 reads and records the dispenser's 1 unique identifier 6A located on bottom surface 4A of dispenser 1 (FIG. 2A) and inputs data along with date and time and the fluid fill amount data into processor 70.

Additionally, when a dispenser 1 is retrieved and its unique identifier 6A passes over electronic reader 73, a signal is transmitted to the transport rod top receptacle 43 to cause solenoid linear actuator 41 to extend shaft 42 to push transport rod 75 from detented engagement to allow it to drop by gravity into secure engagement with transport rod bottom receptacle 72. Alignment and assist for transport rod 75 to enter receptacles is provided by receptacle entrance tapers or cones 102 (FIG. 7).

When transport rod 75 is in engagement with bottom receptacle 72, a signal is transmitted to restrictor gate 35 linear actuator 38 to activate and retract, which causes restrictor gate to pivot up and into an open position to receive any returned after-use dispensers for the top of stack 74. It should be noted that the transport rod 75 is always in contact with either the transport rod's top receptacle 43 or the transport rod's bottom receptacle 72.

When a dispenser is returned by its user to the control station 34 return entry slot 78, it passes through restrictor gate 35 that opens if system is in the dispenser return mode as previously described. As the dispenser is admitted, it passes over the return dispenser electronic reader 76, which reads and records in the computer, along with date and time data, the dispenser's unique identifier tag 6A which is located on the dispenser's bottom surface 4A (FIG. 2A). The identifier is preferably located on the bottom of a dispenser, as shown. A side or, less desirably, top or other location might be used, with comparable relocation of readers in the control station.

The dispenser travels downwardly by gravity on ramp 99, which is contoured similar to the dispenser's shape and which leads and guides said dispenser to a location where the transport rod 75 can enter the dispenser from its bottom surface's 4A sloped entry 4 and hole 5 (FIG. 1), facilitated by the transport rod's tapered upper end 100.

Dispensers 74 are transported within transport chamber by their downward gravitational freedom of movement. Also, within the transport chamber is a dispenser tail extension 6 (FIG. 1) guide comprising a pair of horizontally-spaced, parallel vertical rails 77 (FIG. 6) to facilitate proper dispenser orientation during transport.

Electric switch 45 (FIG. 6) acts as a transmitter to indicate a disoriented or lodged dispenser situation, which activates restrictor gate 35 to close and the visual display 97 (FIG. 12) to be activated, indicating a jam.

Having described the dispenser, the control station, and the use of both, and the operation of the system, it is considered well within the skill of the art to provide the control circuitry and off-the-shelf components to implement the system.

As has been previously described, the present invention's preferred embodiment comprises an apparatus and method to issue a report from data that has been collected and processed by the control station 34 computer memory processor 70 during the procedural operation of issuing hand dispensers for use and retrieving dispensers after-use and which said report will include:

date and time a specific dispenser by that dispenser's unique identifier is issued to what user by that user's unique identifier date and time a specific dispenser by that dispenser's unique identifier is returned after-use by what user by that user's unique identifier How many (quantity) of dispensing applications occurred by a specific dispenser and its specific user during what time frame.

For an embodiment of the present invention in which weighing of a dispenser is used to determine the quantity of fluid used, the weighing scale can be located at the lower end of the entrance ramp as shown, for example, in the embodiment of FIG. 14. In this case, a standard dispenser that is full of fluid can be used for one reference point, and an identical or the same dispenser empty can be used as the other reference point. Therefore, the assumption is that the dispenser which is returned for refilling is no different from that dispenser as it was when first released for use, except for the amount of fluid contained when filled. In other words, it is exactly the same dispenser when returned as it was when filled, so the only difference in weight is due to the amount of fluid that was dispensed. Accordingly, it is not necessary that the dispenser be weighed at the bottom of the control station following filling.

Refillable Dispenser for Exclusive Use of One User

In an alternate embodiment of the system using some aspects of the present invention, each worker would have a single dispenser assigned to him or her on a permanent basis. In that case, that worker, who would still have a unique personal identifier and would enter their identification into the control station in the same manner as described above, using a keypad or an identifier card or tag of some sort. Upon recognition by the processor, the worker can obtain admission of their personal dispenser through the entry gate 35 following which the dispenser slides down the ramp 99 onto the control rod 75 or between the side guide 77C (depending upon the type of dispenser). In this scenario, there is no stack of other dispensers in the control station, so the returned dispenser immediately descends to the fill location. The filling function is accomplished, following which the pressure sensor signals the drive motor 58 to back off slightly to release pressure, whereupon sensor 63 can initiate drive motor 58 to drive the dispenser forward out the slot 79 for the worker to retrieve. In this scenario, the readers 76 and 73 are not needed, as the usage of material by the dispenser inserted and retrieved by the worker is immediately available and recorded in the processor along with that user's unique identifier.

For purposes of example, the capacity of the agent storage reservoir in the dispenser may be 10 to 75 milliliters (ml.).

The preferred amount of agent dispensed per press of the pad 2 is 0.5 to 3.0 ml. As an example of dimensions, the overall length of the dispenser from the tip of nozzle 9 at the front end, through the clip at the rear end of the tail extension, is preferably about 5.5 inches (15 cm.). The body portion from the nozzle tip to the tail extension is about 3 inches (7.6 cm.) long, and the tail extension is about 2.5 inches (6.4 cm.) long. The overall width is preferably less than 3.125 inches (18 cm.). The diameter of the press pad is preferably about 2 inches (5.1 cm.). The overall weight of the dispenser assembly when filled with the hand cleaning agent is preferably between 1 and 5 ounces. The clip is preferably connected to the worker's clothing at a location about 3 inches above the waist, and about half the distance to the left or right from the sternum to the outside of the rib cage. With the dispenser hanging from the outside of the worker's clothing, with the hanger clip at the top and the nozzle at the bottom pointing downward, the nozzle will never be at rest above the point of connection to the worker's clothing. This makes it convenient for the worker to grasp the dispenser with one hand and easily orient it to press the pad with a thumb or a couple of fingers of the one hand, and dispense from the nozzle outward toward the other hand in any convenient direction. There is no need to lift the dispenser (such as taking a spray bottle out of a pocket) or to re-orient a tube or bottle to point the tube or bottle nozzle toward the other hand.

Single Agent Compartment Replaceable Cartridge

Figure 15:
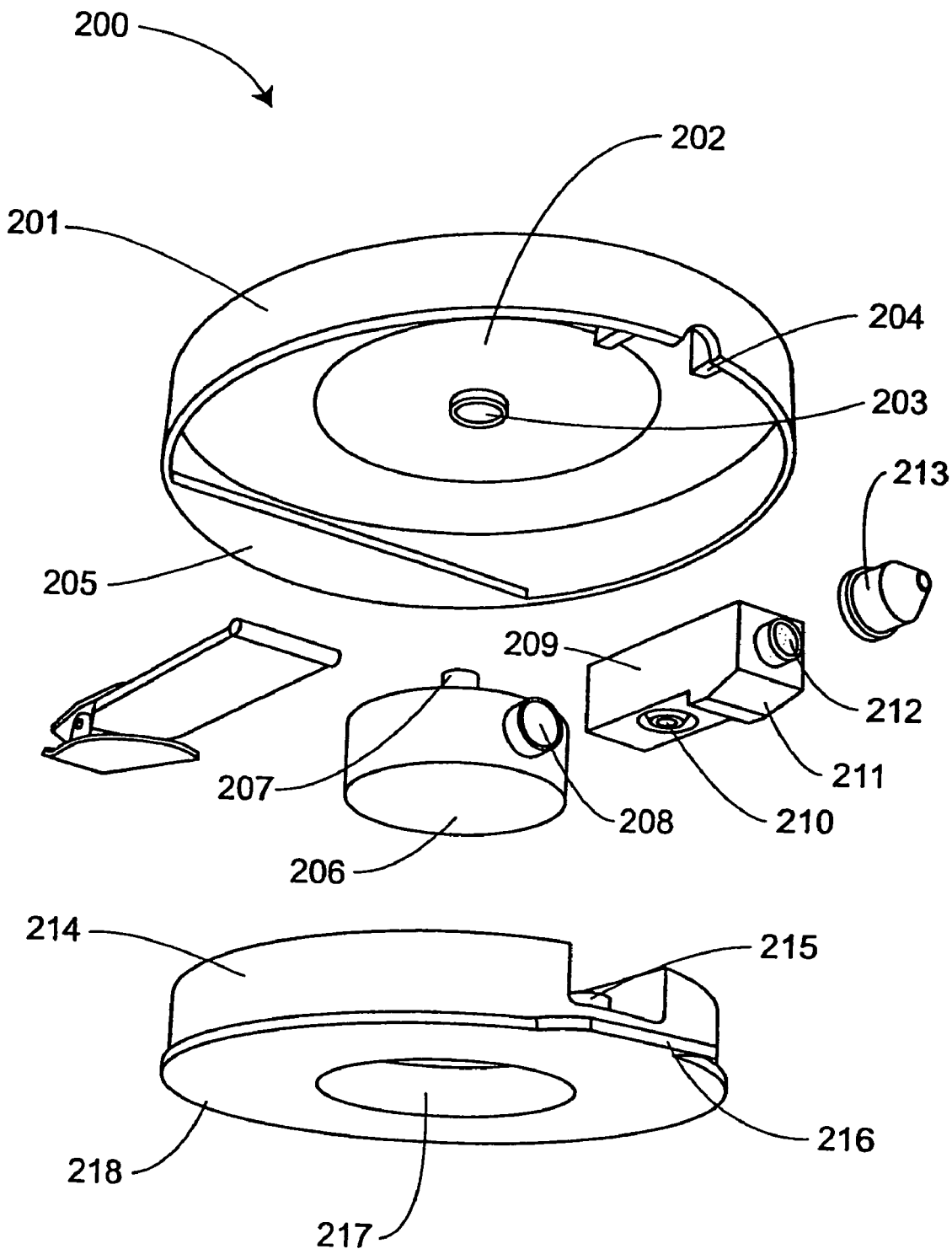
FIG. 15 is a bottom view exploded view drawing of another embodiment of the present invention agent dispenser showing a replaceable agent cartridge.

Referring to FIG. 15, dispenser 200 uses a replaceable agent cartridge 214 in top housing 201 which has a rear retainer frame 205 which captures agent cartridge bottom surface 218. The agent dispenser 200 has an agent discharge pump 206 which is connected through activator pin 207 to operator press pad 202 by connection 203. The agent pump 206 is connected to valve body assembly 209 through port 208. Valve body assembly 209 contains an inlet port 210 to receive agent from agent cartridge 214 through its port 215. The valve body assembly 209 further comprises a nozzle port 212, a nozzle 213 and a sloped area 211 to receive cartridge 214 removing tab 216. Dispenser 200 top housing 201 has a retainer frame 204 wherein nozzle 212 and valve assembly body 209 are secured. Cartridge 214 has a central aperture 217 which, when in its operating position, surrounds the dispenser pump 206

Figure 16:
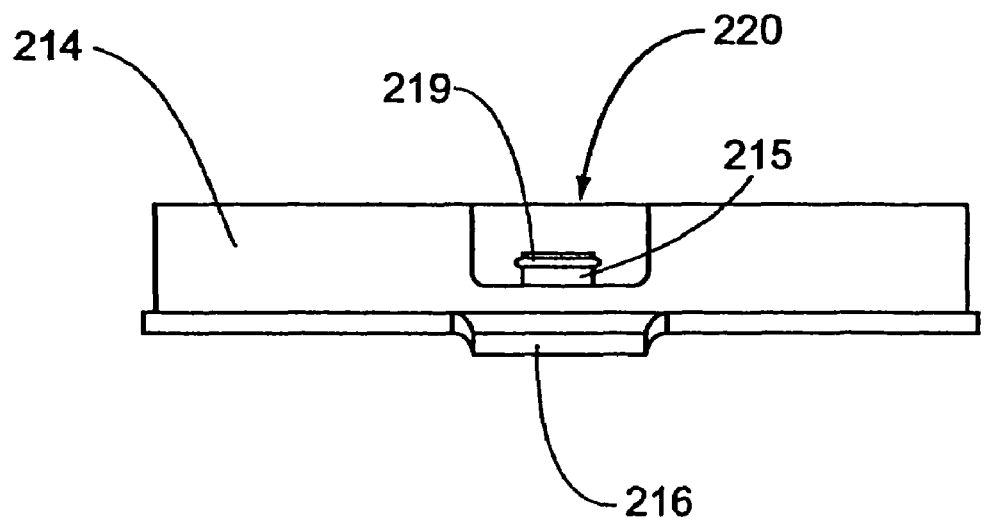
FIG. 16 is a front view drawing showing a replaceable agent cartridge.
Figure 17:
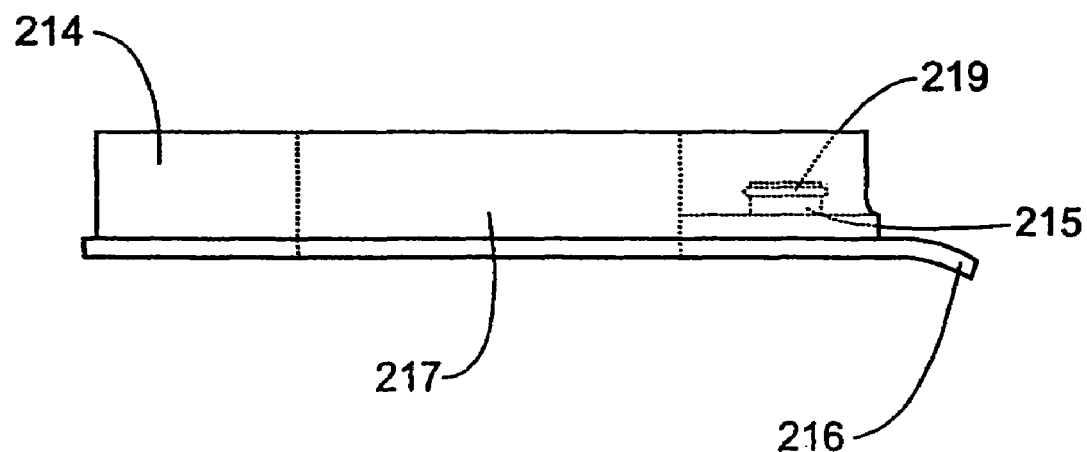
FIG. 17 is a side view drawing showing a replaceable agent cartridge.
Figure 17A:
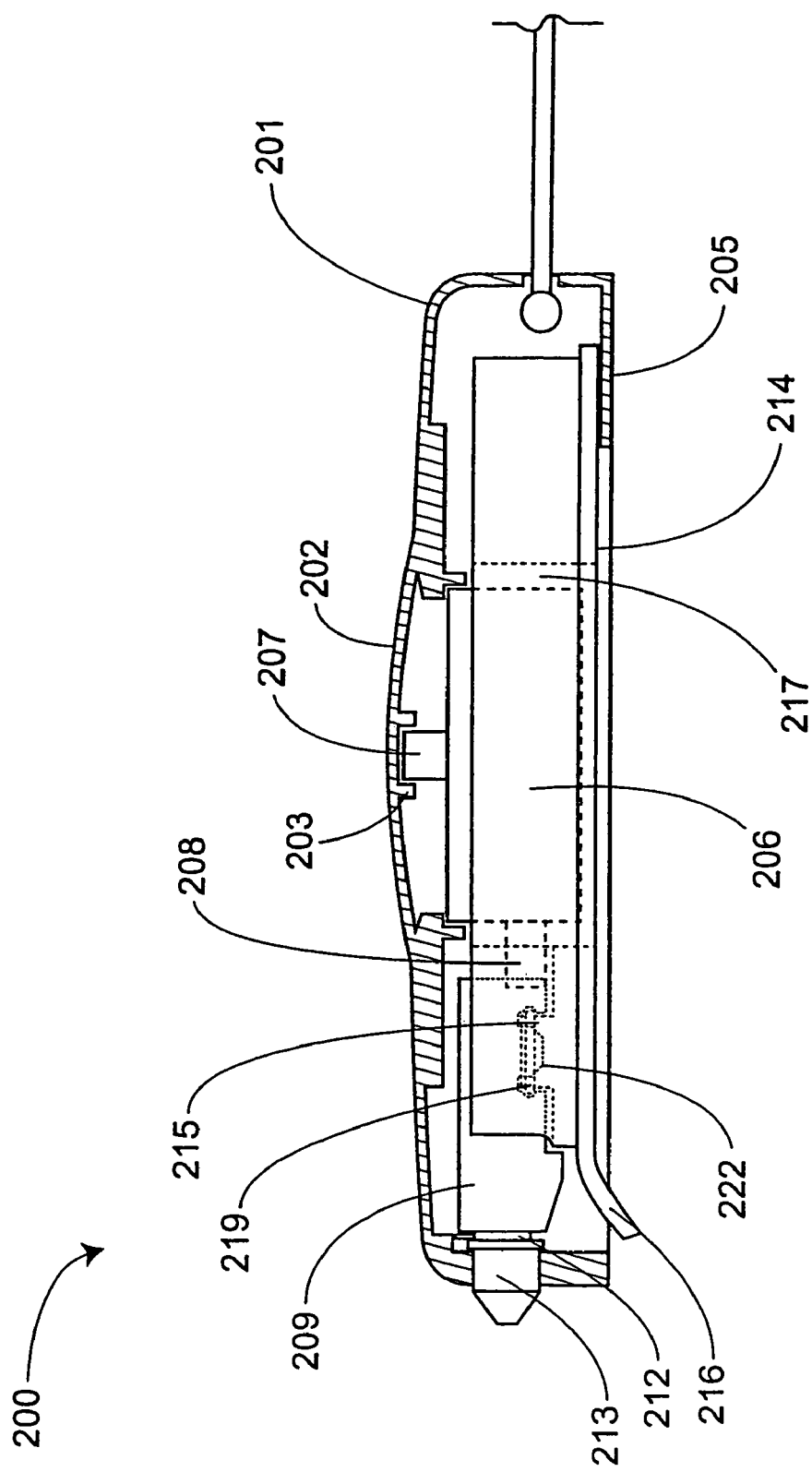
FIG. 17A is a vertical section through the dispenser housing and showing a replaceable agent cartridge in place.
Figure 18:
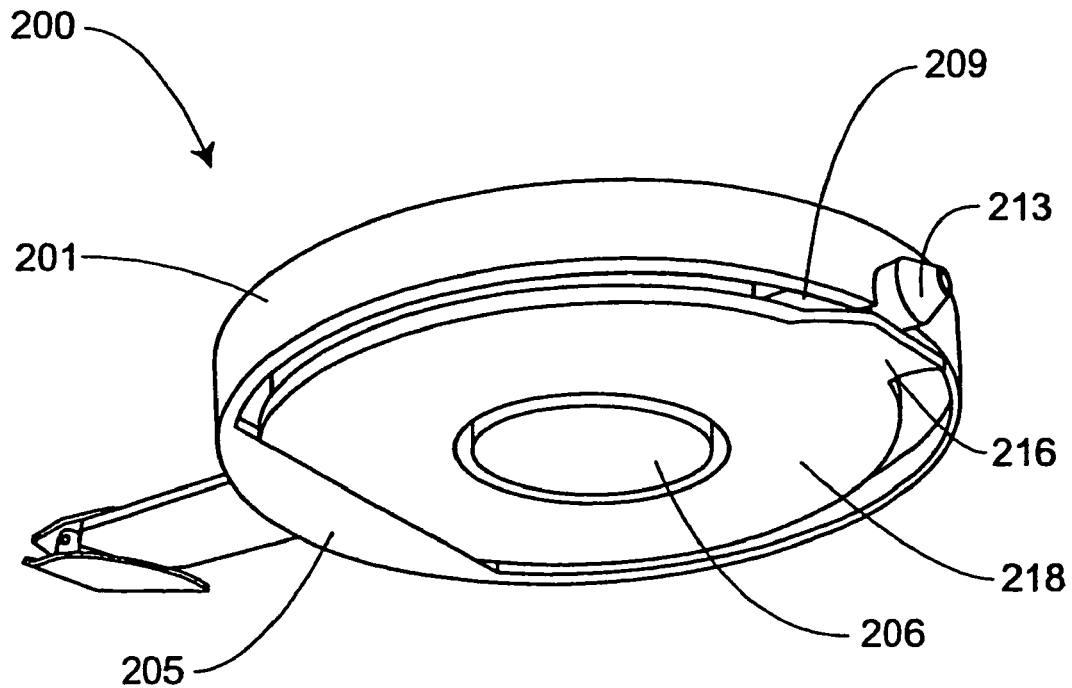
FIG. 18 is a bottom view perspective drawing showing an agent dispenser containing an agent cartridge.
Figure 19:
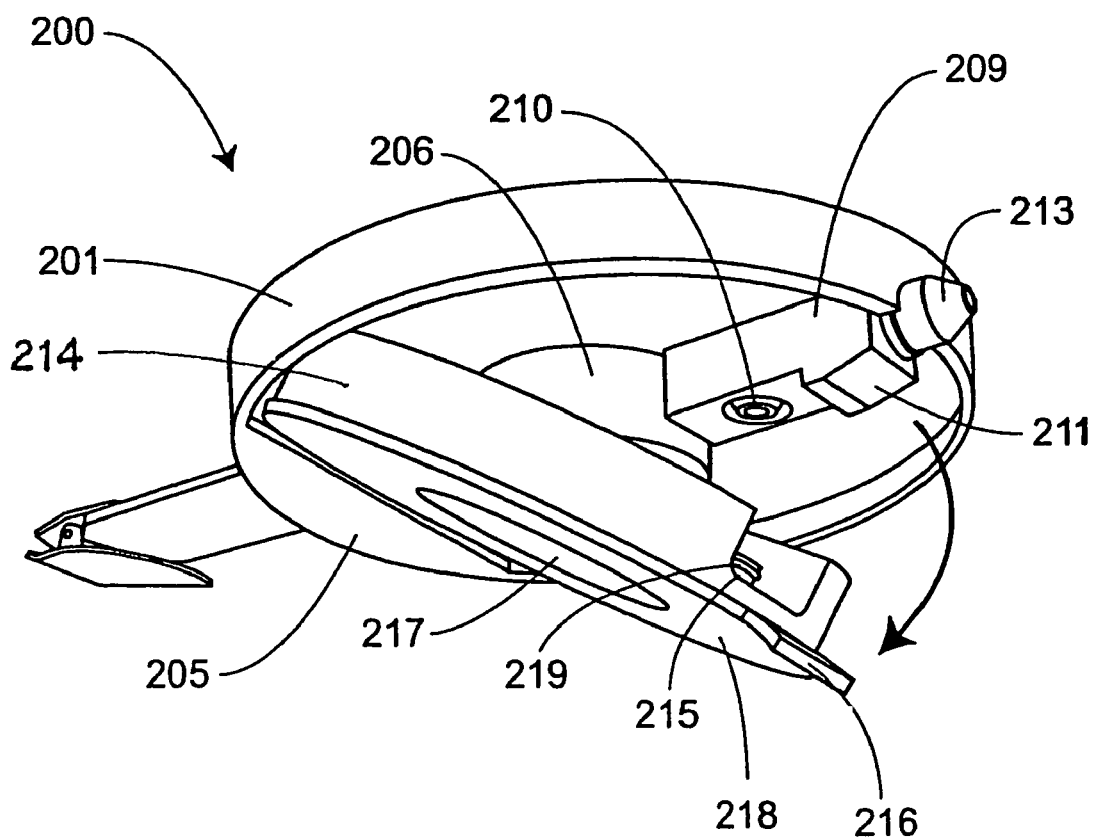
FIG. 19 is a bottom view perspective drawing showing an agent dispenser with an agent cartridge removed.
Figure 20:
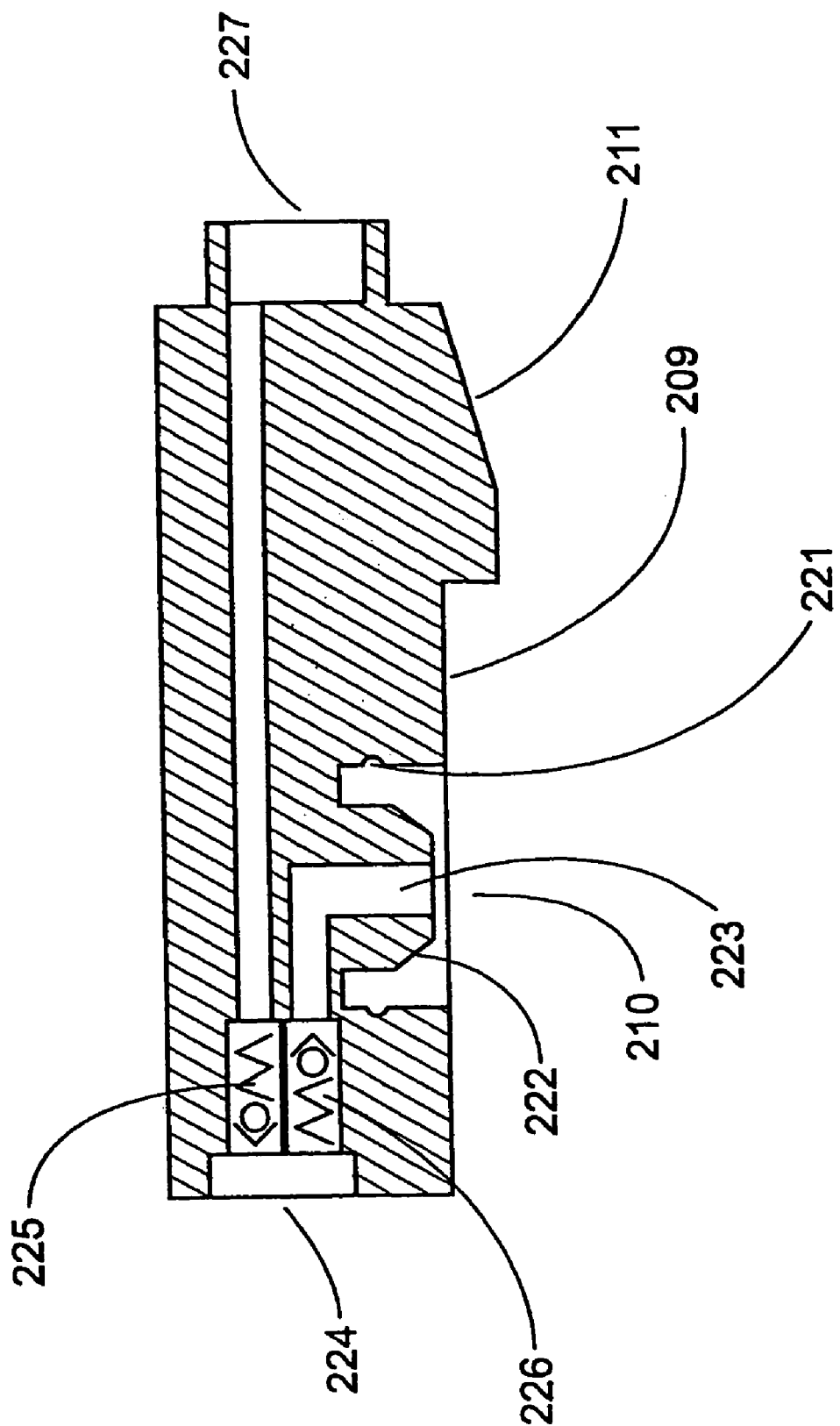
FIG. 20 is a cross section side view drawing showing an agent dispenser valve assembly when using a replaceable agent cartridge.

The FIG. 16 front view of the agent dispenser replaceable cartridge 214, shows the valve body assembly entrapment area 220, and the elastomeric compression ring seal 219 in an annular groove which surrounds male mating port 215. The cartridge removing pull tab is shown at 216. The FIG. 17 side view of cartridge 214 shows in dotted lines, the compression ring seal 219 in place in the external groove around the male mating port 215, and the central aperture 217 in the cartridge. The FIG. 18 bottom view perspective of agent dispenser 200 shows a replaceable agent cartridge in place in the dispenser's housing 201, for use. FIG. 19 bottom view perspective shows the cartridge being removed from the dispenser housing. FIG. 20 shows in cross section, the valve body assembly 209 which incorporates a nozzle attachment boss 227, a pump connection socket 224, an inlet check valve to pump 226 which is connected to inlet port 210 and barrier seal surface 222 through flow tube 223 and connected for sealing with the replaceable cartridge (FIG. 19) at port sealing ring 219 (FIGS. 17 and 19) which mates with female retaining groove 221 in the valve body. Flow of agent from agent replaceable cartridge flows through outflow check valve assembly 225. Ring 219 serves both the functions of sealing the connection between the valve body and the cartridge and, by seating in the groove in the cartridge boss for port 215 and the groove 221 of valve body 209, it retains the front end of the cartridge in the dispenser housing.

Figure 21:
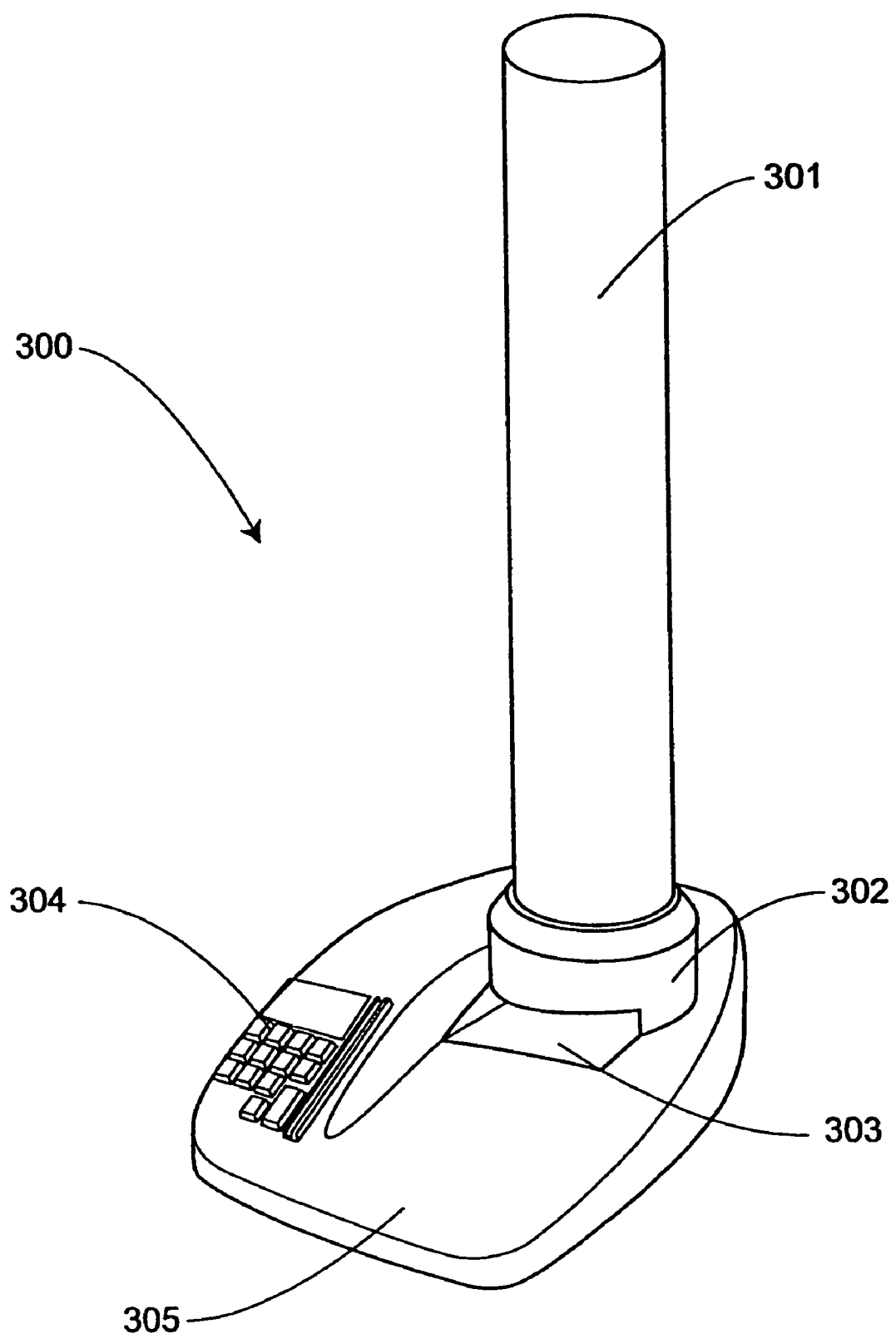
FIG. 21 is a perspective front view drawing showing a dispenser's replaceable agent cartridge vending station.

FIG. 21 is a front perspective view of a replaceable agent cartridge control and vending apparatus 300 wherein a data entry keypad/card swipe component 304 is shown. The issuable agent replaceable cartridges in inventory are stacked within tubular chamber 301 wherein said chamber is held within vending apparatus 300 by retaining frame 302. Replaceable agent cartridges are delivered for use through issuance slot 303 outwardly down ramp 305.

Figure 22:
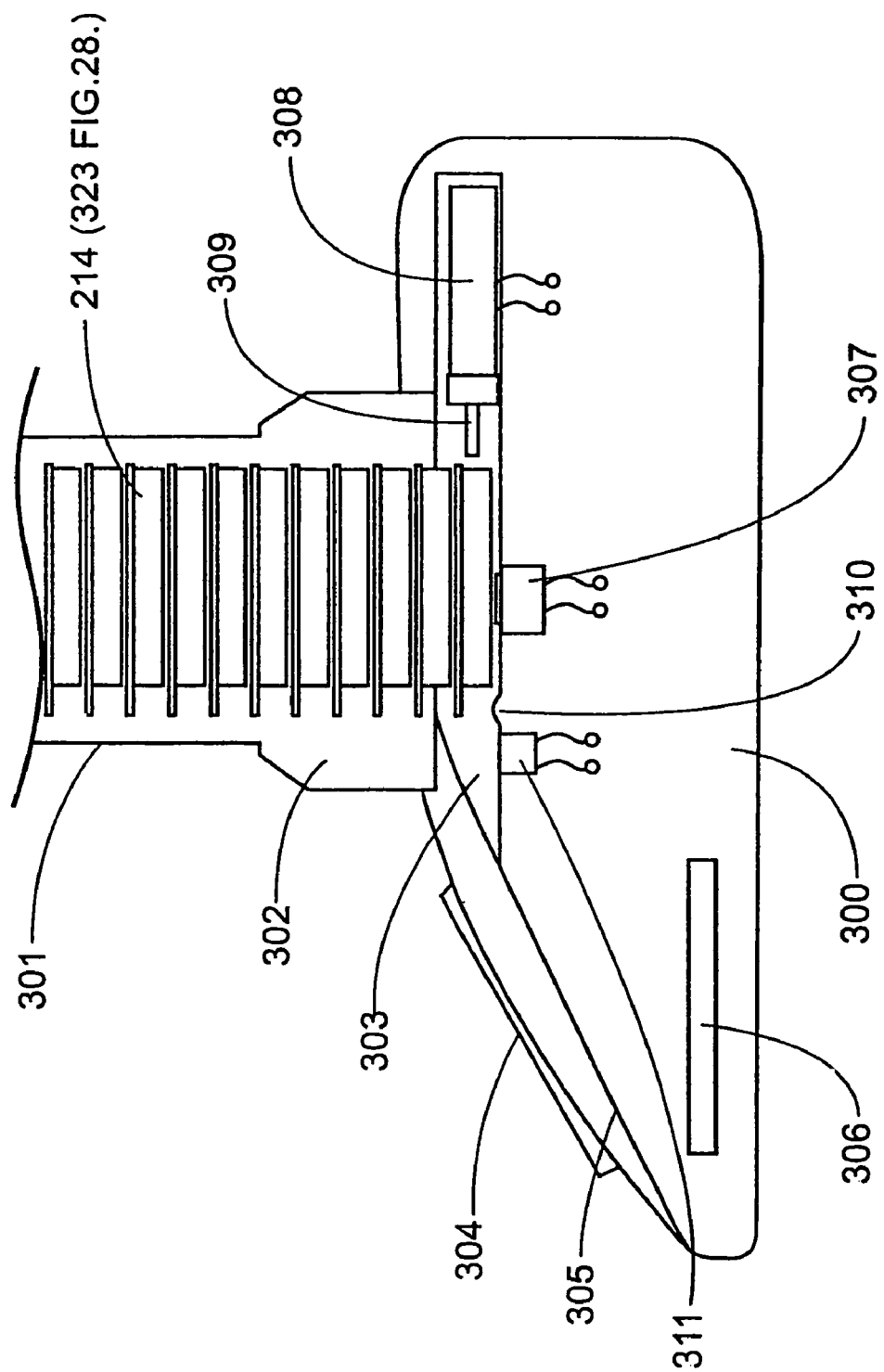
FIG. 22 is a cross section side view partial drawing of the replaceable agent cartridge vending station showing the cartridge vending elements.

Referring to FIG. 22, a partial cross section side view of the apparatus 300 shows a processor 306 to record data entry through 304. Replaceable cartridges 214 are ejected from the station 300 by linear actuator 308 through piston rod 309. Restricter hump 310 positions replaceable cartridges 214 for exit and user retrieval. Electronic sensor 307 records and reports when a cartridge chamber 301 is depleted of ready to use cartridges. An electronic reader 311 is located to read and record unique identifiers of replaceable agent cartridges when dispensed.

Multiple Compartment Replaceable Cartridge

Figure 23:
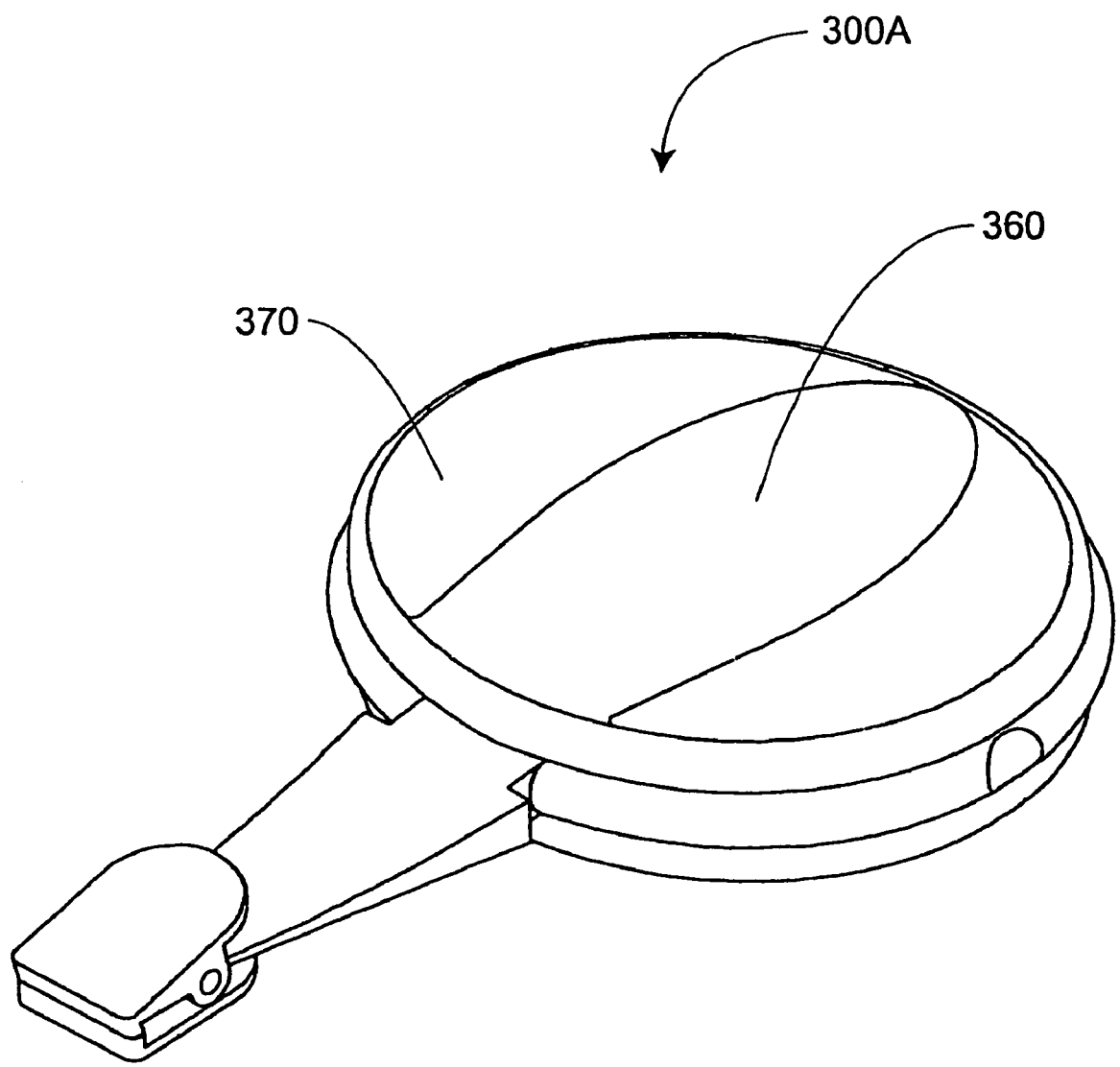
FIG. 23 is a top view perspective drawing of another embodiment of the present invention agent dispenser using a multiple compartment agent replaceable cartridge.

In a further embodiment shown in perspective view FIG. 23, the present invention provides a personal, portable hand held and hand operated hand sanitizer dispenser 300A. Top half section 370 contains lever arm compressor with press pad 360, shown in a closed position.

Figure 24:
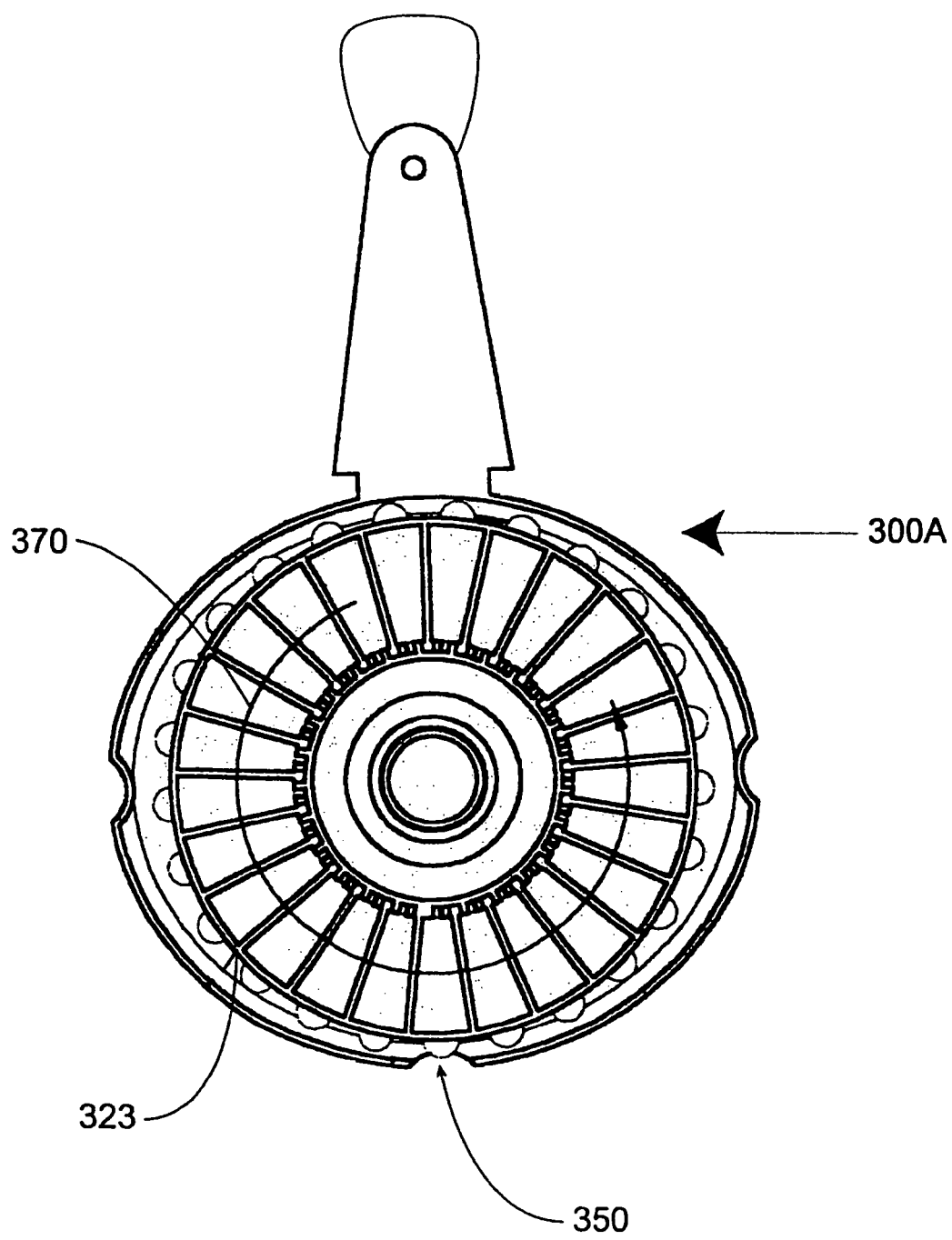
FIG. 24 is a top view drawing of the FIG. 23 dispenser using a multiple compartment agent replaceable cartridge, with the top dispenser housing removed.

FIG. 24 shows a top view drawing of dispenser 300A with the top half section 370 removed which shows the nozzle opening 350, and the arrow 370 which shows the direction of advancing movement of the replaceable cartridge platform 323 as the nipples 318 are advanced to registry one-at-a-time, with nozzle opening 350 to dispense fluid contents of a cell.

Figure 25:
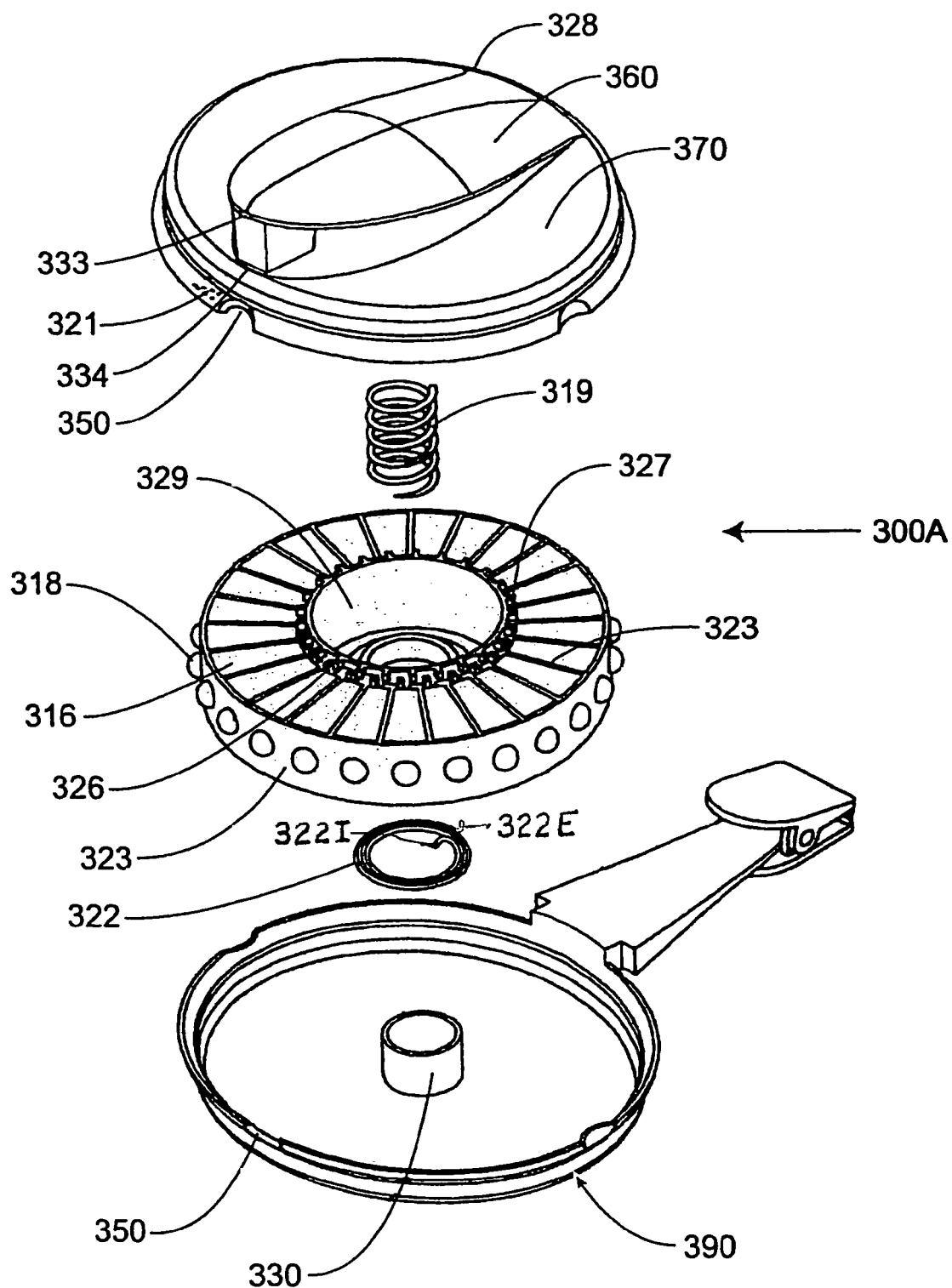
FIG. 25 is a front perspective exploded view drawing of the FIG. 23 agent dispenser using a multiple compartment agent replaceable cartridge.
Figure 29:
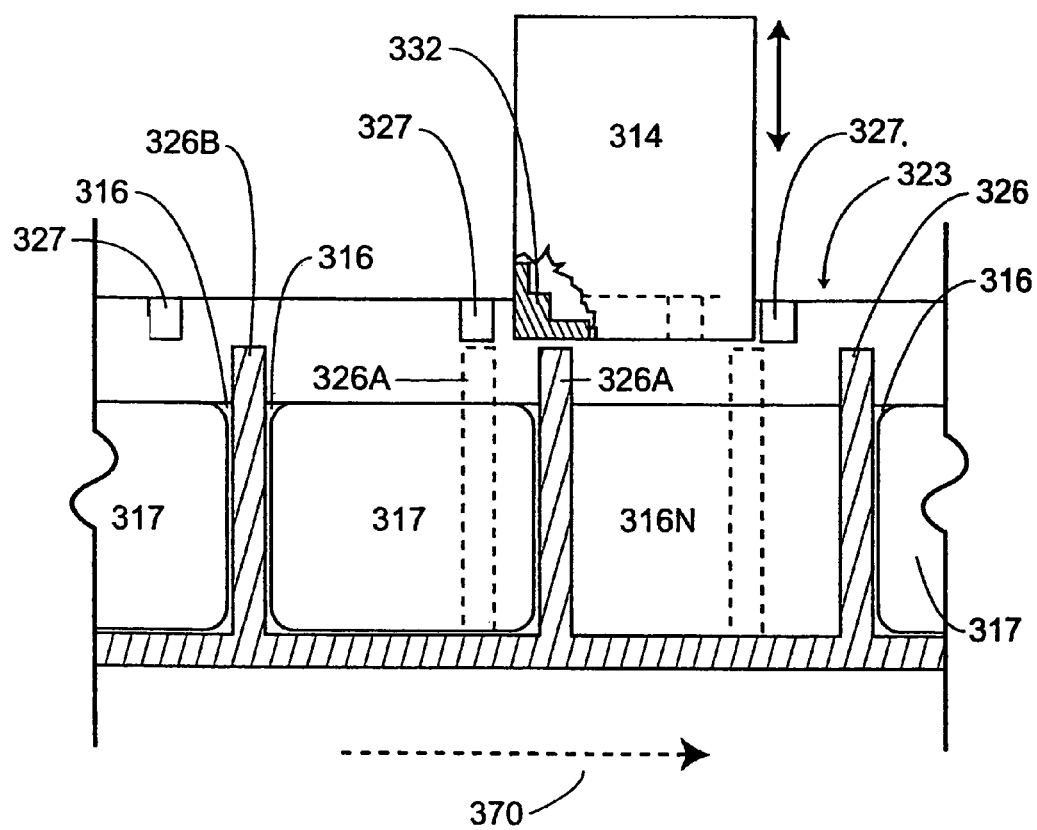
FIG. 29 is an enlarged fragmentary section of the rotatable platform of the dispenser cartridge of FIG. 27, with associated presser foot.

FIG. 25 shows the dispenser 300A in a perspective exploded view wherein the dispenser's bottom half section 390 and its top half section 370 represent the dispenser 300A housing. Individual fluid unit dose compartments are represented by 316 and are integrated within a platform 323 which can be advanced rotationally about an upwardly projecting hub 330 in the dispenser bottom half. Platform 323 has advance control stops represented by 326, 327. The fluid unit dose compartments represented by 316 have flexible bags 317 in them, one in each compartment except one which will be referred to herein as the "nest" compartment 316N (FIG. 29). Each of the bags has an agent fluid exit point represented by nipple 318.

Lever compressor arm with pad 360 is located in dispenser top half section 370 and is connected at hinge point 328 and has a normal upward bias assisted by a spring-like extender 319 and can be positioned and held in a downward lock position by conventional overlapping tab-on-tab or tab-in-groove closure with closure tab 333 engaged in groove 334 in housing bottom half 390. Rotatably advanceable platform 323 is connected to platform rotary advancing clock-mainspring-style assist spring 322 which is connected at its inner end 3221 to support column 330 located in the dispenser bottom half section 390. The outer end of spring 322 sticks up at 322E and engages a shoulder in the spring receiving recess in the bottom of platform 323. A bag piercing edge 321 is located in the housing top half section 390 immediately adjacent to the dispenser nozzle opening 350 (FIG. 25).

Figure 26:
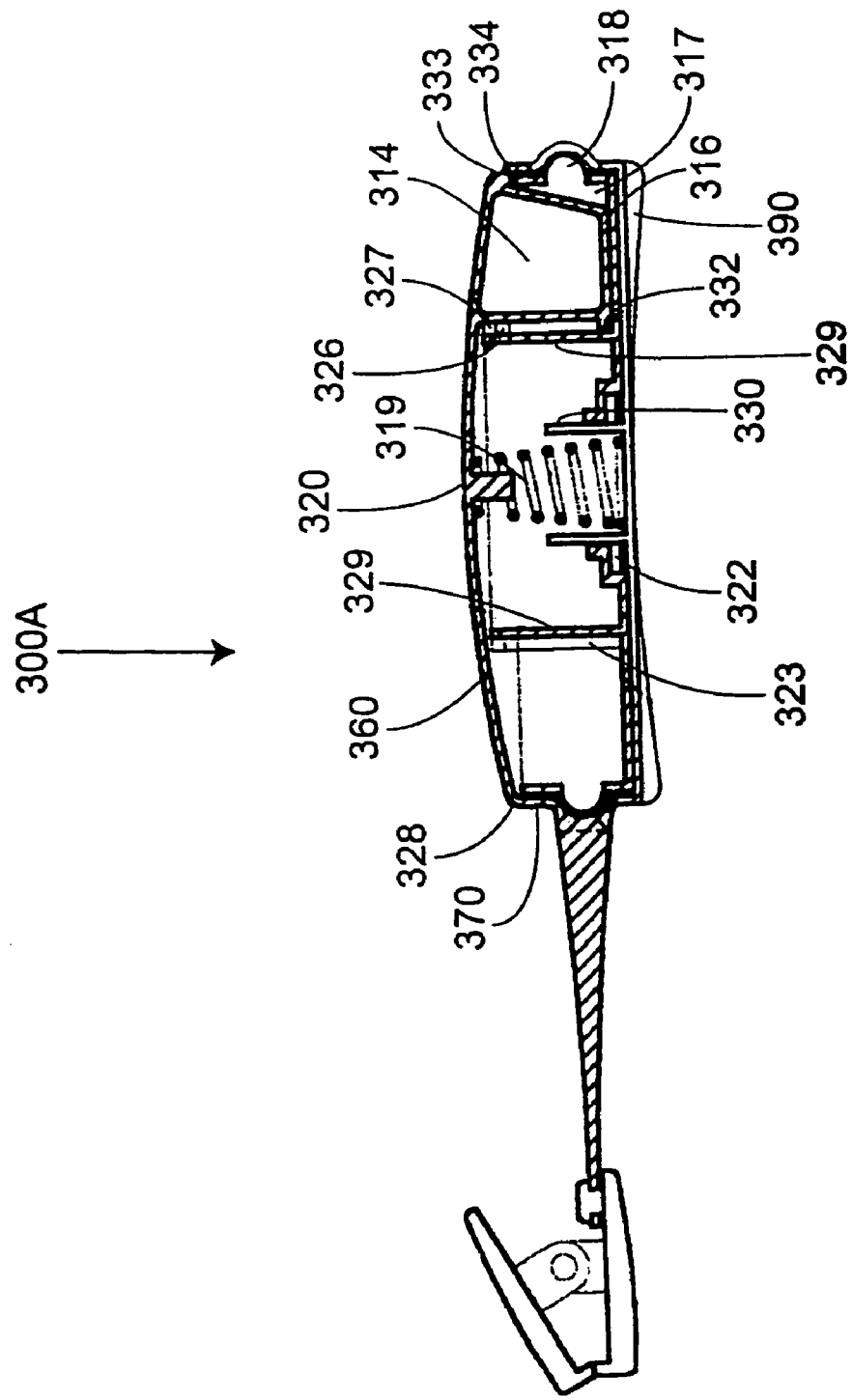
FIG. 26 is a side view in cross section drawing of the multiple compartment agent replaceable cartridge dispenser in a closed position after dispensing agent from cell 317 in one compartment 316.

FIG. 26 is a cross sectional side view of dispenser 330A shown in a closed position wherein it is shown that the lever arm compressor has a "living hinge" at point 328 at the rear end, and a compressor foot 314 at the distal front end. A platform advance stop tab 332 is provided at the lower rear end of the foot 314. A stud 320 is provided on the underside of lever arm compressor pad 360, and retains the upper end of spring-like extender 319. The inside vertical wall sections of the fluid cell compartment of the platform 323 are represented by 329.

Figure 27:
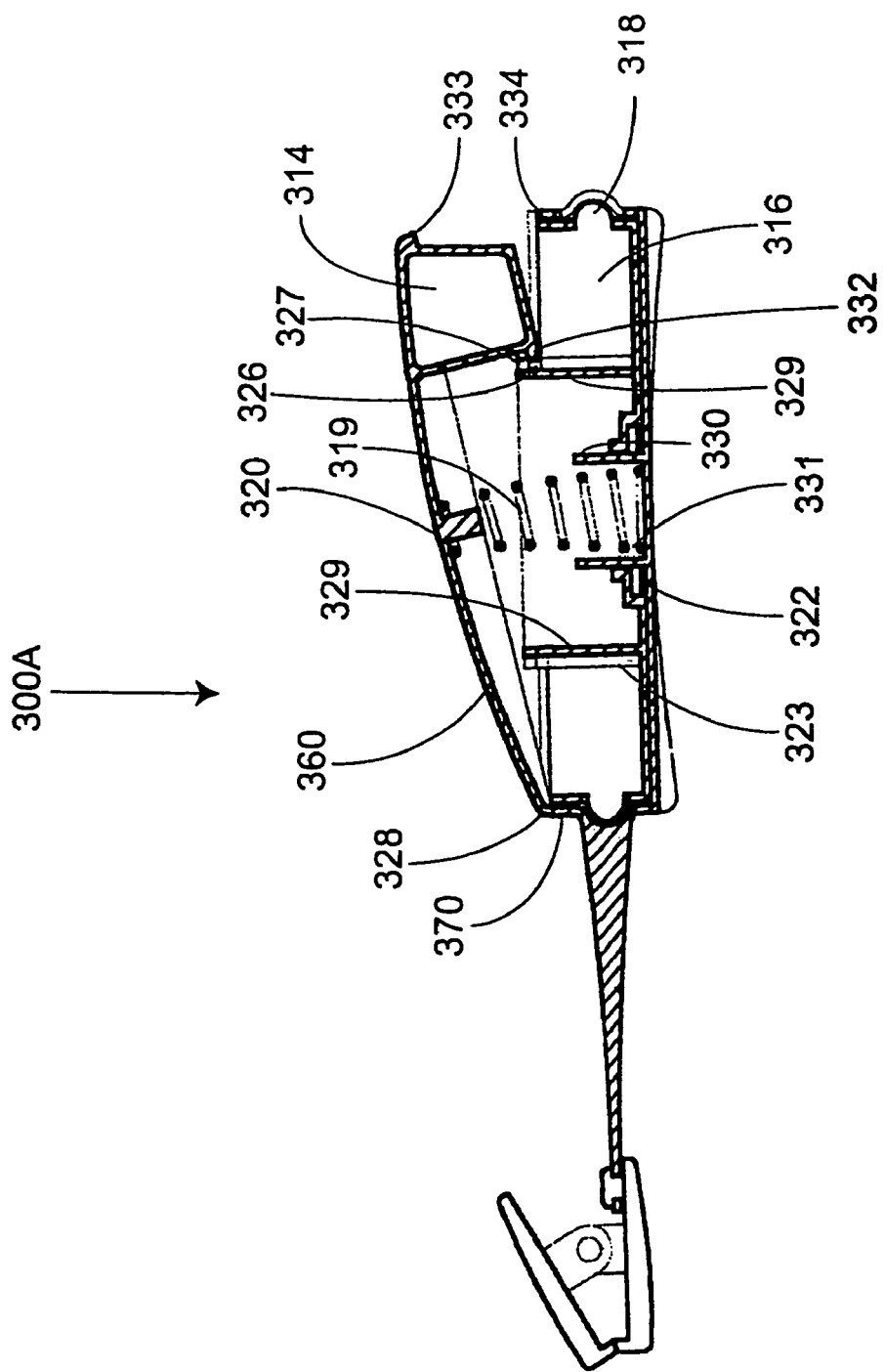
FIG. 27 is a side view in cross section drawing of the multiple compartment agent replaceable cartridge dispenser in an open position.

FIG. 27 represents the cross sectional side view of dispenser 330A shown in an open position.

Operation

Dispenser with Single Agent Replaceable Cartridge

The department of healthcare workers within a hospital environment that would use an agent dispenser component of the hospital hand cleaning network system that incorporates a replaceable agent cartridge would be those healthcare workers having contact with patients in a less than critical care or intensive care areas of the hospital wherein the patients generally would have healthier immune systems and therefore less susceptible to nosocomial infections. Healthcare workers would simply be monitored as to how many replaceable cartridges over a given time frame were issued to the user, with each cartridge representing a quantity of hand cleaning applications that occurred between the issuance of each cartridge.

The user first inserts cartridge 214 (FIG. 15) into the dispenser 200 by tipping the frontal surface of the cartridge downwardly and the rear surface of the cartridge upwardly to allow its entrance (FIG. 19) into the rear section of the dispenser between the dispenser top housing 201 and the dispenser's frame ledge 205. The rearward section of the bottom 218 of the cartridge is held in place by ledge 205 as shown in FIG. 18. The user then presses in an upwardly direction on the cartridge's frontal surface causing the cartridge port 215 (FIG. 16) to enter the dispenser valve body 209 and connect to intake port 210. The cartridge seal ring 219 enters groove 221 (FIG. 20) of the valve body and holds the cartridge in place. The dispenser is now ready to dispense agent.

When the user presses the dispenser's press pad 202 (FIG. 15) it causes pump activator 207 to move downwardly causing agent to be discharged from the pump 206 into the valve body 209 by connection 208 to 224 (FIG. 20). The agent flows through check valve 225 and out through nozzle 213 (FIG. 15) for use by the user. When the user releases the dispenser's press pad 202, the press pad returns to its up position by the pump 206 activator 207 which has a spring like bias within the pump chamber below the piston to encourage the up position of the piston (like FIG. 3, for example).

When the piston pump strokes upward following the completion of a downward stroke which causes the agent to be dispensed from the dispenser, it causes a vacuum to take place which then draws agent from the cartridge 214 (FIG. 15) through the sealed connection 210-215 between the cartridge and dispenser valve body which has been previously described. Agent from the cartridge flows through check valve 226 (FIG. 20) and into pump 206 (FIG. 15) in a quantity required for the next discharge event. When a cartridge is empty, the user simply pulls tab 216 (FIG. 19) (FIG. 17) in a downwardly motion which disengages the cartridge from dispenser for its removal (FIG. 19).

Operation

Multiple Compartment Agent Replaceable Cartridge

The multiple compartment agent replaceable cartridge dispenser component of the hospital hand cleaning network system is used by the patients of the healthcare facility wherein the multiple compartment dispensers can be pre-set to the quantity of unit dose hand cleaning agent applications that would normally occur during the stay of the patient within the hospital. Upon that patient's release from the hospital, a visual inspection of the cartridge immediately exhibits the number of hand cleaning operations that the patient executed during their stay in the hospital. The information is recorded, and the dispenser is properly discarded by hospital personnel.

Upon a user's receipt of dispenser 300A, they can attach said dispenser 300A to clothing or other convenient locations for use, with attachment clip which is connected by a pivot fastener to a flexible tail section which is a connected extension of dispenser 300A bottom half section 390.

Figure 28:
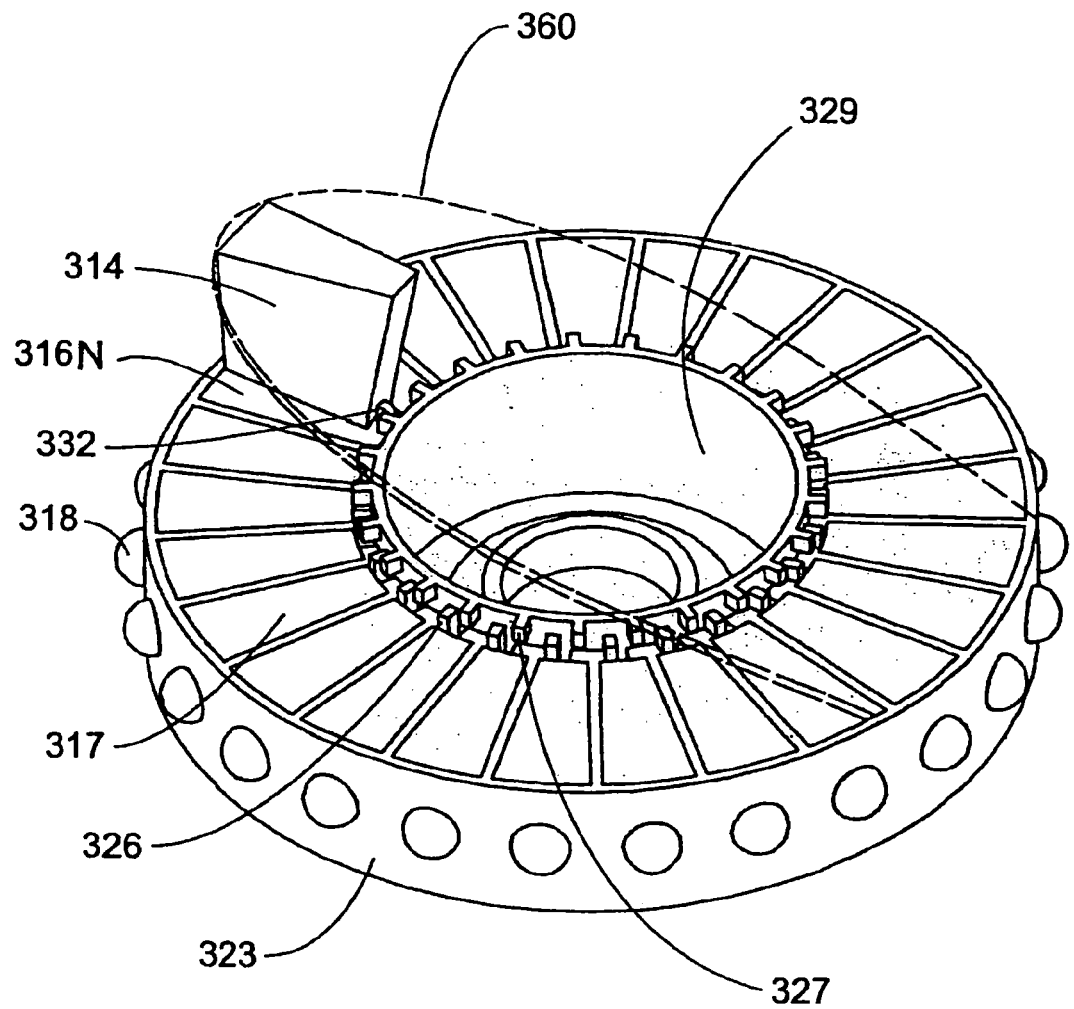
FIG. 28 is a top perspective view of the rotatable platform of the dispenser cartridge of FIG. 27, and the associated lever compressor arm (shown dotted) and its presser foot.

To sanitize their hands, a user, using one hand, presses lever arm compressor pad 360 in a downward and sideways motion which disengages closure tab 333 from closure tab 334 allowing the lever arm compressor to release from a closed position (FIG. 26) to an open ready-to-use position (FIGS. 27-29). When the lever arm compressor is disengaged, the extender spring 319 urges the lever arm compressor to pivot to its most upward position (FIGS. 27-29), the compressor foot 314 being thereby removed from the open "nest" compartment 316N (FIG. 29). As tab 332 at the inboard lower end of presser foot 314 rises past the upper edge of stop 326A in its dotted line location, the rotational advance spring 322 turns the platform moving stop 327 into abutting relation with tab 332, where it stops, as shown in the solid lines in FIG. 29

To apply a single fluid unit dose of sanitizing solution, a user will press in a downward direction on lever arm compressor pad 360. Within a short downward travel distance of about 0.5 inches of the most forward portion of the lever arm about hinge 328, the platform advancement stop tab 332 on the lever arm becomes disengaged from platform advance control stop 327 which immediately allows for the fluid unit dose compartment platform 323 to be rotatably advanced in the direction of arrow 370 (FIGS. 24, 28) by platform rotational assist spring 322, until stop 326B stops against stop tab 332 of the lever arm. Stop 326B, extending down to the bottom of compartment 316 (as do all of the stops 326), remains in contact with stop tab 332 for the remaining downward travel of lever arm compressor, preventing any additional advancement of the compartment platform 323. Also, as the advancement stop tab 332 becomes instantly disengaged from platform stop 327 and the platform 323 advances, the individual fluid cell compartment 316, the flexible cell 317 therein and the nipple 318 on the cell, advance past piercing edge 321 which pierces the nipple immediately prior to arriving in position of registry with nozzle opening 350. When the stop 326 on platform 323 stops against stop tab 332, the nipple is in registry with nozzle 350. As the lever compressor arm continues its uninterrupted downward motion while the stop 326A remains in contact with stop tab 332, the foot 314 squeezes the cell 317.

The lever arm compressor foot 314 is shaped to mate with the individual unit dose fluid cell 317 as shown in FIGS. 26, 28 and 29, to assure a complete discharge of fluid from within the flexible unit dose fluid cell 317 as it is collapsed, and out through the pierced nipple 318 and out through nozzle opening 350 of the platform and onto the user's hand, upon the completion of the user's downwardly directed press of lever compressor arm pad 360.

The flexible material used for the unit dose cell 317 is available from many companies such as Anderson Packaging, Inc. 4545 Assembly Drive, Rockford, Ill. 61109 or EVC Film, Inc., 400 Christian Lane, Kensington, Conn. 06037.

Examples of manufacturers of unit dose cell compartment platforms are companies such as Key International, Inc. 480 Route 9, Englishtown, N.J. 07726 or Bosch Packaging Technology, 8700 Wyoming Ave. N., Minneapolis, Minn. 53445.

The flexible material used to contain unit dose cells similar to 317, and the manufacturing process required for doing so, are known within the industries providing such products as "Unit Dose Blister Packaging".

After the contents of fluid unit dose cell 317 have been expelled through nozzle opening 350, the lever arm compressor returns by spring 319 to its most upward, open position shown in FIG. 27. The unit dose fluid compartment's nipple 318 recovers and returns by its material memory, to its original shape even after compression. This encourages the compartment 317 to close the puncture at the pierced location and inhibit any residual leakage. Platform advancement stop tab 332 remains in contact with platform advancing stop 326, preventing any advancement of the compartment platform 323 until lever arm compressor reaches approximately 0.5 inches from its upward travel stop whereupon platform advancing stop 326 disengages from platform advancement stop tab 332 allowing the compartment platform to advance by platform advancement assist spring 322 in the direction of arrow 370 until platform advancement control stop 327 engages platform advancement stop tab 332. Upon the completion of the upward travel of the lever compressor arm, the dispenser 300A is now ready to repeat a hand sanitizing operation.

As indicated above, advancement direction of the unit dose fluid cell compartment platform 323 is shown as 370. As it indexes the distance required to process an individual unit dose fluid cell 317 two (2) separate advancements take place with the platform 323. One, when the lever arm compressor begins its downward travel and two, when the lever arm compressor returns upwardly.

Upon the completion of using a dispenser 300A the user presses downwardly and sideways on the distal end of lever compressor arm until closure 333 engages closure 334, latching the arm in the closed condition.

There are examples of prior art inventions relating to advancing mechanisms for dispensing and/or delivering individual items such as U.S. Pat. No. 5,664,697 issued to Lawrence E. Lambelet on Sep. 9, 1997 describing a cyclically indexing pill container, or U.S. Pat. No. 5,460,295 issued to Herbert Law on Oct. 24, 1995 which describes a novel candy indexing container.

U.S. Pat. No. 5,603,429 issued to Paul Mulhauser on Feb. 18, 1997 discloses a motorized hand held dispenser that has a turntable with compartments holding objects and which are dispensed from the rotating turntable. U.S. Pat. No. 4,053,041 issued to Francises Corte on Oct. 11, 1977 discloses a labeling device with a indexable platform.

Now referring to the procedure with dispenser 300A for replacing a used cartridge 336, the top section 370 of the housing is manually unsnapped from the bottom section 390, allowing complete unobstructed access to and removal of the used cartridge. The platform engaging end 322E of the advancing assist spring 322 is automatically disengaged from platform 323 as the used cartridge is pulled out of the bottom housing section. Upon insertion of the new cartridge, the upwardly projecting platform engaging end of the spring is engaged in the downwardly opening socket in the new platform. As the bottom housing section 390 is held in one hand and the top housing section 370 in the other hand, the presser foot 314 is inserted into compartment 316N of the new cartridge. Then the top housing section is turned by hand 360 degrees relative to the bottom section and in a direction opposite the direction of the arrow 370. This winds the spring and places the vacant compartment 316N in registry with the nozzle opening 350 in the bottom section, thereby positioning the cartridge to establish a start holding position of the new cartridge for the next cycle use. Then the top section is snapped onto the bottom section and the dispenser is ready to use. During wind-up, the nipples are not damaged as the top housing section is not yet snapped together with the bottom housing section and the nipples are moving in a direction to simply pass under the back of the nipple piercing edge of the housing top section. In this embodiment of the invention, as in the others, it is not necessary to use tools in dealing with the dispensers or the control station or the replacement cartridges.

Operation

Replaceable Agent Cartridge Control Station

The control apparatus 300 (FIGS. 21 and 22) contains a stack of replaceable agent cartridges 214 within column 301. The column is held within the control apparatus by circular frame 302. A user simply enters user unique identifier data at data entry point 304 (FIG. 21) either by keypad or magnetic card swipe etc. of the apparatus 300. The user access data is stored along with date/time data into the memory of processor 306 (FIG. 22). Upon a user's successful user data entry, a signal is sent by the processor to activate linear activator 308 to extend its shaft 309 which contacts and expels a single replaceable agent cartridge (single cavity 214 (FIG. 15) or multiple compartment 323 (FIG. 25)) through issuance slot 303 (FIG. 21). When the inventory gets low, a weight sensitive switch 307 (FIG. 22) will signal an empty column to the processor 306 to display a "Refill" message at the visual display of the data entry location 304 (FIG. 21). The apparatus 300 may also incorporate an electronic reader 311 (FIG. 22). When periodic user/usage studies of dispenser cartridges are required, the electronic reader could be activated to read and record a cartridge's unique identifier, and the user to whom it was issued and on what date and time. Random collection of used cartridges, and off-site processing of the unique identifiers with user identifiers, and the measurement of agent used over time of user possession, could form representations as to a given user group's compliance with hand cleaning standards.

Most portions of the dispensers of the various embodiments of the present invention can be made of lightweight plastic materials. Plastics may be used to a large extent in the control stations, regardless of whether they are of the type that store cleaning agent in bulk, as in the FIG. 6 embodiment, or the type that store cleaning agent only in throw-away dispensers, or the type that store cleaning agent in cartridges of single compartment or multi-compartment nature, or the type that store cleaning agent in replaceable cartridges already in the dispensers as in FIG. 22.

The hand treatment agent can be any of a variety currently available. Some specifically for sanitizing are mentioned above. The apparatus of the invention may be used for other products, preferably in a liquid, mist, foam or other fluid form. The user identifier reader for recognizing an authorized user may be something other than a card reader. Some other examples are readers for unique personal body identifiers or readers for identifier devices embedded in a user. An example of a personal body identifier is a fingerprint. Also, the multi-compartment replaceable cartridges shown and described are circular, and advanced from position to position by rotation about an axis. But it should be understood that replaceable cartridges of other forms may also be devised and used within the scope of some aspects of the invention. Moreover, multi-compartment replaceable cartridges which can be advanced linearly, rather than circularly may also be devised and used within the scope of some aspects of the invention.

It should also be understood that an aspect of the present invention can employ control station of FIG. 22 with agent dispensers that are pre-filled with cleaning agent and are to be properly discarded after use. Some embodiments will now be described here.

Disposable Dispenser

Referring now to FIGS. 30-40 and following, dispenser 411 includes a housing 412, a flexible bag 413 containing the hand treatment agent and attached onto the housing 412. A treatment agent discharge port, non-drip nozzle 414 is at the front of the housing, and a resilient dome 416 is provided on the top of the housing as a press pad for pressing by the user of the dispenser to dispense a hand treatment agent from the bag 413. A dispenser identifier may be provided on the bag, usually in the form of a bar code 417 on a label 400, for example. When the dispenser identifier is used in a system according to one method of practicing the invention, the identifier is unique to each dispenser and distinguishes it from all other dispenser identifiers and dispensers in the system. If desired, the unique identifier may be omitted from dispensers used in another method of practicing the invention.

In the previously described embodiments of the invention, a dispenser hanger of one type is shown and described. In the embodiments of the FIG. 30 and following, a different type of hanger is shown. It includes a strip 418 of craft liner paper having a proximal end 419 and distal end 421. The portion adjacent the proximal end is affixed to the bag 413, and the strip may be folded from the extended position as shown in FIGS. 31, 35, 35A, 36 and 37 to the folded position shown in the FIGS. 30, 32, 33 and 39. As shown in FIG. 36, the surface on one side of the strip has adhesive (3M 9877, for example) on it in a rectangular area 422 located between the distal end 421 of the strip and the rear end 424 of the bag. The remainder 420 of the area on the one side of the strip shown in FIG. 36 has an easy release surface.

Figure 35:
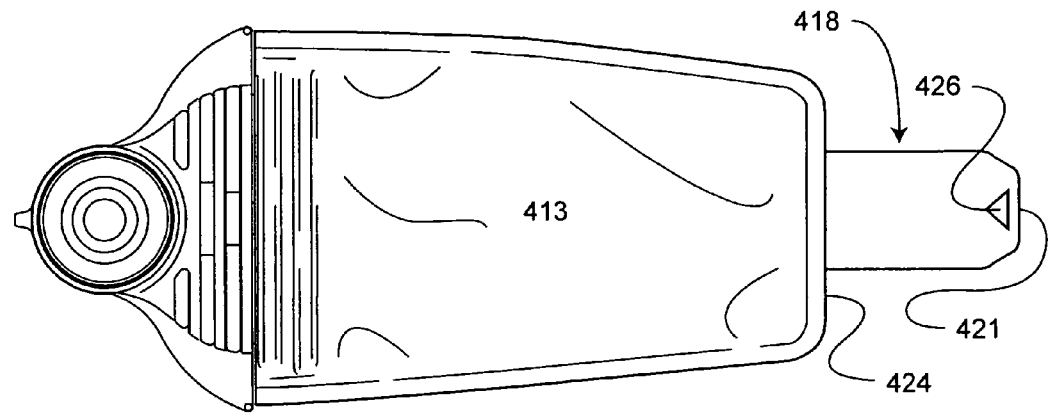
FIG. 35 is a bottom plan view of the dispenser and showing the attachment strip extended to enable attachment to the garment of a wearer.
Figure 35A:
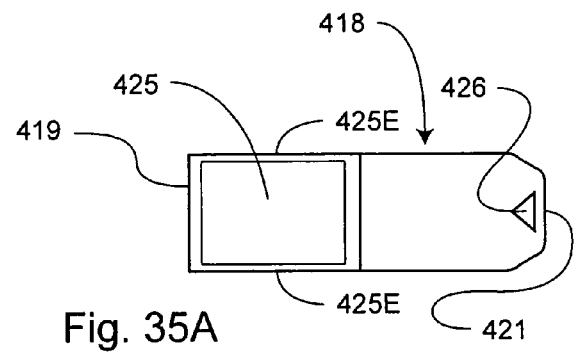
Figure 36:
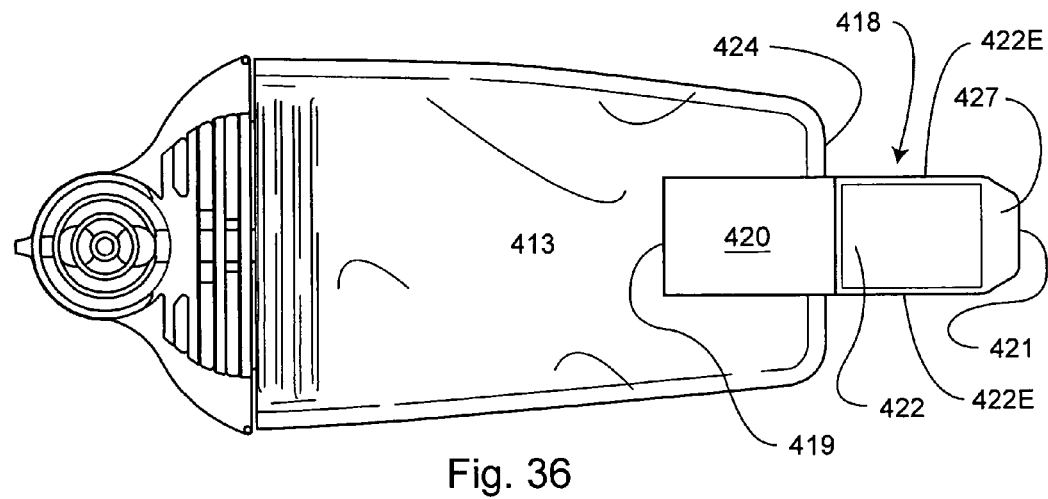
FIG. 36 is a bottom plan view of the dispenser with the attachment device extended.
Figure 37:
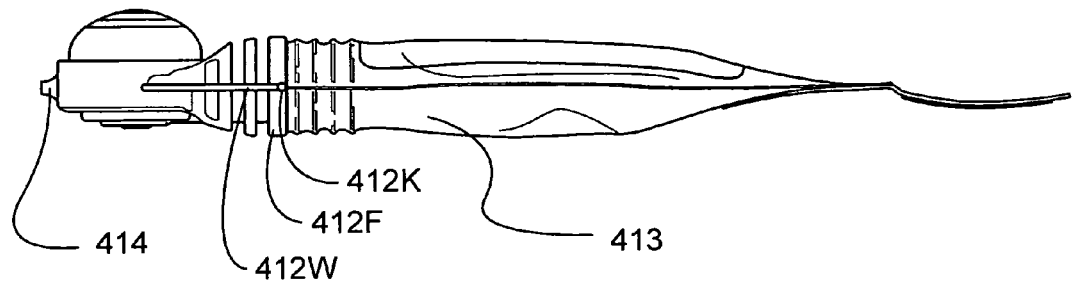
FIG. 37 is a side elevational view of the FIG. 30 dispenser with the attachment strip extended.
Figure 37A:
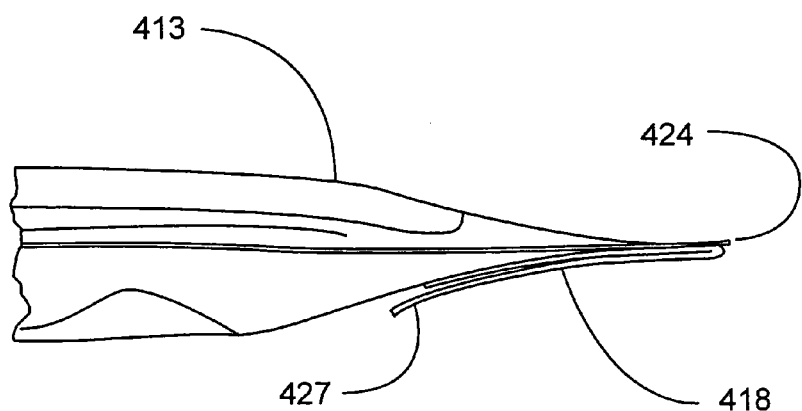

The other side of the strip is shown in FIG. 35A and has adhesive (3M 9471, for example) at 425 between the proximal end 419 of the strip and the rear end 424 of the bag, and whereby the strip 418 is permanently attached to the bag 413. The 3M 9471 is used because of its ability to adhere in a permanent fashion to the pliable material (usually high density polyethylene film) of the bag 413. Also, further referring to FIGS. 35 and 35A, a visual triangle 426 is printed on the same face of the strip 418 as adhesive 425 but adjacent the distal end of 421 of the strip. When the dispenser is not being worn, the strip is folded in half from the extended position as shown in FIGS. 31, 35, 35A, 36 and 37 to the folded position shown in the FIGS. 30, 32, 33 and 39. In this condition, the adhesive 422 on it adheres to the easy release surface area 420 of the strip portion between the rear end 424 of the bag and the proximal end 419 of the strip. During manufacture of the strip, as will be described hereinafter, the strip 418 is die cut from a roll to the illustrated shape that extends farther toward the distal end 421 of the strip than does the adhesive 422, so it leaves an overhang portion 427 which is not stuck to the permanently fixed portion of the strip when the strip is folded in half for storage of the dispenser. This portion serves as a pull tab.

Figure 31:
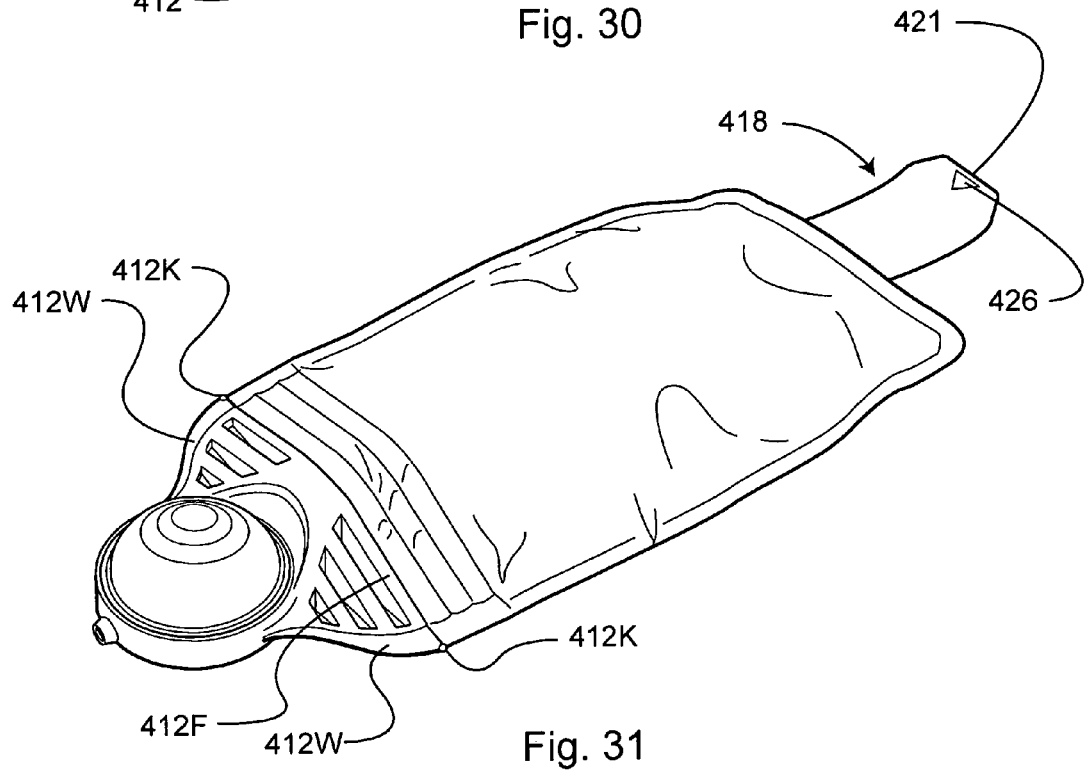
FIG. 31 is a view like FIG. 30 except for showing a device for attachment to a garment of a person wearing the dispenser.
Figure 32:
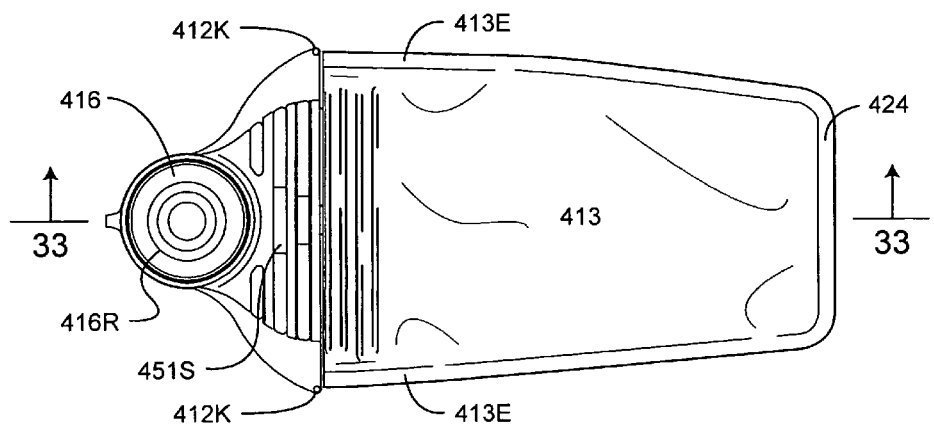
FIG. 32 is a top plan view.
Figure 34:
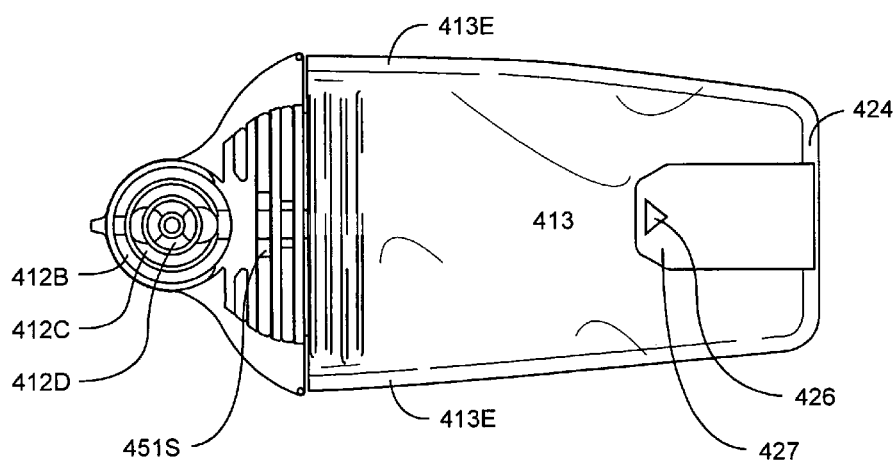
FIG. 34 is a bottom plan view of the dispenser of FIG. 32.

As shown in FIG. 34, when the strip 418 is folded, the triangle 426 shows on the pull tab at the distal end 421 of the strip, and serves as an arrow oriented to alert the user to pull the strip in the direction of the arrow to extend the strip to the extended position shown in FIG. 31, for example. The sticky portion 422 is then available to stick onto the clothing of the wearer. The sticky portion faces in the same direction as the bottom surface of the housing and bag so that, when attached to the outside of the shirt or blouse or other garment or accessory of the wearer, the strip serves as a hanger and orients the dome 416 to face out from the wearer and make it readily available to the hand of the wearer who can conveniently grip the bag housing and push the dome 416 to dispense the treatment agent from the discharge nozzle 414 at the front end 423 of the dispenser. Of course, it should be understood that, while the front end and rear end of the dispenser are mentioned above, these will be respectively the bottom and top of the dispenser when worn by the user and hanging from a shirt, belt, trousers or slacks or other garment or accessory.

The 3M 9877 material is particularly useful at 422 on the strip, because of its ability to be applied and removed from clothing materials many times and still remain tacky. Therefore, when the use removes the hanger from their clothing temporarily and plans to reattach later, the strip can be folded to place the adhesive area 422 against the fixed portion of the strip, for protection of the portion 422 from outside debris or accidental adhesion to other surfaces.

Figure 33:
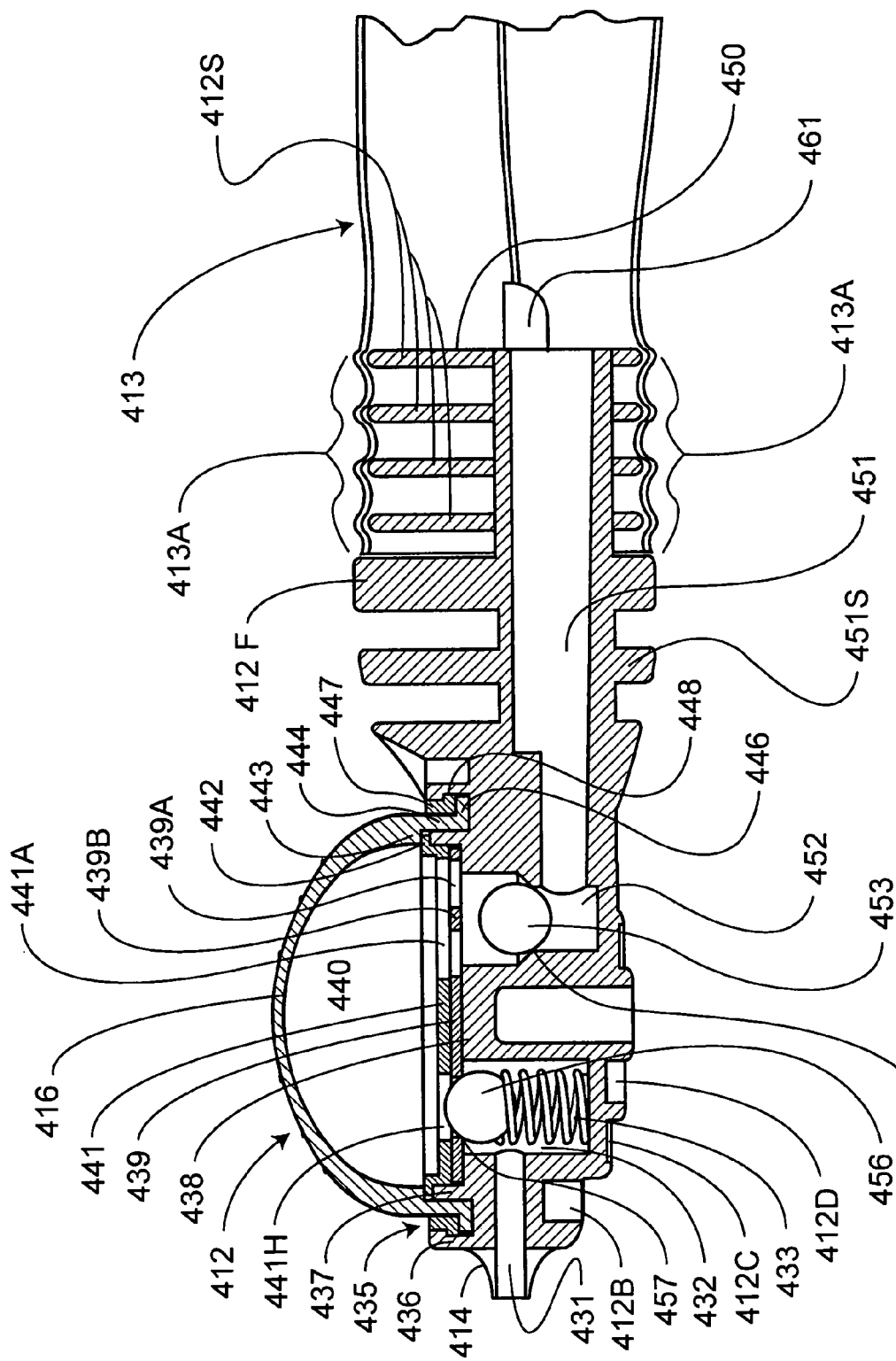
FIG. 33 is an enlarged sectional view of a portion of the dispenser of FIG. 32 and taken at line 33-33 in FIG. 32 and viewed in the direction of the arrows.
Figure 38:
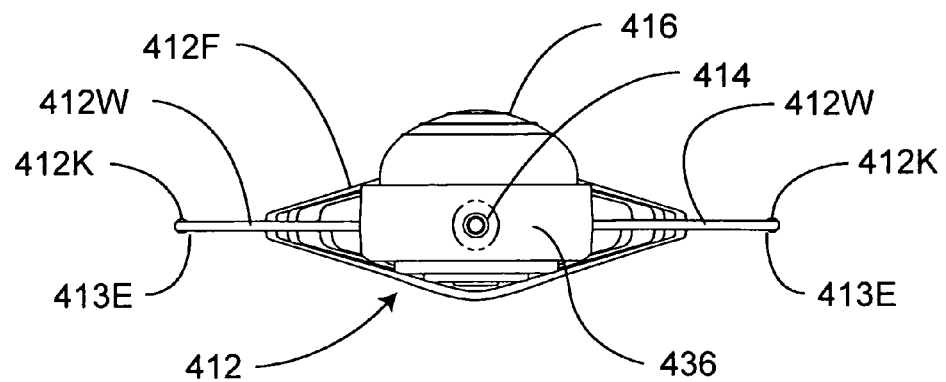
FIG. 38 is a front elevational view of the dispenser.
Figure 40:
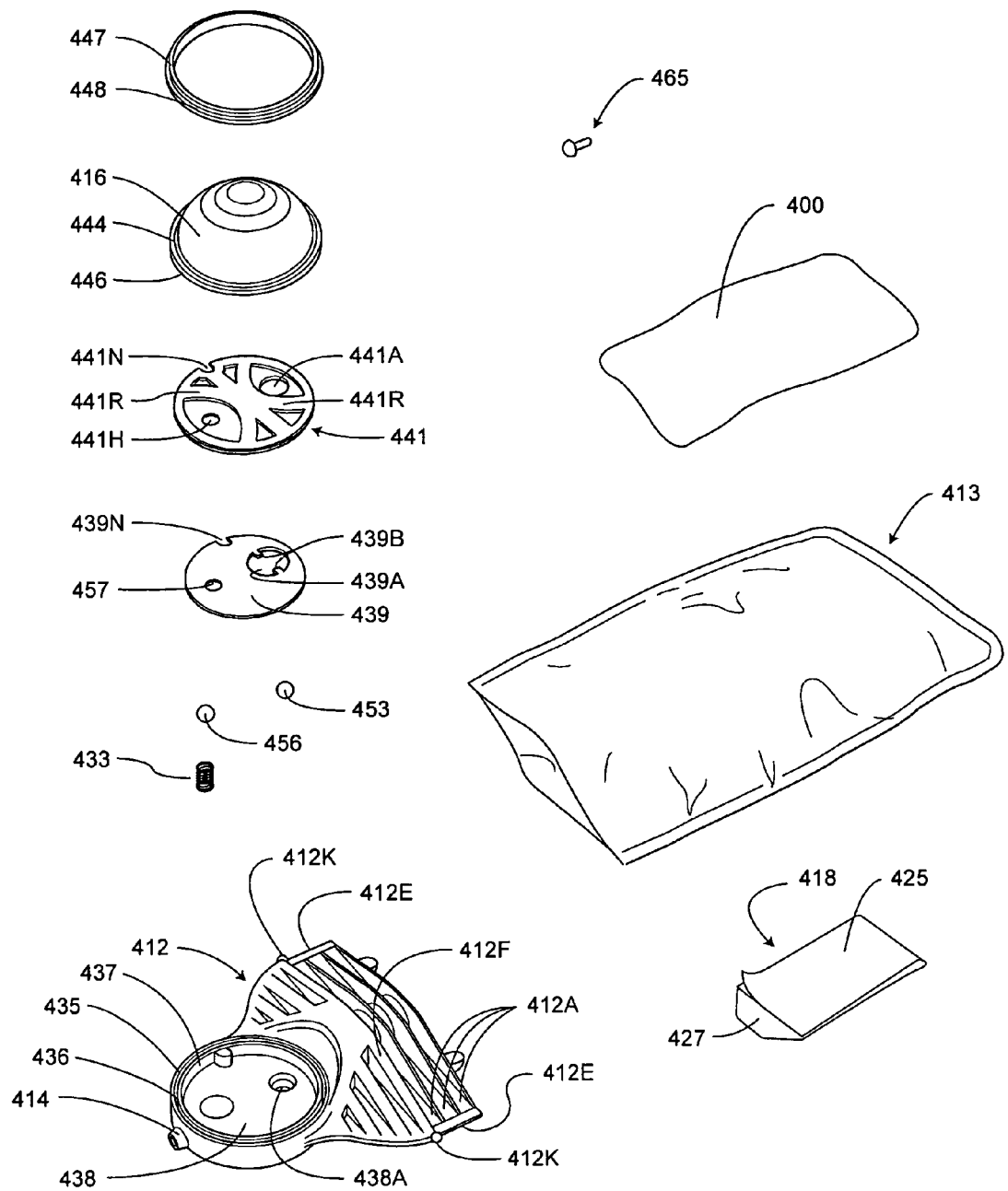
FIG. 40 is an exploded view of the dispenser, in perspective.

Referring now to FIG. 33, the illustrated portion of housing 412 is enlarged to show some interior details. The nozzle 414 at the front end communicates through a passageway 431 to a chamber 432 receiving a coil spring 433 which is centered in and sits on the bottom of the chamber. The housing 412 includes an upwardly-opening groove 435 between a couple of concentric cylindrical walls, an outer wall 436 and an inner wall 437. The inner wall surrounds a floor 438 of the press pad pump chamber 440. A ball seat disk 439 is received on the floor 438 and centered by the wall 437. A press pad retainer disk 441 rests on the disk 439 and is also centered by the wall 437. The retainer disk 441 has a flange 442 which rests atop the wall 437 and provides support for an inwardly extending inner perimeter flange 443 of the resilient dome 416, which has a skirt portion 444 projecting down from the flange 443. The skirt has an outer perimeter flange 446 projecting out from the bottom of the skirt portion. A press pad retainer ring 447 is received on the inside surface of the wall 436 and has a step in its profile that allows it to snap into an undercut detail located on the inside face of wall 436. More specifically, the ring 447 has an outer flange 448 received in an inwardly facing groove in the housing wall 436. The retainer ring 447 can be continuous as shown in FIG. 38, and forced into the upwardly opening groove 435 between the walls 436 and 437 of the housing for a snap fit to retain the dome skirt 444 and ring outer flange 448 in that groove. Alternatively, a split ring may be used in that site, if desired. When the retainer ring flange is received in the undercut on the inside face of wall 436, the press pad outer flange or lip 446 is pressed by the ring 447 against the bottom of the groove 435. The press pad thereby holds down other components including the retainer disk 441 and the ball seat disk 439. Referring to FIG. 40, an index tab 437T in wall 437 projects inward for reception in notch 439N in the ball seat disk and notch 441N in retainer disk 441 to index the holes in these parts relative to the holes in the housing floor 438.

Referring again to FIG. 33, a passageway 451 extends from the rear end 450 of the housing into the chamber 452 in the housing. The rear end of the passageway 451 communicates directly into the hand cleaning agent storage reservoir bag 413.

A ball 453 rests on a circular seat 454 in the housing. A ball 456 is mounted atop the spring 433. This ball, urged upward by spring 433, is normally seated against the edge of a circular hole 457 in the disk 439. The edge of the hole 457, supported from above by the retainer disk 441 at hole 441H therein (FIG. 40) serves as the valve seat. Curved stiffening ribs 441R are provided around holes 441H and 441R in disk 441. They prevent warping of the disk.

Figure 30:
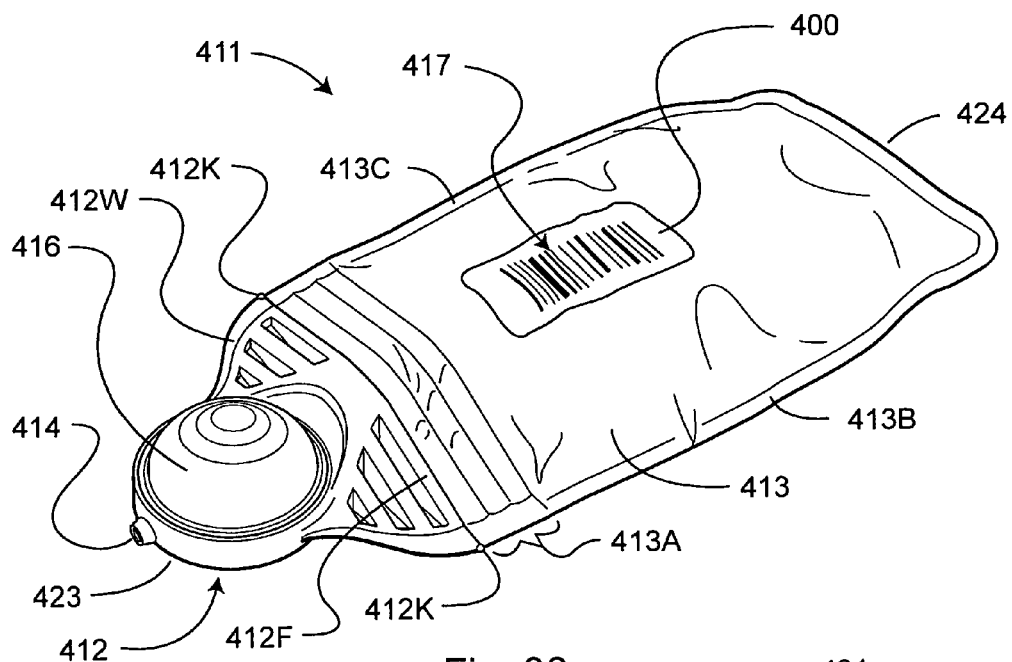
FIG. 30 is a perspective view of a dispenser according to a further embodiment of the present invention.

The flexible storage bag 413 for the hand treatment agent is a metalized laminate material which is heat sealed onto the housing on top and bottom in the area 413A (FIG. 30). It is also heat sealed along one or both of the edges 413B and 413C. After filling with the hand treatment agent, the bag is heat sealed at that portion of the rear end 424 which was left open during fabrication, to admit the filler tube. The passageway duct 451 in the rear portion of the housing provides communication directly from the interior of the bag to the chamber 452. Therefore, in the use of the device, the liquid contents of the reservoir 413 can communicate with the interior of the dome 416 through the chamber 452 and openings 438A in the base and 439A in the ball seat disk 439. Therefore, after the press pad is released from compression during a dispensing event, the hand treatment agent in the bag 413 can flow into the chamber 452 and then to the interior chamber 440 of the dome 416 as it resiliently restores itself to rest condition in its original dome shape and size. The cleaning agent is prevented from departing from the dome due to the sealing of the check ball 456 against the seat at 457. When the user is ready to dispense some hand cleaning agent onto a hand, the pad 416 is pressed by one thumb or finger. The pressure rise forces the ball 453 against seat 454 and pushes the ball 456 away from the seat 457 and discharges the cleaning agent from the interior of the dome 416 through the passageway 431 and nozzle 414 to the user's hand. Upon release of thumb or finger force from the dome, the spring 433 closes valve ball against seat 457. Simultaneously, as the dome 416 resiliently returns to normal shape, the ball 453 is able to leave the seat 454 and permit the reservoir to re-fill the dome. The tabs 439B on the ball seat disk 439 (FIG. 40), project into hole 439A in the disk 439, and prevent the check ball 453 from leaving the chamber 452 and entering the dome 416. As cleaning agent moves from bag 413 toward the dome, and since there is no way that air can enter the bag 413, the bag collapses a little during return of the dome to original rest condition. Tabs 461 on the rear face 450 of the valve body serve as stand-offs to prevent the bag from collapsing against the entrance to passageway 451, so that the bag won't plug that opening.

Figure 39:
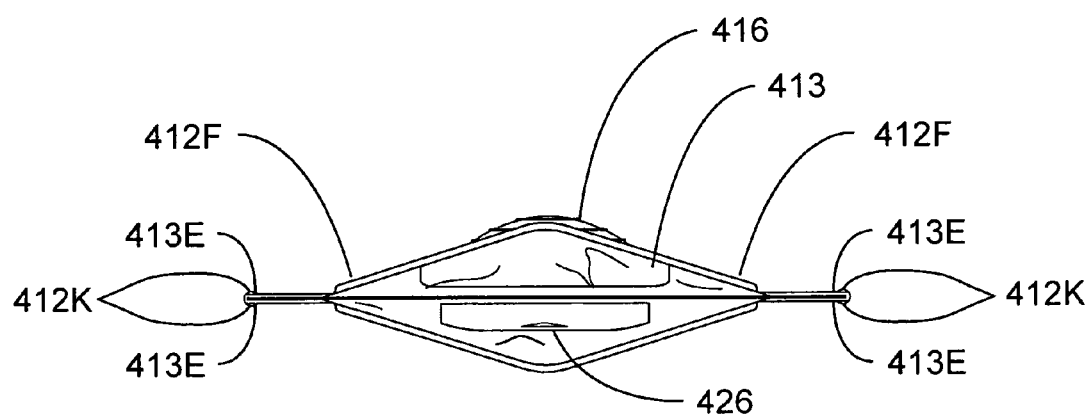
FIG. 39 is a rear elevational view of the dispenser with the attachment strip folded as in FIGS. 30 and 32-34.

Referring now to FIGS. 33, 38 and particularly FIG. 39, the latter being a rear end view of the dispenser, it may be noted that the front portion of the bag 413 is generally the shape of a diamond. From an originally flat condition, the front end portion of the bag becomes generally diamond shaped when it is mounted to the housing and moved forward until the front end of the bag stops at the wall 412F of the housing. As the bag is moved onto the housing, the front end and frontal portions of the bag conform to the shape of four longitudinally spaced parallel ribs 412S of the housing and which are behind the wall 412F and are of the same diamond shape as wall 412F. These ribs 412S are integral with a web 412A which extends laterally from both sides of the wall of duct 451. The ribs are all engaged by and heat sealed to the frontal portion of the bag at 413A, thus completely sealing the frontal portion of the bag to the housing around the perimeter of the ribs 412S. As shown in most of the FIG. 30 and following, the sides of the housing flare outwardly and rearward like wings 412W. At the tips of the wings at their maximum spread, the wall 412F converges toward points where, instead of points, there are small spherical shaped knobs 412K. These soften the edges and protect the user and the bag from otherwise sharp corners. Also, exterior locations on the dispenser where there might otherwise be points or sharps, are rounded consistent with the desire to protect the user and prevent the dispenser or parts thereof from snagging other objects and to protect other dispensers if stored against or nearby.

Before the bag is mounted to the housing, the edges 413E of the top and bottom sheets of film are heat sealed together all the way back to the rear end 424 of the bag. Therefore, the bag is completely sealed along its edges 413E, and then to the ribs 412S to prepare the bag ready for filling from the end 424, which remains unsealed at that time. The side tips of the valve body's rear diamond shape ribs 412S are manufactured paper-thin so that they actually melt when the housing 412 is heat welded to the bag. Therefore the ribs blend right into the creases created in the two sheets of bag film material when the bag is installed onto the housing ribs. All of these ribs 412S and 412F are molded in one piece with the central or spine portion 451S which can be referred to as the plumbing duct portion of the housing and which extends rearward from the valve body portion toward the rear end 450 of the housing. Each of the ribs 412S runs all the way around the plumbing duct 451S and has a rounded surface at the top and bottom so that the perimeter of the rib melts together into complete contact with the bag film while melting. Once the heat welding is complete, a perfect seal has been made so that the only area that the hand sanitizing agent can pass through is the passageway 451 in the plumbing duct.

Further regarding the ribs and the bag, it is believed to be preferable that the distance between the outer edges 412E (FIG. 40) of the inter-rib web 412A is about 2.25 inches. This will provide for a comfortable overall bag width at the rear of the housing 412, of 2.625 inches, including the edge welded edge portions 413B of the bag. Also, since the bag tapers very little through the distance of about 4.25 inches from the front end to the rear end 424, and because the foil component in the layers of the bag film tends to resist crumpling, the bag can remain in relatively consistent longitudinal and lateral dimension as its hand treatment agent content is being used and its thickness decreases accordingly. The width helps keep the dispenser properly oriented in the hand of the user while operating the press pad, even when the bag is nearly empty. Also, features on the bottom of the housing defining downward-opening grooves 412B, 412C and 412D (FIGS. 33, 34), while rounded to avoid sharp edges, provide tactile feedback to the user when operating the press pad. Tactile feedback to the user is also provided by the small circular ridges 416R on the top of the press pad dome.

If desired, a nozzle plug 465 (FIG. 40) can be provided in the nozzle 441 for shipping and handling and for removal manually by the ultimate user. Because of the relatively small passageway 431, it is not necessary to reinstall the nozzle plug after dispensing a dose of hand cleaning agent from the dispenser.

Further regarding the press pad 416, the term "dome" is used herein, but should not be construed as limited to a perfectly spherical shape. The curvature and the wall thickness may vary throughout the structure of this dome for the purpose of controlling how the press pad reacts when it is pressed downward. It is desirable, but not essential, that a "snap" action feel be achieved as the pad is pressed, and a spring-like rebound when digit (finger or thumb) pressure is released. This enables the user to know that a quantity of 0.7 to 1.2 milliliters of hand treatment agent have been discharged through the nozzle 414 during a single dose discharge event.

A snap action feel, if desired, can be established by combination of dome material, shape, size, and wall thickness variation, any of which can affect the way the pad collapses and folds while being pressed by the user.

Further regarding the hand sanitizing agent storage bag, it was mentioned above that the bag 413 is made of two pieces of film laminate which are heat sealed or welded along the edges 413E. That sub-assembly is then heat sealed or welded to the ribs 412S entirely around the housing 413. For filling the assembly with the hand sanitizing agent, the assembly can be mounted to a machine that orients the assembly so the nozzle is pointing downward and the open end 424 of the bag is facing upward. A filling tube (not shown) is lowered into the bag, and the tip of the filling tube is lowered to almost the housing rear end 450. Filling begins and, as the solution level rises, the filling tube is brought upward at the same time. The purpose of the filling tube traveling vertically is to eliminate excess air being trapped in the bag during the injection of the agent. By the time the bag is filled with the specified, approximately 30 ml (milliliters) of fluid hand sanitizing agent, solution, the filling tube has made its way outside of the bag and out of the way for a set of jaw-like contour sealing dies that come in and heat seal/weld the last open side of the bag closed. The dispenser is now filled with the hand treatment agent and ready to function. Following that step, the product label, the adhesive hanger, and optional nozzle plug can be installed.

If needed, to enhance sealing at various locations in the assembly, crush ribs (not shown) protruding from a surface, can be provided. Examples of locations are: at the bottom of the upstanding groove 435 and engaging the flange 446 on the press pad; the bottom of the retainer disk 441 engaging the ball seat disk 439, particularly around the ball seat hole 457; the floor 438 of the press pad pump cavity, making a liquid-tight seal with ball seat disk; on the bottom of the retainer disk 441, particularly around the hole 441H to press into the ball seat disk for sealing around the ball 456 at the seat disk; and on the floor 438 projecting upward from the floor 438 around the hole 457 in the ball seat disk.

For most of the components of the illustrated housing assembly, a high density polyethylene material can be molded and used in the various shapes required. A stainless steel is used for the valve spring and stainless steel can be used for the valve balls, although high density polyethylene can be used for the balls too. The ball seat disk 439 and the press pad 416 are made of low density Sarlink®, a type of thermoplastic elastomer available from a variety of sources. Other elastomers or rubber-like resilient materials may be used. The material used for the bag in this example is a multi-layer laminate of high density polyethylene with one layer of metal foil. An example is 48 gauge PET (polyethylene terephthalate) polyester laminated to an 11.2 pound white LDPE laminated to a 0.00285 gauge foil laminated to a 10.8# LDPE laminated to a 1.5 mil LLDPE (Linear Low Density Polyethylene). The low density polyethylene layer is at one face of the laminate and is situated to face inward toward the surfaces of the housing and inner cavity. This is effective because the housing is made of a polyethylene also and will bond to this layer for the heat seal and welding operation. The foil layer and others are outboard of this layer and act as a barrier against puncture, ultraviolet light and other contaminants. The material for the hanger is grade 10924 S 80# SB SCK 4400M/000 R, which is a re-moisturized, semi-bleached super calendared kraft liner.

The liner material from which the strip 418 is made, can be furnished in a roll (not shown) having a width equal to or slightly greater than the length desired from end 419 to end 421 for the strip 418. One face of the liner has adhesive 3M9471 on a little less than half the width of the roll from one edge of the roll and extending throughout the length of the material wound on the roll. The other face of the liner has adhesive 3M9877 on a little less than half the width of the roll from a marginal area near the other edge of the roll, and throughout the length of the material wound on the roll. The marginal area is the portion which will become the tab 427. So when the roll is unwound, and run through a machine for cutting the individual strips 418 from the roll, and shaping the tab 427, the adhesive areas 422 and 425 will extend to the edges of the strips 418 as at 422E and 425E (FIGS. 35A and 36).

The adhesive used in the area of 425 is 3M9471 is marketed by the 3M Company. The adhesive in area 422 is 3M9877 is also marketed by the 3M Company. Adhesives by other companies might also be useful in this application.

While the bar code 417 can be used on this embodiment of the invention, for identifying the dispenser and distinguishing it from all other dispensers of the same type, a simplified mode of practicing the invention can omit the bar code and keep track of how often a dispenser user returns one empty dispenser and obtains another and the times of such events. In that way, dispenser issuance from a control station to a user, and return by the user to the same or another control station in the network, can be monitored, so hand sanitizing activity of a user can be noted.

The above examples of materials useful in the practice of the invention are only for purposes of example. Other materials may be found to be suitable for the intended purposes of their use.

Figure 41:
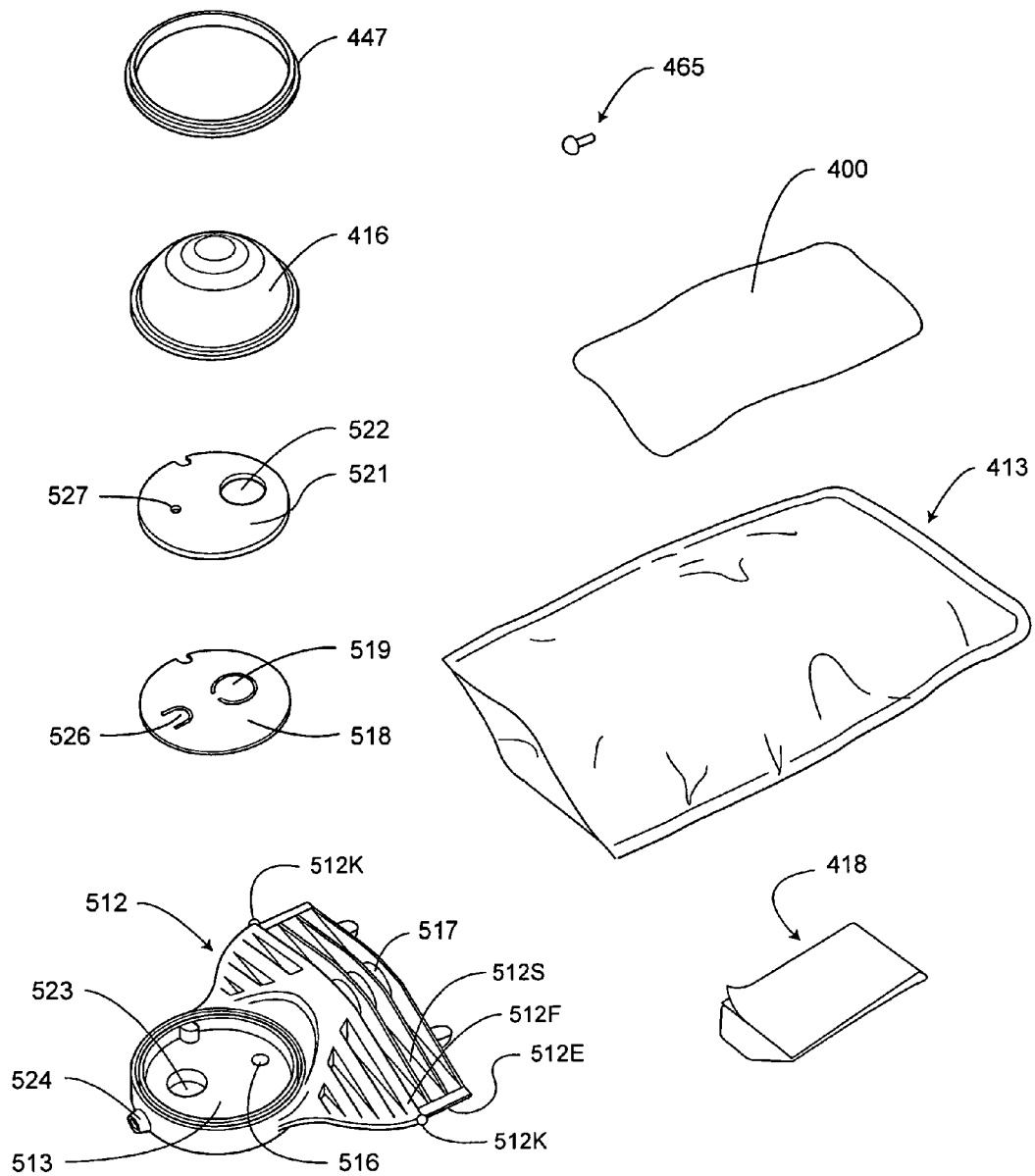
FIG. 41 is an exploded view of a further embodiment of the dispenser, with flapper valves instead of ball valves.
Figure 42:
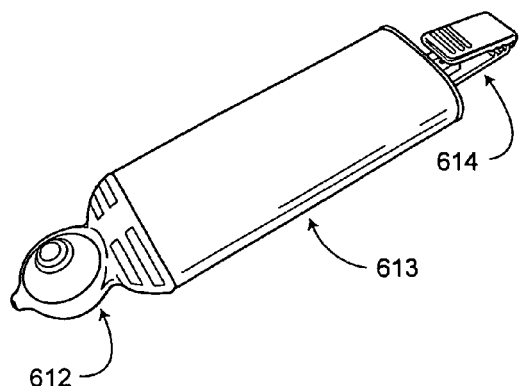
FIG. 42 is a perspective view of a hard-bodied reservoir version according to an embodiment of the present invention.

Referring now to FIG. 41, a further embodiment incorporating the invention is illustrated. In this example, flapper valves are used instead of ball valves. The housing 512 is similar in many respects to housing 412 of the previous embodiment. The bag 413, bag mounting features, hanger 418, and label 400 if any label is used, can be the same as in the previous embodiment, so they are given the same or similar reference numerals. So are the press pad 416 and retainer ring 447. A small hole 516 is provided in the housing 512 to communicate with the plumbing duct 517 from the bag 413. This hole is different from the hole above the valve ball 453 in the FIG. 40 embodiment. Hole 516 in the FIG. 41 embodiment is normally covered by the flapper 519 on flapper disk 518. The flapper 519 is considerably larger than the hole 516 so that when the flapper retainer disk 521 is mounted in the housing and secured in place by the dome 416 and retainer 447 as in the previous embodiment, the flapper disk 518 is secured in place and the flapper is able to tilt upward into the hole 522 in the dome chamber. This is the intake portion of the valve body.

A hole 523 is provided in the valve body and communicates through a passageway to the nozzle 524 in a manner similar to the communication of the hole in the ball seat disk with the nozzle for passageway 431 and nozzle 414 in the previous embodiment. The flapper disk 518 has a small flapper 526 which, when the disk 518 and disk 521 are installed in the valve body, covers the bottom of a hole 527 in the retainer disk 521.

In this embodiment of the invention, when the press pad 416 is pressed, the pressure created in the hand treatment agent in the dome chamber forces the flapper 519 against the floor 513 of the housing 512 and covers the hole 516, thus cutting off communication between the bag 413 and the chamber in the dome. At the same time the pressure of the hand treatment agent in the dome forces the agent from the chamber out through the hole 527 which forces the flapper 526 into the clearance hole 523 in the housing floor so the agent is forced out of the dome 416 and through the passageway and out the nozzle 524. When the hand pressure is released from the dome, it will resiliently return to its original rest shape. As it does so, the flapper 526 is resiliently returned by the material of the disk and further held tight against the bottom of hole 527, preventing any air from being sucked into the dome. At the same time, as the dome continues to return to original shape, the suction pulls the flapper 519 up into the hole 522, enabling the dome to suck material from the bag 413 through the duct 517, hole 516 and the flapper disk and hole 522 into the dome. It may be noted from this description that the material of the flapper disk 518 and the dome 416 should be a resilient material. An example of that is the Sarlink™ material discussed above. The other materials in this embodiment of the invention may be the same as described above for similar parts in the previously described embodiment. The volume of material dispensed at each dispensing event can be the same as described above with reference to the embodiment of FIGS. 30-40. It should be at least 0.7 ml. Dispensing an amount more than 1.2 ml. per dose is believed not necessary for hand sanitizing.

Other Disposable Dispensers

Referring now to FIGS. 42-47, these show other embodiments of disposable dispensers for hand treatment agent. In these embodiments, the housing may have a valve arrangement like either that of FIG. 40 or FIG. 41. They also have discharge nozzles at the front end and a hanger clip at the rear end. But there are many differences. For example, the agent storage reservoir is a solid-walled tube. Referring particularly to FIGS. 42-45, the valve body 612 has a valve arrangement in it. Instead of a flexible bag for a reservoir, it has a rigid walled plastic tube 613. The rear end of the tube is plugged by a single molded piece 614 which serves to both plug the rear end of the tube and clip to the user's clothing. The plug is sealed to the tube by heat welding or other suitable means. The piece has an integral hinge portion so that the clip can be squeezed to open the jaws and clip onto clothing. The clip has a sharp point 617 which is positioned to puncture a thin wall 618 of the piece 614 when the clip is squeezed. This opens an air tunnel 619 into the tube 613 which admits air to the interior to make up for agent dispensed at each event. The hole is small enough that the agent will not dribble out this way during a dispensing event or between events.

Figure 45:
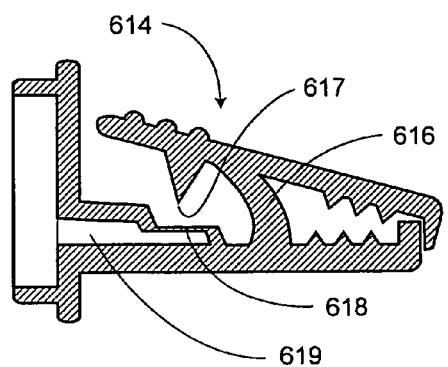
FIG. 45 is a section through the part shown in FIGS. 43 and 44.
Figure 43:
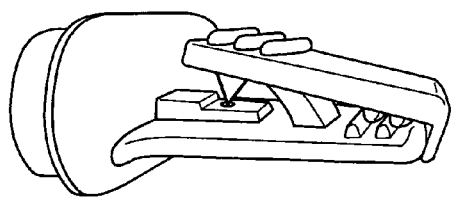
FIG. 43 is an enlarged rear perspective view of the rear end plug and clip member.
Figure 44:
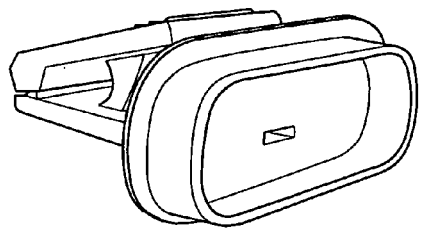
FIG. 44 is an enlarged frontal view of the part shown in FIG. 43.
Figure 46:
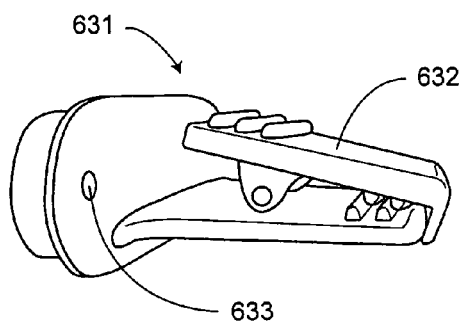
FIG. 46 is a rear perspective view of an alternative rear end plug and clip unit for the hard-bodied reservoir embodiment of FIG. 42.
Figure 47:
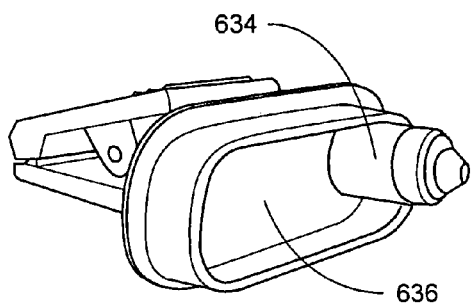
FIG. 47 is a frontal perspective view of the rear end plug of FIG. 46.

Referring now particularly to FIGS. 46 and 47, a type of tube end plug different from that of FIGS. 42-45 is shown. This plug 631 is mountable to the tube 613 in the same manner as plug 614. But in this case, the plug has a pivoting clamp 632 but without a puncture point. The plug has an air hole 633 and a one-way valve 634 press fitted into the plug at the hole 633 and shown at the inside face 636 of the plug. Air can enter the tube to make up for agent discharged by pushing the press pad. This approach can be used with a one-piece molded plug generally as shown in FIGS. 43-45 but there is no need for the point on the clip, or the air tunnel in this instance.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

The invention claimed is:

1. A personal, portable hand treatment agent dispenser comprising:
    a housing;
    a flexible, non-refillable reservoir on said housing and storing a volume of said hand treatment agent;
    at least one port on said housing;
    means on said housing coupled to said reservoir and to said port for receiving a measured portion of said agent from said reservoir, and operable upon actuation, to discharge said measured portion of said agent out from said dispenser through said port; and
    a hanger on said reservoir for hanging the dispenser on a user; and wherein said hanger includes:
    an elongate member which has a proximal end portion and a distal end portion, and wherein the proximal end portion is attached to said reservoir; and there is
    adhesive on said distal end portion for attachment to apparel worn by a user of the dispenser.

2. The dispenser of claim 1 and wherein:
    said dispenser is elongated and has a front end and a rear end, and
    said port is proximate said front end of said dispenser, and said hanger is proximate said rear end of said dispenser and said adhesive is oriented for hanging the dispenser from said apparel with said port below the location of attachment of said adhesive to the apparel.

3. The dispenser of claim 1 and wherein:
    said elongate member is operable from a folded and stored condition against said reservoir, to an open position for adhesive attachment to the user and hanging from the user.

4. A personal, portable hand treatment agent dispenser comprising:
    a housing;
    a flexible, non-refillable reservoir on said housing and storing a volume of said hand treatment agent;
    at least one port on said housing;
    means on said housing coupled to said reservoir and to said port for receiving a measured portion of said agent from said reservoir, and operable upon actuation, to discharge said measured portion of said agent out from said dispenser through said port; and
    a hanger on said reservoir for hanging the dispenser on a user; and wherein:
    said hanger comprises a foldable strip of flexible material having a front face and a back face and a proximal end portion and a distal end portion; and
    said strip has an adhesive surface on a portion of said front face, and an adhesive surface on a portion of said back face; and wherein
    said adhesive surface on said front face is on said proximal end portion of said front face and affixes the proximal end portion of the strip to said reservoir.

5. The dispenser of claim 4 and wherein:
    said adhesive surface on said back face of said strip is on said distal end portion of said strip and enables adhesive attachment of said back face of said distal portion of said strip to said back face of said strip at the proximal end portion of said strip.

6. The dispenser of claim 4 and wherein:
    said strip is made of re-moisturized, semi-bleached super calendared kraft liner;
    the surface of said back face of said trip adjacent the proximal end portion of said strip facilitates temporary adhesive attachment of said adhesive surface on said back face to said back face of said strip adjacent said proximal end of said strip;

said adhesive surface on said back face has the ability to be applied and removed from clothing materials many times and still remain tacky;

said adhesive surface on said front face has the ability to adhere to a pliable polyethylene film material of said reservoir permanently.

7. The dispenser of claim 5 and wherein:

said adhesive surface on said back face is suitable for repeated adhesive attachment to and removal from clothing.

8. The dispenser of claim 5 and wherein:

said adhesive surface on said front face is permanently adhered to said bag reservoir.

9. A personal, portable hand treatment agent dispenser comprising:

a housing;

a reservoir on said housing and storing a volume of said hand treatment agent;

at least one port on said housing;

means on said housing coupled to said reservoir and to said port for receiving a portion of said agent from said reservoir, and operable upon actuation, to discharge said portion of said agent out from said dispenser through said port;

a hanger on said reservoir for hanging the dispenser on a user; and wherein said hanger comprises a foldable strip of flexible material having a front face and a back face and a proximal end portion and a distal end portion; and said strip has an adhesive surface on a portion of said front face, and an adhesive surface on a portion of said back face; and wherein said adhesive surface on said front face is on said proximal end portion of said front face and affixes the proximal end portion of the strip to said reservoir; and wherein said adhesive surface on said back face of said strip is on said distal end portion of said strip and enables adhesive attachment of said back face of said distal portion of said strip to said back face of said strip at the proximal end portion of said strip; and wherein a portion of said back face of said strip and extending from said distal end of said strip to said adhesive surface of said back face, is devoid of said adhesive surface to thereby expose a pull tab to facilitate pulling from folded condition, said distal end portion of said back face of said strip away from adhesive attachment to said proximal end portion of said strip and unfold said strip.

10. The dispenser of claim 9 and wherein:

the overall length of said dispenser from the front end to the rear end is about 15 centimeters when the strip is folded.

11. The dispenser of claim 10 and wherein:

the overall length of said dispenser from the front end thereof to the distal end of said strip when unfolded is about 19.7 centimeters.

12. The dispenser of claim 9 and further comprising:

an indicator on said strip at said distal end portion of said strip to indicate direction to pull said tab to unfold said strip for hanging said dispenser to the clothing of the user.

13. A personal, portable hand treatment agent dispenser comprising:

a housing;

a reservoir on said housing and storing a volume of said hand treatment agent;

at least one port on said housing;

means on said housing coupled to said reservoir and to said port for receiving a portion of said agent from said reservoir, and operable upon actuation, to discharge said portion of said agent out from said dispenser through said port;

a hanger on said reservoir for hanging the dispenser on a user; and wherein said means for receiving and operable to discharge comprises:

a pump having a user press operator pad on said housing to dispense said agent by pressing and displacing said pad from a rest position.

14. The dispenser of claim 13 and wherein:

said pad is a dome of elastomer material having resilience resisting displacement of said pad from said rest position, and having restorative power to return toward original shape.

15. The dispenser of claim 14 and wherein:

said dome encloses a chamber for temporarily holding a dose of limited amount of said agent drawn from said reservoir.

16. The dispenser of claim 15 and wherein:

said reservoir is a bag made of flexible but relatively inelastic material.

17. The dispenser of claim 13 and further comprising:

a chamber in said housing for temporarily holding a dose of limited amount of said agent drawn from said reservoir;

a first passageway in said housing for movement of said agent from said reservoir to said chamber; and a second passageway in said housing for movement of said agent from said chamber to said port for discharging said agent from said dispenser out through said port.

18. The dispenser of claim 17 and further comprising:

a normally-open, one-way valve in said first passageway for admission of said agent from said reservoir into said chamber; and a normally-closed, one way valve in said second passageway to normally prevent passage of said agent from said chamber to said port.

19. The dispenser of claim 18 and wherein said normally-open valve is normally open to passage of said agent in a direction from said reservoir to said chamber.

20. The dispenser of claim 19 and wherein:

said valves are one-way flapper valves.

21. The dispenser of claim 18 and wherein:

said valves are ball check valves.

22. The dispenser of claim 17 and wherein;

said first passageway has an entrance in a wall of said housing at said reservoir; and said dispenser further comprising at least one stand-off to prevent said material of said reservoir from closing said entrance.

23. The dispenser of claim 16 and wherein:

said reservoir has a capacity to store between 10 and 75 milliliters of said hand treatment agent; and said means for receiving and operable to discharge is arranged to limit the volume of said agent discharged at each event of pressing said operator pad, to a maximum of less than about 3.0 milliliters.

24. The dispenser of claim 23 and wherein:

the weight of said dispenser when filled with said hand treatment agent is between one and five ounces.

25. The dispenser of claim 23 and wherein:

about 30 milliliters of said hand treatment agent is stored in said reservoir.

26. The dispenser of claim 14 and wherein:

said pad has a capacity to discharge at least 0.7 milliliters of hand cleaning agent when pressed to collapse fully.

27. The dispenser of claim 14 and wherein:

said pad is constructed and arranged to provide an audible and tactile response when said pad is pressed enough from said rest condition to discharge from said port an amount of hand cleaning agent between 0.7 milliliters and 1.2 milliliters.

28. The dispenser of claim 13 and wherein:

said press operator pad has ridges thereon to provide tactile feedback to a user's digit finger or thumb; and said housing bottom surface has downwardly-opening grooves thereon to provide tactile feedback to a user's digit finger or thumb when operating said pad.

* * * * *